United States Patent
Zitterbart et al.

(10) Patent No.: US 12,391,727 B2
(45) Date of Patent: *Aug. 19, 2025

(54) TRACELESS REDUCTIVELY CLEAVABLE LINKER MOLECULES FOR PEPTIDE PURIFICATION

(71) Applicant: GYROS PROTEIN TECHNOLOGIES AB, Uppsala (SE)

(72) Inventors: Robert Zitterbart, Berlin (DE); Oliver Reimann, Berlin (DE)

(73) Assignee: GYROS PROTEIN TECHNOLOGIES AB, Uppsala (SE)

(*) Notice: Subject to any disclaimer, the term of this patent is extended or adjusted under 35 U.S.C. 154(b) by 0 days.

This patent is subject to a terminal disclaimer.

(21) Appl. No.: 18/321,803

(22) Filed: May 23, 2023

(65) Prior Publication Data

US 2024/0116981 A1    Apr. 11, 2024

Related U.S. Application Data

(63) Continuation of application No. 17/270,936, filed as application No. PCT/EP2019/072894 on Aug. 27, 2019, now Pat. No. 12,269,845.

(30) Foreign Application Priority Data

Aug. 27, 2018  (EP) ..................................... 18191038
Dec. 13, 2018  (EP) ..................................... 18212487

(51) Int. Cl.
*C07K 1/22* (2006.01)
*C07C 247/18* (2006.01)
*C07D 213/75* (2006.01)
*C07D 295/185* (2006.01)

(52) U.S. Cl.
CPC .............. *C07K 1/22* (2013.01); *C07C 247/18* (2013.01); *C07D 213/75* (2013.01); *C07D 295/185* (2013.01)

(58) Field of Classification Search
CPC ....... C07K 1/22; C07C 247/18; C07C 271/08; C07C 271/20; C07C 323/63; C07C 323/25; C07D 213/75; C07D 295/185; C07D 209/48; C07D 213/56; C07D 213/66; C07D 213/71; C07D 213/74; C07D 213/76; C07D 213/77; C07D 213/82; C07D 233/64; C07D 237/08; C07D 239/26; C07D 239/42; C07D 285/01; C07D 417/04; C07D 401/12; C07D 417/10

See application file for complete search history.

(56) References Cited

U.S. PATENT DOCUMENTS

2012/0270937 A1* 10/2012 Warnecke ............ A61K 47/555
                                                        514/483
2017/0226159 A1*  8/2017 Takatsu .................. B01D 15/08
2019/0309013 A1* 10/2019 Zitterbart .............. C07C 243/26

FOREIGN PATENT DOCUMENTS

JP        7550137       9/2024
WO     1992006107      4/1992
WO     2017129818      8/2017

OTHER PUBLICATIONS

He et al, Molecules, 2019, 24, 1855, 1-34 (Year: 2019).*
Lu et al, International Journal of Molecular Sciences, 2016, 17, 561, 1-22] (Year: 2016).*
Chen et al. Adv. Drug Deliv. Rev. 65:1357-1369, 2013) (Year: 2013).*
Verdine et al (Methods in Enzymology, 2012, vol. 503, 3-33) (Year: 2012).*
Mende et al: "Automated Fmoc-Based Solid-Phase Synthesis of Peptide Thioesters with Self-Purification Effect and Application in the Construction of Immobilized SH3 Domains", Journal of the American Chemical Society, 2010, vol. 132 (32), p. 11110-11118.
Karas et al: "The efficient synthesis and purification of amyloid-β(1-42) using an oligoethylene glycol-containing photocleavable lysine tag", Chemical Communications, 2017, and vol. 53 (51), p. 6903-6905.
Brakel et al "A doxorubicin prodrug activated by the staudinger reaction", Bioconjugate Chemistry, 2008, vol. 19 (3), p. 714-718.

* cited by examiner

*Primary Examiner* — Sudhakar Katakam
(74) *Attorney, Agent, or Firm* — JMB Davis Ben-David

(57) ABSTRACT

The present invention relates to linker molecules of formula (1), $X\text{-}T_b\text{-}V_a\text{—}U\text{—}Y\text{—}Z$ (1) and a method for purifying peptides using said linker molecules. The linker molecule can be coupled to a purification resin via the moiety X and to a peptide via the moiety Y under the release of the leaving group Z. T is an optional spacer moiety and V is an optional electron withdrawing moiety. U is an aryl or 5- or 6-membered heteroaryl moiety bound to at least one electron withdrawing moiety V, W or E. The linker is stable under acidic conditions and releases the peptide upon addition of a reducing agent.

14 Claims, 13 Drawing Sheets

Specification includes a Sequence Listing.

TRACELESS REDUCTIVELY CLEAVABLE LINKER MOLECULES FOR PEPTIDE PURIFICATION

CROSS-REFERENCE TO RELATED APPLICATIONS

This is a Continuation of U.S. patent application Ser. No. 17/270,936 filed on Feb. 24, 2021, which is the U.S. National Stage of International Patent Application No. PCT/EP2019/072894 filed on Aug. 27, 2019, which in turn claims the benefit of European Patent Application No. 18191038.1 filed on Aug. 27, 2018 and European Patent Application No. 18212487.5 filed on Dec. 13, 2018.

FIELD OF THE INVENTION

The present invention relates to a method of purifying peptides or peptide nucleic acids produced by solid phase peptide synthesis (SPPS) and linker molecules for use in said purification.

BACKGROUND OF THE INVENTION

Solid phase peptide synthesis is an established method for the synthesis of peptides. A standard procedure is the coupling of the first N-terminally protected amino acid to a synthesis resin followed by repeated cycles of deprotection of the N-terminus, coupling the next N-terminally protected amino acid and capping of unreacted peptide sequences. Finally, the synthesized peptide is cleaved off the synthesis resin and purified.

A widely-used method for the purification of peptides is the preparative high performance liquid chromatography (HPLC). Disadvantageous at this method is the poor scalability with regard to the desired production quantities, so that different quantities cannot be produced with one and the same system. This causes relatively high acquisition costs for the corresponding complex devices. A further disadvantage is the requirement of relatively extensive knowledge for a correct analytical assessment of the individual fractions. Additionally, HPLC purification involves a high consumption of solvents and occasionally of column material (solid phase) during operation.

Therefore, methods that are cheaper and less prone to faults would be advantageous for reducing the costs of peptide production.

Alternative methods use linker molecules that can be attached to peptides and thereafter coupled to a functionalized solid phase that is used during purification.

EP 0 552 368 A1 describes a linker molecule bearing a thiol that can be covalently bound to a purification support. However, the method is not suitable for thiol-containing peptides such as those comprising the amino acid cysteine or penicillamine.

EP 2 501 711 B1 proposes an analogous method in which the linker is bound to a solid phase via a 1,3-dipolar cycloaddition between an azide ($-N_3$) and an alkyne which requires the presence of copper. However, peptides that comprise methionine, cysteine; arginine or lysine may complex copper making a removal difficult. Due to the toxicity of copper, such peptides are not suitable for all applications such as pharmaceutical use.

WO2017129818 (A1) discloses linker molecules that may be coupled to a peptide that is still bound to the synthesis resin after SPPS. The peptide is then cleaved off the synthesis by applying commonly used TFA conditions. However, a disadvantage of the linker molecules that form a benzyl-carbamate with the peptide as disclosed in WO2017129818 (A1) is their lability to acidic treatment (TFA>50%, in presence of water pH<0). Premature decay of the linker molecules causes significantly reduced yield of purified peptide.

Unwanted side reactions also occur with peptides that contain Thr, Ser or Cys at their N-terminus due to a nucleophilic attack of the β-hydroxyl or β-thiol group on the sulfo-ethyleneyl carbamate moiety of the linker under the basic conditions (pH>9) that are used for release of the peptide. Further side reactions of linker molecules disclosed in WO2017129818 (A1) are aspartimide formation and the conversion of arginine to citrulline at Arg-Glu sequences and disulfide formation and nucleophilic side reactions by internal Cys residues under basic conditions.

Furthermore, the sulfone linkers described in WO2017129818 (A1) suffer from a reactive vinyl sulfone moiety that remains on the solid report and needs an additional quenching step.

To overcome the disadvantage of side reactions under basic conditions and premature decay of the linker under acidic conditions, the present invention provides linker molecules that are stable under TFA conditions and allow peptide release under mild acidic conditions, in particular at pH≤7.

SUMMARY

Described herein are novel compounds comprised of formula 1, $X-T_b-V_a-U-Y-Z$ (1), wherein X is selected from a group consisting of a moiety of formula 2, 2a, 3, 3a and 4,

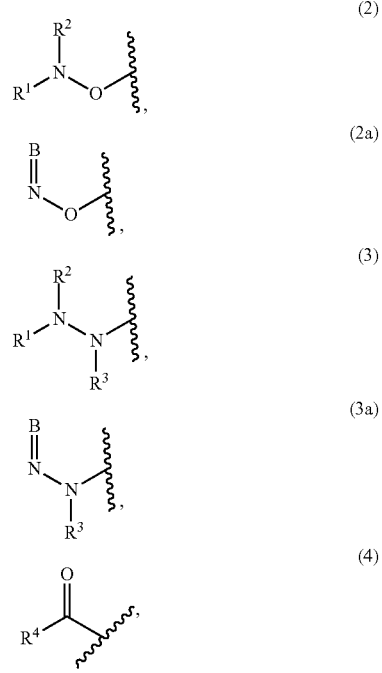

wherein each $R^1$ and $R^2$ is independently from each other H or B, wherein at least $R^1$ or $R^2$ is B, $R^3$ is H or B, $R^4$ is H, $C_1$-$C_{12}$-alkyl or aryl, wherein the aldehyde or keto group may be protected by an acid labile protecting group, B is an acid labile amine protecting group, T is a linear or branched spacer comprising 1 to 5 of the moieties selected from: —$C_{1-12}$-alkyl-, (—$C_2H_4$O—)$_{1-12}$, —C(=O)—, —C(=O)-$JR^9$—, -$JR^9$—C(=O)—, -$JR^9$—, phenyl, 5- or 6-membered heteroaryl, J is CH or N, and wherein $R^9$ is selected from the group consisting of H, $C_{1-4}$-alkyl, —$C_{1-6}$-alkyl-$NH_2$, —$C_{1-6}$-alkyl-NHB, —$C_{1-6}$-alkyl-$NB_2$, —$R^{15}$, —$C_{1-6}$-alkyl-$R^{15}$, and —$C_{1-6}$-alkyl-NH—$R^{15}$, wherein B is an independently selected acid labile amine protecting group, $R^{15}$ is a blocking agent that is able to react with an aldehyde moiety selected from the group consisting of cysteinyl, threoninyl, 2-mercaptoethanol, cysteamine, ethandithiole, hydroxylamine, O-methylhydroxylamine, N-methylhydroxylamine, dithiothreitol, and hydrazine, wherein:

amine and/or thiol moieties of the blocking agent may be protected by an acid labile amine protecting group B, and/or an acid labile thiol protecting group, b is 0 or 1, V is an electron-withdrawing moiety selected from the group consisting of —$NR^{11}$—C(=O)—, —C(=O)—$NR^{11}$—, —S(=O)—, —$NR^{12}$—(CH$_2$)$_p$—, -piperazinyl-(CH$_2$)$_p$—, -pyridinyl-, and pyrimidinyl, wherein $R^{11}$ is selected from the group consisting of H and $C_{1-4}$-alkyl, $R^{12}$ is selected from the group consisting of H and $C_{1-4}$-alkyl, p is 0, 1 or 2, a is 1, wherein the sum of a and b is 1 or 2, U is a phenyl or a five- or six-membered heteroaryl moiety, that is bound to at least one of the moieties V, $W_q$ and $E_n$ and that is unsubstituted or substituted by $C_{1-6}$-alkyl, wherein V is defined as described above, W is selected from the group consisting of —$N_3$, —$NO_2$, —S(=O)—$R^8$, —S—S—$R^8$, —O—CH$_2$—$N_3$, —O—C(=O)—O—CH$_2$—$N_3$, —N=N-phenyl, —N=N—$R^8$,

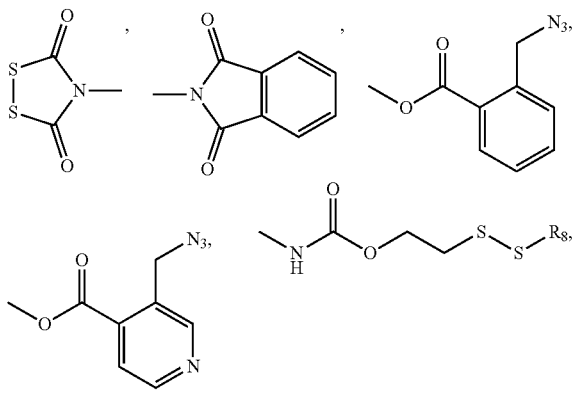

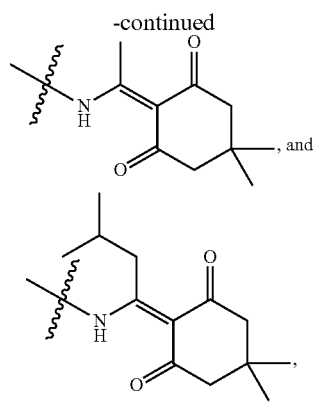

wherein $R^8$ is pyridyl, pyrimidinyl, pyrazinyl, pyridazyl, —$C_1$-$C_6$-alkyl or —(CH$_2$)$_p$—NMe$_2$, p is 1, 2, 3 or 4, E is an electron withdrawing group under acidic conditions, n is an integer between 0 and 4, and q is an integer between 1 and 4, wherein the sum of n and q is equal or lower than 4, and wherein when U is a phenyl moiety and Y is —(CH$_2$)$_m$—O—C(=O)—, the sum of Hammett constants of V, W, E under acidic conditions is larger than 0.45, and wherein W is in ortho or para position in relation to Y, Y is —(CH$_2$)$_m$—C(=O)— or —(CH$_2$)$_m$—O—C(=O)—, m is 1, 2 or 3, and Z is an electron-withdrawing leaving group.

(SEQ ID NO: 5) and P6 (H-CKADEVSMHKWYG-NH$_2$) (SEQ ID NO: 6) by usage of inventive linker molecule X1. A=absorption (210 nm), B=time/min; 1.) Chromatogram of crude peptide sample before linker coupling to peptide. 2.) Chromatogram of peptide after purification by usage of linker X1 and method as described in claim 10.

General Remarks to FIGS. 5 to 8

In FIG. 5-8 the following abbreviations are used: P=peptide, E=the arrow shows the direction of electron withdrawal or donation a) TFA cleavage of the synthetic resin (SR) to gain linker modified peptide, b) Incubation with an aldehyde functionalized solid support to immobilize the linker modified peptide on those purification beads (PB), c) washing of beads to remove synthetic impurities, d) reduction by addition of a reducing agent, e) washing away the reductive agent, f) adjusting the pH to generate a releasing electronic structure g) spontaneous decomposition of the linker molecule by whether a 1,6-, 1,4-elimination or a nucleophilic attack.

Figure 5:
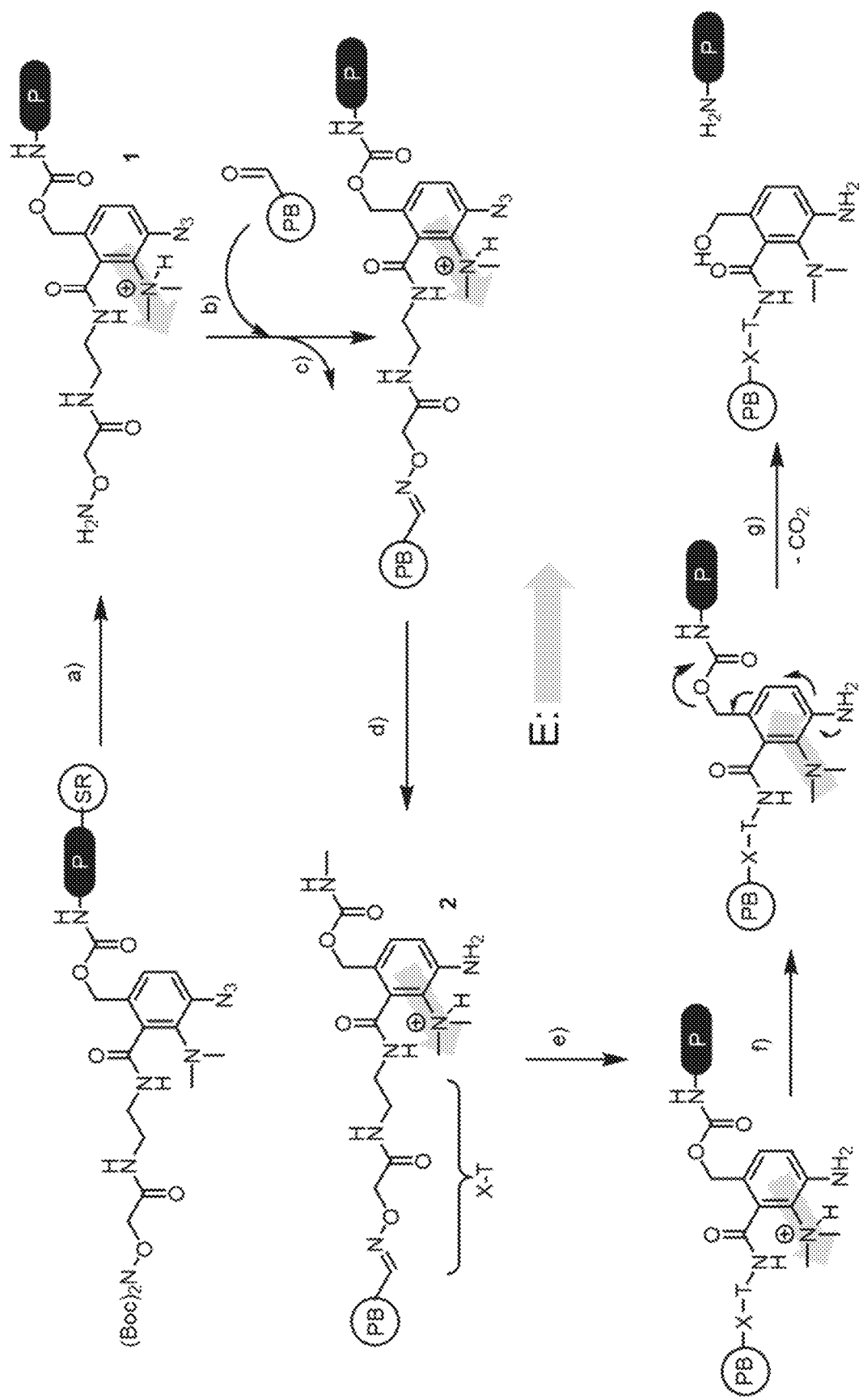

FIG. 5 shows an amine switch with an azide reductive safety lock (type 1). The basic nitrogen atom in conjugation with the cleavable aromatic core withdraws electrons when it is protonated (E: arrow). The positive charge in structure 1 enhances the solubility and provides TFA stability during the acidic cleavage of the linker-peptide construct of the synthetic resin (SR). The peptide release is performed in two steps. First, the azide (moiety W) is reduced to —NH$_2$, thus the safety lock for the release is removed. The stability of the linker is still retained after reduction in structure 2 due to the electron withdrawal of the protonated amine group, if the pH is lower than the pKa of the most basic nitrogen. This allows the removal of the reducing agent and washing under acidic conditions. In a second step, the purified peptide is released by increasing the pH to pH>pKa of the most basic nitrogen. The increase in pH induces a 1,6-elimination reaction. The linker decays under the release of CO$_2$. The peptide is obtained with a free N-terminus.

Figure 6:
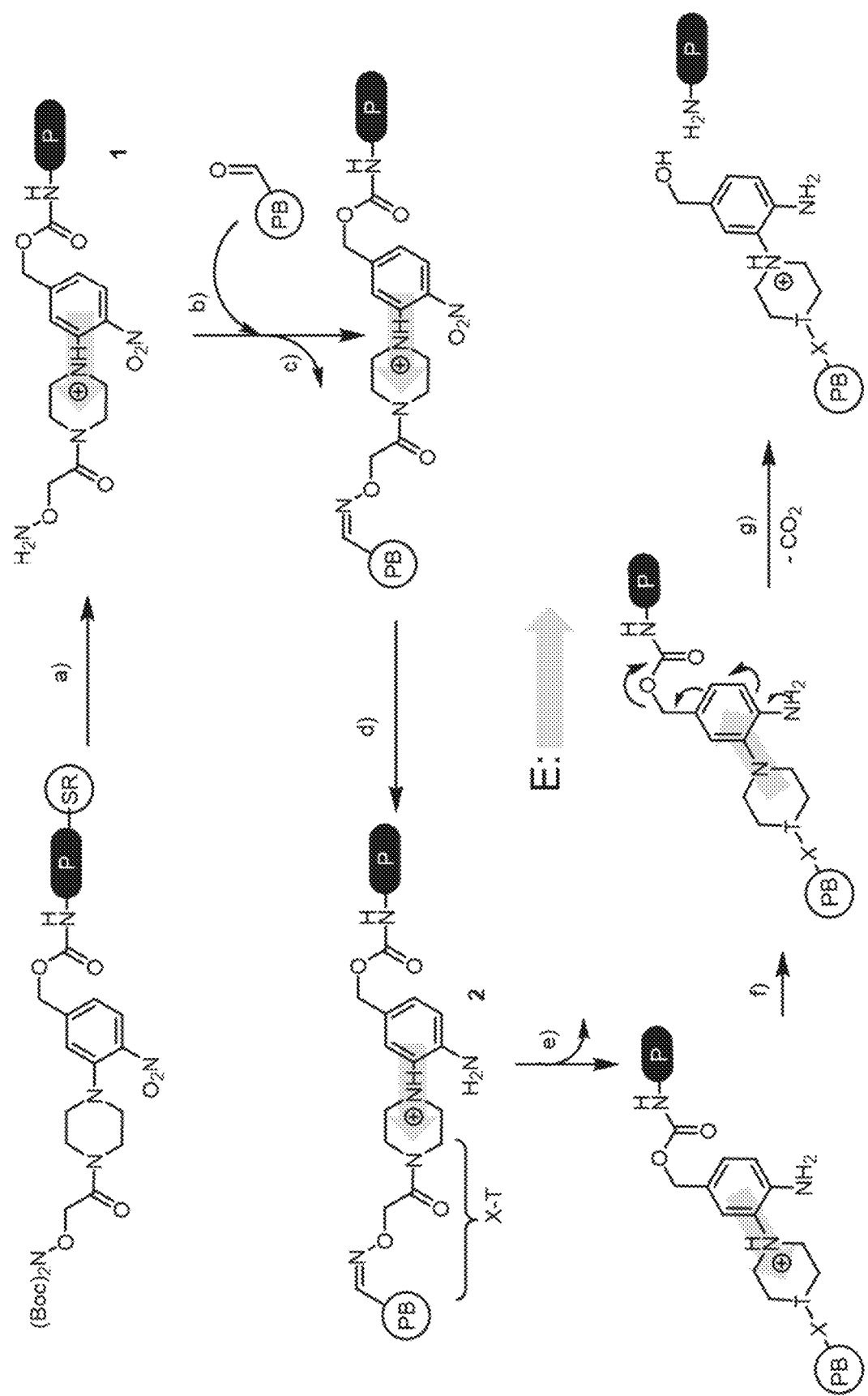

FIG. 6 shows an amine switch with a reductive safety lock without azide but another reducible moiety such as a nitro, disulfide or azo group (type 2). The basic nitrogen atom in conjugation with the cleavable aromatic core withdraws electrons when it is protonated (E: arrow). The positive charge in structure 1 enhances the solubility and provides TFA stability during the acidic cleavage of the linker-peptide construct of the synthetic resin (SR). The peptide release is performed in two steps. First, the nitro (moiety W) is reduced to —NH$_2$, thus the safety lock for the release is removed. The stability of the linker is still retained after reduction in structure 2 due to the electron withdrawal of the protonated amine group, if the pH is lower than the pKa of the most basic nitrogen. This allows the removal of the reducing agent and washing under acidic conditions. In a second step, the purified peptide is released by increasing the pH to pH>pKa of the most basic nitrogen. The increase in pH induces a 1,6-elimination reaction. The linker decays under the release of CO$_2$. The peptide is obtained with a free N-terminus.

Figure 7:
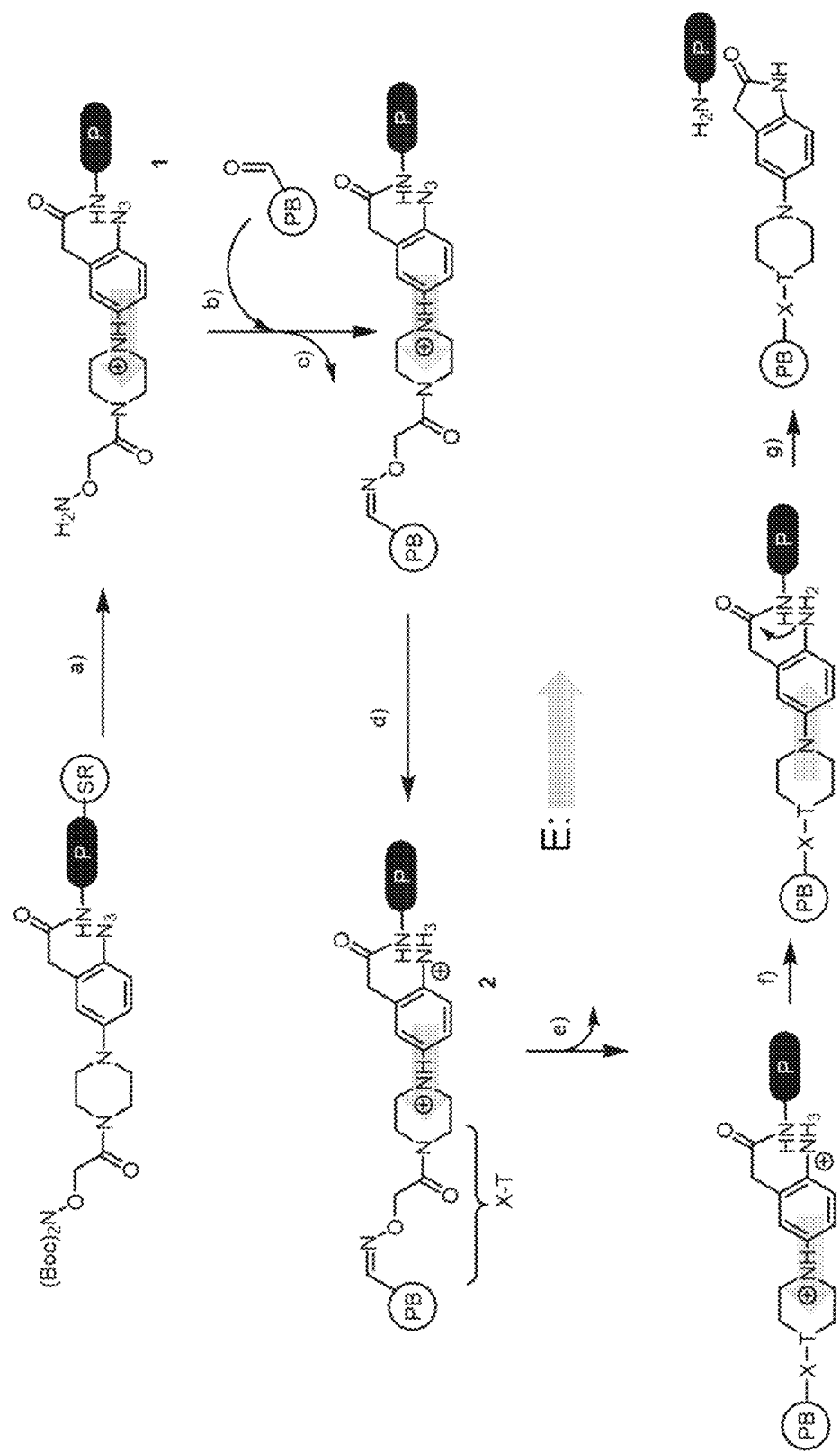

FIG. 7 shows an amine switch with a nucleophilic release (type 3). Linkers that are able to release the peptide via nucleophilic release comprise a carboxylate (Y=C(=O), Z=OH) instead of a carbonate moiety (Y=—O—C(=O), Z=O—R). Without a carbonate, the linker shows enhanced stability in solution and storage. Coupling to the peptide may be performed as common amino acid coupling resulting in an amide bond instead of a carbamate bond. Due to the lack of a carbamate bond, the linker is stable under acidic conditions such as TFA. Also here, the peptide release is performed in two steps. First, the reducible moiety (—N$_3$) is reduced to amine, thus the safety lock for the release is removed. The stability of the linker is still retained after reduction if the pH is higher than the pKa of the most basic nitrogen. This allows the removal of the reducing agent and washing under acidic conditions. In a second step, the purified peptide is released by increasing the pH to pH>pKa of the most basic nitrogen. The increase in pH induces a nucleophilic release and the peptide is obtained with a free N-terminus.

The stability of the linker is still retained after reduction if the pH is higher than the pKa of the carbamate.

Figure 8:
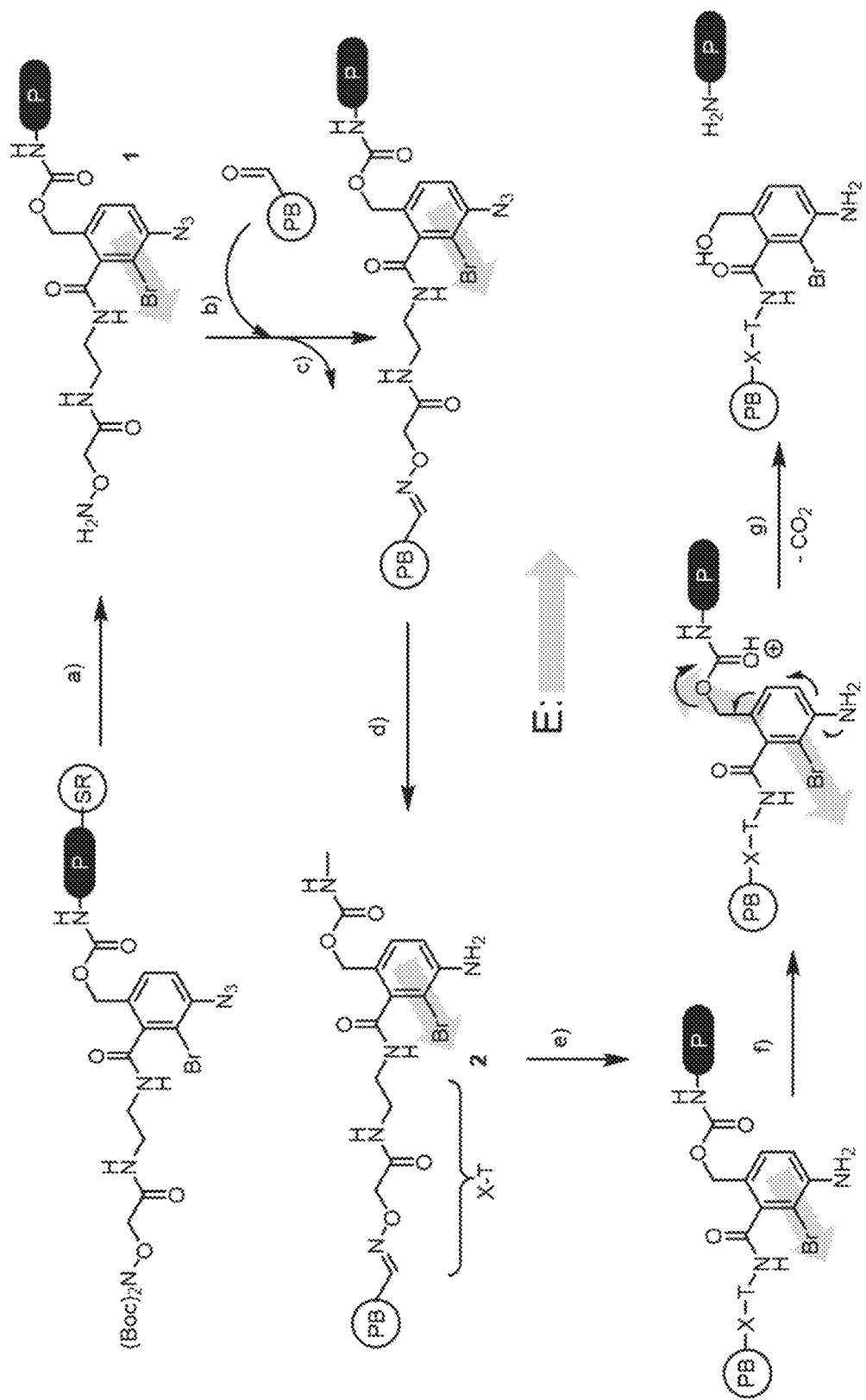

FIG. 8 shows a carbamate switch (type 4). Linkers that are able to release the peptide via a carbamate switch comprise a moiety Y=—O—(=O)—. Furthermore, the linkers comprise an electron-withdrawing moiety E, e.g. —Br, and a reducible moiety W, e.g. —N$_3$. TFA-stability is mediated by the electron-withdrawing moiety —Br during TFA-cleavage, immobilization of the linker-peptide construct on a solid support, e.g. a purification resin, and subsequent washing steps under acidic conditions. Upon reduction of the reducible moiety —N$_3$ to —NH$_2$, the safety lock for the release is removed. The linker is stable when the pH is higher than the pKa of the carbamate. This allows the removal of the reducing agent and washing. Finally, the purified peptide is released by decreasing the pH to pH<pKa of the carbamate by 1,6- or 1,4-elimination and the release of CO$_2$. The peptide is obtained with a free N-terminus.

Figure 9:
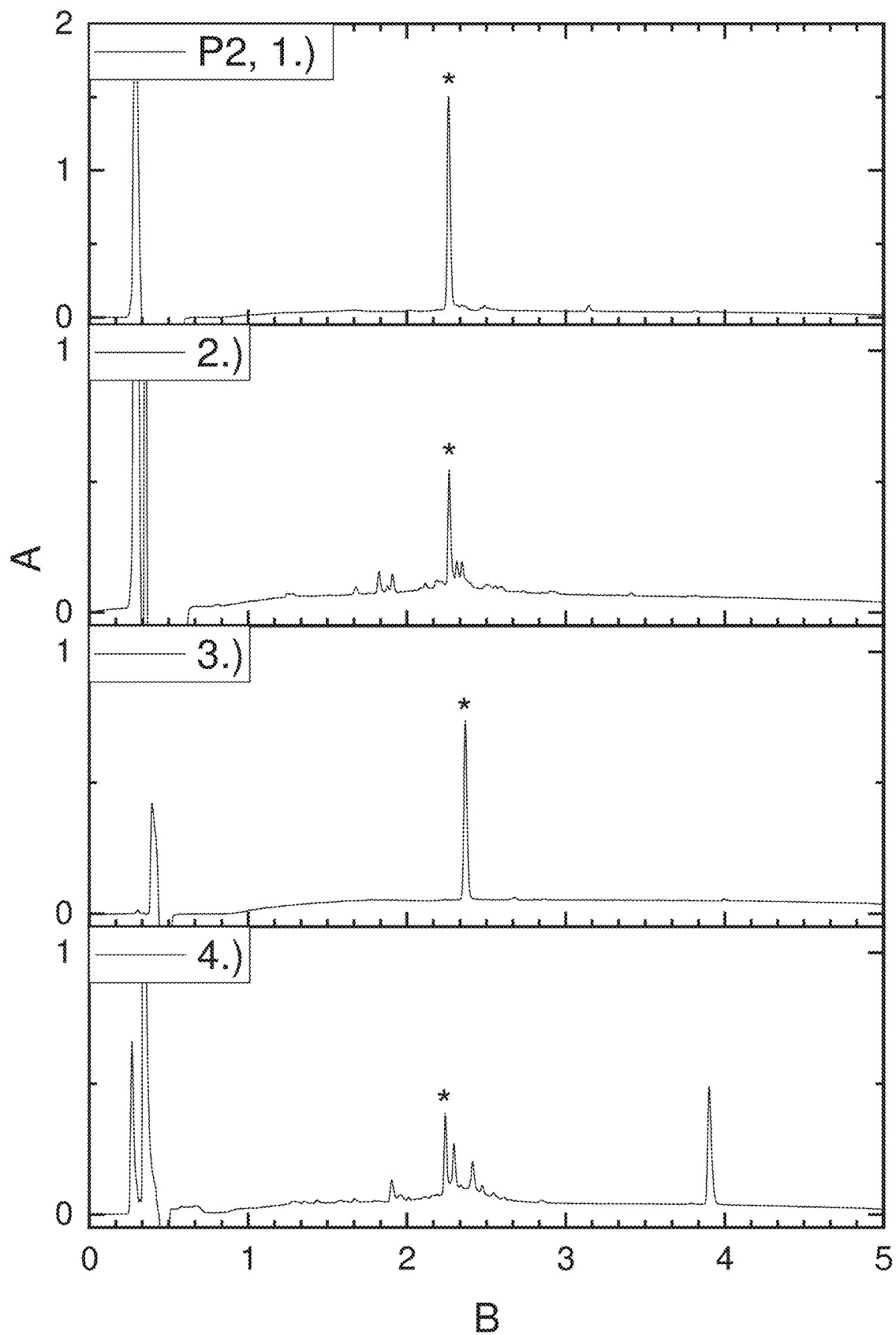

FIG. 9 shows each an example of the inventive peptide purification of peptide P2 (H-AKADEVSLHKWYG-NH$_2$) (SEQ ID NO: 2) by usage of 3 inventive linker molecules 2.) X9 of type 1 amine switch with azide reductive safety lock, 3.) X13 of type 2 amine switch with other reductive safety lock and 4.) X22 of type 3 amine switch with nucleophilic release. A=absorption (210 nm), B=time/min; Identity of isolated peptide was always confirmed by UPLC-ESI/MS analysis. Identified P2 product is marked with *. 1.) Chromatogram of crude peptide sample before linker coupling to P2 (*). 2.) Chromatogram of P2 (*) after purification by usage of linker X9 of type 1 and the corresponding method as described in example section below. 3.) Chromatogram of P2 (*) after purification by usage of linker X13 of type 2 and the corresponding method as described in example section below. 4.) Chromatogram of P2 (*) after purification by usage of linker X22 of type 3 and the corresponding method as described in example section below.

BRIEF DESCRIPTION OF THE DESCRIBED SEQUENCES

The nucleic and/or amino acid sequences provided herewith are shown using standard letter abbreviations for nucleotide bases, and one letter code for amino acids, as defined in 37 CFR 1.831 through 37 CFR 1.835. Only one strand of each nucleic acid sequence is shown, but the complementary strand is understood as included by any reference to the displayed strand.

The Sequence Listing is submitted as an XML file named 95083_355_3001_seq_listing, approximately 2 KB, created May 4, 2023, the contents of which are incorporated by reference herein in their entirety.

DETAILED DESCRIPTION

According to a first aspect of the invention, a compound of formula 1, X-T$_b$-V$_a$—U—Y—Z (1), is provided, wherein X is selected from a moiety of formula 2, 2a, 3, 3a or 4, in particular of formula 2, 2a, 3 or 3a, more particularly of formula 2 or 2a,

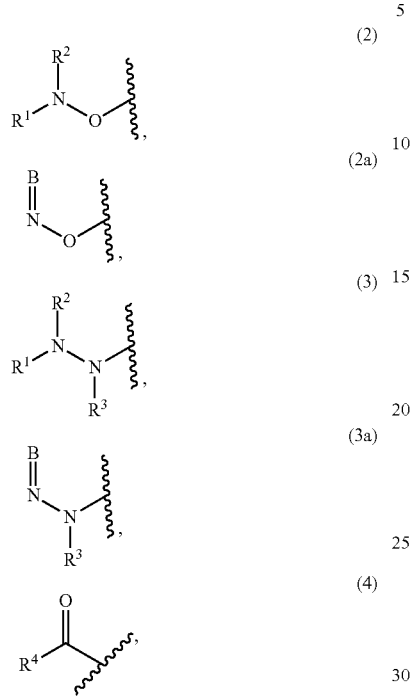

wherein
each $R^1$ and $R^2$ is independently from each other selected from H or B, wherein at least $R^1$ or $R^2$ is B, $R^3$ is selected from H or B,
$R^4$ is selected from H, $C_1$-$C_{12}$-alkyl or aryl, wherein the aldehyde or keto group may be protected by an acid labile protecting group,
B is an acid labile amine protecting group,
T is a linear or branched spacer comprising at least one, particularly 1 to 5, more particularly 1 to 3, of the moieties —$C_{1-12}$-alkyl-, (—$C_2H_4O$—)$_{1-12}$, —C(=O)—, —C(=O)-J$R^9$-, -J$R^9$—C(=O)—, -J$R^9$—, phenyl, 5- or 6-membered heteroaryl, particularly —$C_{1-12}$-alkyl-, (—$C_2H_4O$—)$_{1-12}$, —C(=O)—, —C(=O)-J$R^9$—, -J$R^9$—C(=O)—, -J$R^9$—, wherein
J is CH or N, in particular N,
in particular T is a spacer selected from
—$C_1$-$C_{12}$-alkyl-, in particular —$C_{1-6}$-alkyl-, more particularly —$C_{1-3}$-alkyl-, —$R^5$—C(=O)—, —$R^5$—C(=O)—$NR^9$—$R^6$—, —$R^5$—C(=O)—$NR^9$—, —C(=O)—$NR^9$—$R^6$—, —$R^5$—$NR^9$—C(=O)—$R^6$—, —$R^5$—$NR^9$—$R^{5'}$—$NR^{9'}$C(=O)—$R^6$—, —$R^5$—C(=O)—$NR^9$—$R^{5'}$—$NR^{9'}$—C(=O)—$R^6$—, —$R^5$—$NR^9$—, —$R^5$—$NR^9$—$R^6$—, —$R^5$—$NR^9$—$R^{5'}$—$NR^{9'}$—$R^6$—, —$R^5$—C(=O)—$NR^9$—$R^{5'}$—$NR^{9'}$—$R^6$—, —$R^5$—C(=O)—O—$R^6$—, —C(=O)—O—$R^6$—, —$R^5$-phenyl-$R^6$—, —$R^5$-phenyl-, -phenyl-$R^6$—, -phenyl-, —$R^5$-pyrroyl, —$R^5$-pyrazoyl, —$R^5$-imidazoyl, $R^5$-piperazinyl-, —$R^5$-pyridinyl, —$R^5$-pyrimidinyl, —$R^5$-pyrazinyl, —$R^5$-pyridazinyl, —$R^5$-pyrroyl-$R^6$—, —$R^5$-pyrazoyl-$R^6$—, —$R^5$-imidazoyl-$R^6$—, —$R^5$-piperazinyl-$R^6$—, —$R^5$-pyridinyl-$R^6$—, —$R^5$-pyrimidinyl-$R^6$—, —$R^5$-pyrazinyl-$R^6$—, —$R^5$-pyridazinyl-$R^6$—, pyrroyl-$R^6$—, pyrazoyl-$R^6$—, imidazoyl-$R^6$—, piparazinyl-$R^6$—, pyridinyl-$R^6$—, pyrimidinyl-$R^6$—, pyrazinyl-$R^6$—, pyridazinyl-$R^6$—, pyrroyl, pyrazoyl, imidazoyl, piperazinyl, pyridinyl, pyrimidinyl, pyrazinyl and pyridazinyl, wherein
$R^5$, $R^{5'}$ and $R^6$ are independently from each other selected from $C_1$-$C_{12}$-alkyl or (—$C_2H_4O$—)$_{1-12}$, in particular $C_1$-$C_6$ alkyl, particularly $C_1$-$C_3$ alkyl, and wherein
$R^9$ and $R^{9'}$ are independently from each other selected from H, $C_{1-4}$-alkyl, —$C_{1-6}$-alkyl-$NH_2$, —$C_{1-6}$-alkyl-NHB, —$C_{1-6}$-alkyl-$NB_2$, —$R^{15}$, —$C_{1-6}$-alkyl-$R^{15}$, —$C_{1-6}$-alkyl-NH—$R^{15}$, in particular from H and $C_{1-2}$-alkyl, more particularly $R^9$ is H, wherein
B is an independently selected acid labile amine protecting group,
$R^{15}$ is a blocking agent that is able to react with an aldehyde moiety, in particular $R^{15}$ is selected from cysteinyl, threoninyl, 2-mercaptoethanol, cysteamine, ethandithiole, hydroxylamine, O-methylhydroxylamine, N-methylhydroxylamine, dithiothreitol, hydrazine, in particular cysteinyl and N-methylhydroxylamine, more particularly cysteinyl, wherein
amine and/or thiol moieties of the blocking agent may be protected by an independently selected acid labile amine protecting group B, particularly Boc, and/or an acid labile thiol protecting group, particularly trityl.
b is 0 or 1, in particular 1,
V is an electron-withdrawing moiety selected from —$NR^{11}$—C(=O)—, —C(=O)—$NR^{11}$—, —S(=O)—, —$NR^{12}$($CH_2$)$_p$—, -piperazinyl-($CH_2$)$_p$—, -pyridinyl, pyrimidinyl, pyrazinyl, pyridazinyl,

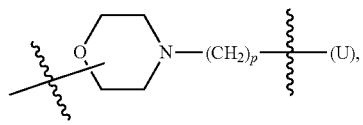

—C(=O)—, —C(=O)—O—, in particular —$NR^{11}$—C(=O)—, —C(=O)—$NR^{11}$—, —S(=O)—, —$NR^{12}$—($CH_2$)$_p$—, -piperazinyl-($CH_2$)$_p$—, -pyridinyl-, pyrimidinyl, more particularly from —NH—C(=O)—, —C(=O)—NH—, —N—($CH_3$)—, -piperazinyl-($CH_2$)$_p$—, -pyridinyl-, pyrimidinyl, wherein
$R^{11}$ is selected from H and $C_{1-4}$-alkyl, in particular from H and $C_{1-2}$-alkyl, more particularly $R^{11}$ is H,
$R^{12}$ is selected from H and $C_{1-4}$-alkyl, in particular from H and $C_{1-2}$-alkyl, more particularly $R^{12}$ is methyl,
p is 0, 1 or 2, particularly 0 or 1,
a is 0 or 1, wherein the sum of a and b is 1 or 2,
U is a phenyl or a five- or six-membered heteroaryl moiety, in particular a phenyl or a six-membered heteroaryl moiety, more particularly a phenyl, that is bound to at least one of the moieties V, $W_q$ and $E_n$ and that may optionally be substituted by $C_{1-6}$-alkyl, in particular $C_{1-3}$-alkyl, wherein
V is defined as described above,
W is selected from —$N_3$, —$NO_2$, —S(=O)—$R^8$, —S—S—$R^8$, —O—$CH_2$—$N_3$, —O—C(=O)—O—$CH_2$—$N_3$, —N=N-phenyl, —N=N—$R^8$,

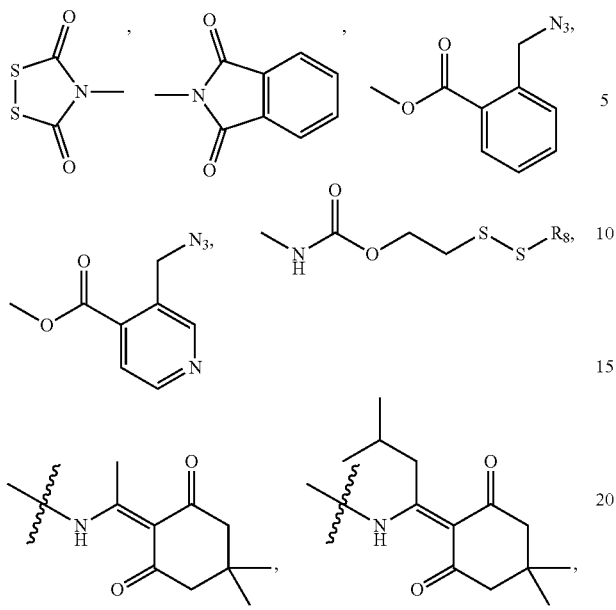

in particular —N₃, —N=N—R⁸, —O—CH₂—N₃, —S—S—R⁸, wherein

R⁸ is pyridyl, pyrimidinyl, pyrazinyl, pyridazyl, —C₁-C₆-alkyl or —(CH₂)$_p$—NMe₂, in particular pyridyl or —C₁-C₆-alkyl, with p being 1, 2, 3 or 4, E is an electron withdrawing group under acidic conditions, n being is an integer between 0 and 4, in particular 0 and 2, more particularly 0 or 1, and q is an integer between 0 and 4, in particular 0 and 2, more particularly 0 and 1, wherein the sum of n and q is equal or lower than 4, and wherein in case of U being a phenyl moiety and Y being —(CH₂)$_m$—O—C(=O)—, the sum of Hammett constants of V, W, E under acidic conditions is larger than 0.45, and wherein W is in ortho or para position in relation to Y, Y is —(CH₂)$_m$—C(=O)— or —(CH₂)$_m$—O—C(=O)— with m being 1, 2 or 3, in particular 1 or 2, more particularly 1, Z is an electron-withdrawing leaving group.

In certain embodiments,

X is selected from a moiety of formula 2, 2a, 3, 3a or 4, in particular of formula 2, 2a, 3 or 3a, more particularly of formula 2 or 2a,

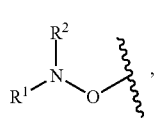  (2)

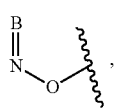  (2a)

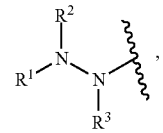  (3)

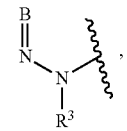  (3a)

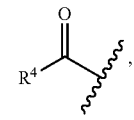  (4)

wherein each R¹ and R² is independently from each other selected from H or B, wherein at least R¹ or R² is B, R³ is selected from H or B, R⁴ is selected from H, C₁-C₁₂-alkyl or aryl, wherein the aldehyde or keto group may be protected by an acid labile protecting group, B is an acid labile amine protecting group, T is a linear or branched spacer comprising at least one of the moieties —C₁₋₁₂-alkyl-, (—C₂H₄O—)₁₋₁₂, —C(=O)—, —C(=O)-JR⁹—, -JR⁹—C(=O)—, -JR⁹—, wherein J is C or N, in particular N, in particular T is a spacer selected from
—C₁-C₁₂-alkyl-, in particular C₁₋₆-alkyl, more particularly C₁₋₃-alkyl, —R⁵—C(=O)—, —R⁵—C(=O)—NR⁹—R⁶—, —R⁵—C(=O)—NR⁹—, —C(=O)—NR⁹—R⁶—, —R⁵—NR⁹—C(=O)—R⁶—, —R⁵—NR⁹—R⁵'—NR⁹'C(=O)—R⁶—, —R⁵—C(=O)—NR⁹—R⁵'—NR⁹'—C(=O)—R⁶—, —R⁵—NR⁹—, —R⁵—NR⁹—R⁶—, —R⁵—NR⁹—R⁵'—NR⁹'—R⁶—, —R⁵—C(=O)—NR⁹—R⁵'—NR⁹'—R⁶—, —R⁵—C(=O)—O—R⁶—, —C(=O)—O—R⁶—, —R⁵-phenyl-R⁶—, —R⁵-phenyl-, -phenyl-R⁶—, -phenyl-, wherein R⁵, R⁵' and R⁶ are independently from each other selected from C₁-C₁₂-alkyl or (—C₂H₄O—)₁₋₁₂, in particular C₁-C₆ alkyl, particularly C₁-C₃ alkyl, and wherein R⁹ and R⁹' are independently from each other selected from H, C₁₋₄-alkyl, —C₁₋₆-alkyl-NH₂, —C₁₋₆-alkyl-NHB, —C₁₋₆-alkyl-NB₂, —R¹⁵, —C₁₋₆-alkyl-R¹⁵, —C₁₋₆-alkyl-NH—R¹⁵, in particular from H and C₁₋₂-alkyl, more particularly R⁹ is H, wherein B is an independently selected acid labile amine protecting group, R¹⁵ is a blocking agent that is able to react with an aldehyde moiety, in particular R¹⁵ is selected from cysteinyl, threoninyl, 2-mercaptoethanol, cysteamine, ethandithiole, hydroxylamine, O-methylhydroxylamine, N-methylhydroxylamine, dithiothreitol, hydrazine, in particular cysteinyl and N-methylhydroxylamine, more particularly cysteinyl, wherein amine and/or thiol moieties of the blocking agent may be protected by an independently selected acid labile amine protecting group B, particularly Boc, and/or an acid labile thiol protecting group, particularly trityl, b is 0 or 1, in particular 1, V is an electron-withdrawing moiety selected from $-NR^{11}-C(=O)-$, $-C(=O)-NR^{11}-$, $-S(=O)-$, $-NR^{12}-$, -piperazinyl-, -pyridinyl, pyrimidinyl, pyrazinyl, pyridazinyl,

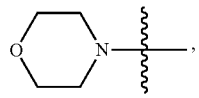

$-C(=O)-$, $-C(=O)-O-$, in particular $-NR^{11}-C(=O)-$, $-C(=O)-NR^{11}-$, $-S(=O)-$, $-NR^{12}-$, -piperazinyl-, -pyridinyl-, pyrimidinyl, more particularly from $-NH-C(=O)-$, $-C(=O)-NH-$, $-N-(CH_3)-$, -piperazinyl-, -pyridinyl-, pyrimidinyl, wherein $R^{11}$ is selected from H and $C_{1-4}$-alkyl, in particular from H and $C_{1-2}$-alkyl, more particularly $R^{11}$ is H, $R^{12}$ is selected from H and $C_{1-4}$-alkyl, in particular from H and $C_{1-2}$-alkyl, more particularly $R^{12}$ is methyl, a is 0 or 1, wherein the sum of a and b is 1 or 2, U is a phenyl or a five- or six-membered heteroaryl moiety, in particular a phenyl or a six-membered heteroaryl moiety, more particularly a phenyl, that is bound to at least one of the moieties V, $W_q$ and $E_n$, and that may optionally be substituted by $C_{1-6}$-alkyl, in particular $C_{1-3}$-alkyl, wherein V is defined as described above, W is selected from $-N_3$, $-S(=O)-R^8$, $-S-S-R^8$, $-O-CH_2-N_3$, $-O-C(=O)-O-CH_2-N_3$, $-N=N$-phenyl, $-N=N-R^8$,

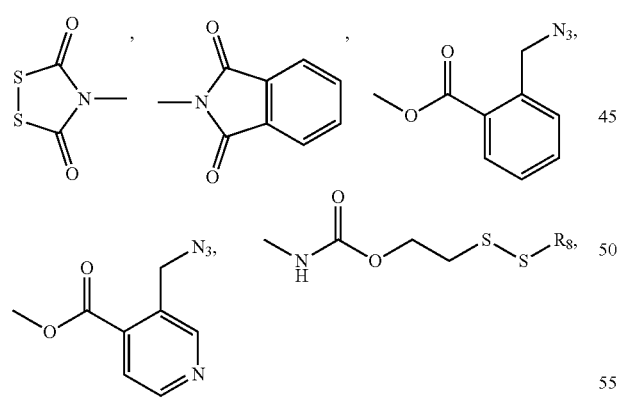

in particular $-N_3$, $-N=N-R^8$, $-O-CH_2-N_3$, $-S-S-R^8$, wherein $R^8$ is pyridyl, pyrimidinyl, pyrazinyl, pyridazyl, $-C_1-C_6$-alkyl or $-(CH_2)_p-NMe_2$, in particular pyridyl or $-C_1-C_6$-alkyl, with p being 1, 2, 3 or 4, E is an electron withdrawing group under acidic conditions, n being is an integer between 0 and 4, in particular 0 and 2, more particularly 0 or 1, and q is an integer between 0 and 4, in particular 0 and 2, more particularly 0 and 1, wherein the sum of n and q is equal or lower than 4, and wherein in case of U being a phenyl moiety and Y being $-(CH_2)_m-O-C(=O)-$, the sum of Hammett constants of V, W, E under acidic conditions is larger than 0.45, Y is $-(CH_2)_m-C(=O)-$ or $-(CH_2)_m-O-C(=O)-$ with m being 1, 2 or 3, in particular 1 or 2, more particularly 1, Z is an electron-withdrawing leaving group.

In certain embodiments,

X is selected from a moiety of formula 2, 2a, 3, 3a or 4, in particular of formula 2, 2a, 3 or 3a, more particularly of formula 2 or 2a,

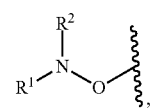

(2)

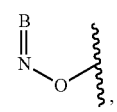

(2a)

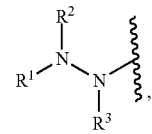

(3)

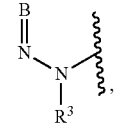

(3a)

(4)

wherein each $R^1$ and $R^2$ is independently from each other selected from H or B, wherein at least $R^1$ or $R^2$ is B, $R^3$ is selected from H or B, $R^4$ is selected from H, $C_1-C_{12}$-alkyl or aryl, wherein the aldehyde or keto group may be protected by an acid labile protecting group, B is an acid labile amine protecting group, T is a spacer selected from $-C_1-C_{12}$-alkyl-, in particular $C_{1-6}$-alkyl, more particularly $C_{1-3}$-alkyl, $-R^5-C(=O)-$, $-R^5-C(=O)-NR^9-R^6-$, $-R^5-C(=O)-NR^9-$, $-C(=O)-NR^9-R^6-$, $-R^5-NR^9-C(=O)-R^6-$, $-R^5-NR^9-R^{5'}-NR^{9'}C(=O)-R^6-$, $-R^5-C(=O)-NR^9-R^{5'}-NR^{9'}-C(=O)-$ $R^6$—, —$R^5$—C(=O)—O—$R^6$—, —C(=O)—O—$R^6$—, —$R^5$-phenyl-$R^6$—, —$R^5$-phenyl-, -phenyl-$R^6$—, -phenyl-, wherein
$R^5$, $R^{5'}$ and $R^6$ are independently from each other selected from $C_1$-$C_{12}$-alkyl, in particular $C_1$-$C_6$ alkyl, particularly $C_1$-$C_3$ alkyl, and wherein $R^9$ and $R^{9'}$ are independently from each other selected from H and $C_{1-4}$-alkyl, in particular from H and $C_{1-2}$-alkyl, more particularly $R^9$ is H,
b is 0 or 1, in particular 1,
V is an electron-withdrawing moiety selected from —$NR^{11}$—C(=O)—, —C(=O)—$NR^{11}$—, —S(=O)—, —$NR^{12}$—, -piperazinyl-, -pyridinyl, pyrimidinyl, pyrazinyl, pyridazinyl,

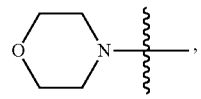

—C(=O)—, —C(=O)—O—, in particular —$NR^{11}$—C(=O)—, —C(=O)—$NR^{11}$—, S(=O)—, —$NR^{12}$—, -piperazinyl-, -pyridinyl-, pyrimidinyl, more particularly from —NH—C(=O)—, —C(=O)—NH—, —N—(CH$_3$)—, -piperazinyl-, -pyridinyl-, pyrimidinyl, wherein
$R^{11}$ is selected from H and $C_{1-4}$-alkyl, in particular from H and $C_{1-2}$-alkyl, more particularly $R^{11}$ is H,
$R^{12}$ is selected from H and $C_{1-4}$-alkyl, in particular from H and $C_{1-2}$-alkyl, more particularly $R^{12}$ is methyl,
a is 0 or 1, wherein the sum of a and b is 1 or 2,
U is a phenyl or a five- or six-membered heteroaryl moiety, in particular a phenyl or a six-membered heteroaryl moiety, more particularly a phenyl, that is bound to at least one of the moieties V, $W_q$ and $E_n$ and that may optionally be substituted by $C_{1-6}$-alkyl, in particular $C_{1-3}$-alkyl, wherein
V is defined as described above,
W is selected from —$N_3$, —S(=O)—$R^8$, —S—S—$R^8$, —O—CH$_2$—$N_3$, —O—C(=O)—O—CH$_2$—$N_3$, —N=N-phenyl, —N=N—$R^8$,

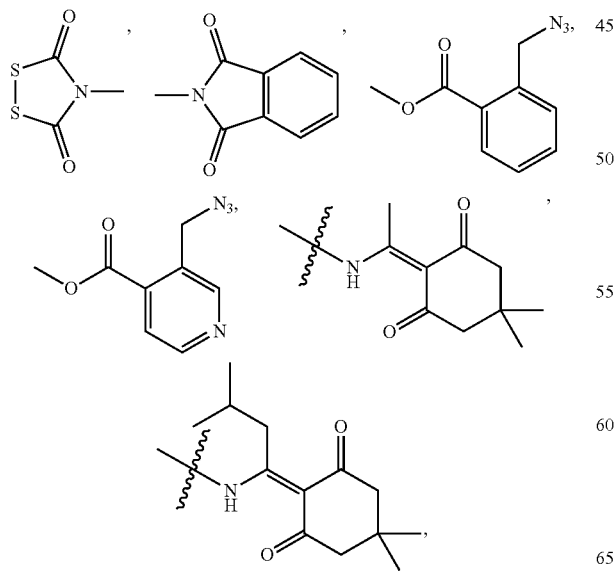

in particular —$N_3$, —N=N—$R^8$, —O—CH$_2$—$N_3$, —S—S—$R^8$, wherein
$R^8$ is pyridyl, pyrimidinyl, pyrazinyl, pyridazyl, —$C_1$-$C_6$-alkyl or —(CH$_2$)$_p$—NMe$_2$, in particular pyridyl or —$C_1$-$C_6$-alkyl, with p being 1, 2, 3 or 4,
E is an electron withdrawing group under acidic conditions,
n being is an integer between 0 and 4, in particular 0 and 2, more particularly 0 or 1, and q is an integer between 0 and 4, in particular 0 and 2, more particularly 0 and 1, wherein the sum of n and q is equal or lower than 4, and wherein
in case of U being a phenyl moiety and Y being —(CH$_2$)$_m$—O—C(=O)—, the sum of Hammett constants of V, W, E under acidic conditions is larger than 0.45, and wherein
in particular W is in ortho or para position in relation to Y,
Y is —(CH$_2$)$_m$—C(=O)— or —(CH$_2$)$_m$—O—C(=O)— with m being 1, 2 or 3, in particular 1 or 2, more particularly 1,
Z is an electron-withdrawing leaving group.
In certain embodiments,
X is selected from a moiety of formula 2, 2a, 3, 3a or 4, in particular of formula 2, 2a, 3 or 3a, more particularly of formula 2 or 2a, most particularly from 2,

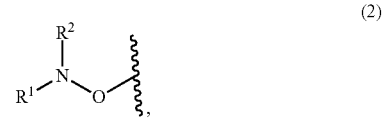

(2)

(2a)

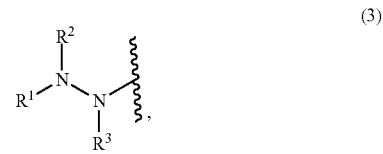

(3)

(3a)

(4)

wherein
each $R^1$ and $R^2$ is independently from each other selected from H or B, wherein at least $R^1$ or $R^2$ is B,
$R^3$ is selected from H or B,
$R^4$ is selected from H, $C_1$-$C_{12}$-alkyl or aryl, wherein the aldehyde or keto group may be protected by an acid labile protecting group,
B is an acid labile amine protecting group,
T is a spacer selected from
—$C_1$-$C_{12}$-alkyl-, in particular $C_{1-6}$-alkyl, more particularly $C_{1-3}$-alkyl, —$R^5$—C(=O)—$NR^9$—$R^6$—, —C(=O)—NR$^9$—R$^6$—, —R$^5$—NR$^9$—R$^5$—NR$^9$C(=O)—R$^6$—, —R$^5$—NR$^9$—C(=O)—R$^6$—, —R$^5$—C(=O)—O—R$^6$—, —C(=O)—O—R$^6$—, —R$^5$-phenyl-R$^6$—, —R$^5$-phenyl-, -phenyl-R$^6$—, -phenyl-, wherein R$^5$ and R$^6$ are independently from each other selected from C$_1$-C$_{12}$-alkyl, in particular C$_1$-C$_6$ alkyl, particularly C$_1$-C$_3$ alkyl, and wherein R$^9$ is selected from H and C$_{1-4}$-alkyl, in particular from H and C$_{1-2}$-alkyl, more particularly R$^9$ is H, b is 0 or 1, in particular 1, V is an electron-withdrawing moiety selected from —NR$^{11}$—C(=O)—, —C(=O)—NR$^{11}$—, —S(=O)—, —NR$^{12}$—, -pyridinyl, pyrimidinyl, pyrazinyl, pyridazyl, —C(=O)—, —C(=O)—O—, in particular —NR$^{11}$—C(=O)—, S(=O)—, —NR$^{12}$—, -pyridinyl-, pyrimidinyl, wherein R$^{11}$ is selected from H and C$_{1-4}$-alkyl, in particular from H and C$_{1-2}$-alkyl, more particularly R$^{11}$ is H, R$^{12}$ is selected from H and C$_{1-4}$-alkyl, in particular from H and C$_{1-2}$-alkyl, more particularly R$^{12}$ is methyl, a is 0 or 1, wherein the sum of a and b is 1 or 2, U is a phenyl or a five- or six-membered heteroaryl moiety, in particular a phenyl or a six-membered heteroaryl moiety, that is bound to at least one of the moieties V, W and E, wherein V is defined as described above, W is selected from —N$_3$, —S(=O)—R$^8$, —SSR$^8$, —OCH$_2$N$_3$, —OC(=O)OCH$_2$—N$_3$, —N=N-phenyl, —N=N-pyridine,

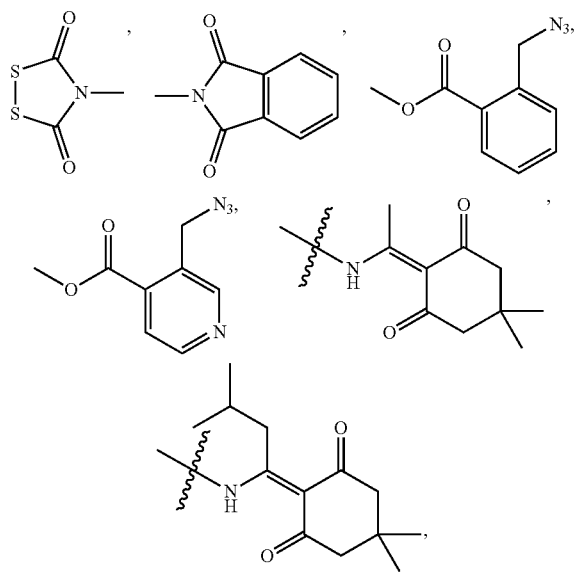

wherein

R$^8$ is pyridyl, pyrimidinyl, pyrazinyl, pyridazyl, —C$_1$-C$_6$-alkyl or —(CH$_2$)$_p$—NMe$_2$ with p being 1, 2, 3 or 4, E is selected from pyridyl, pyrimidinyl, pyrazinyl, pyridazyl, —F, —Cl, —Br, —I, —CN, —NO$_2$, —N$_3$, —CF$_3$, —SO$_3$H, —CO$_2$H, —C(=O)NH$_2$, —SO$_2$Me, —SOMe, —SO$_2$Et, —SOEt, in particular pyridyl, pyrimidinyl, pyrazinyl, pyridazyl, —F, —Cl, —Br, —I, —CN, —NO$_2$, —N$_3$, —CF$_3$, —SO$_3$H, —CO$_2$H, with R$^{13}$ being selected from —F, —Cl, —Br, —I, —PF$_6$, and wherein in case of U being a phenyl moiety and Y being —(CH$_2$)$_m$—O—C(=O)—, the sum of Hammett constants of V, W, E under acidic conditions is larger than 0.45, and wherein in particular W is in ortho or para position in relation to Y, Y is —(CH$_2$)$_m$—C(=O)— or —(CH$_2$)$_m$—O—C(=O)— with m being 1, 2 or 3, in particular 1 or 2, more particularly 1, Z is an electron-withdrawing leaving group.

The linker molecule of formula 1 is suitable for the purification of peptides after solid phase peptide synthesis (SPPS).

A common approach for purifying peptides after SPPS using a linker molecule is coupling the linker molecule to the N-terminus of the peptide in a final coupling step. In this coupling step, the N-terminus of the peptide will nucleophilically attack the linker molecule to form a covalent carbamate or amide bond with the moiety Y of the linker while the electron withdrawing leaving group Z is released. Subsequently, the peptide-linker-construct is cleaved off the synthesis resin by addition of TFA.

Linkers according to the invention are stable under acidic conditions when the peptide-linker construct is cleaved off, e.g. by using TFA.

The moiety X of the linker may be coupled to a functionalized solid phase such as a resin that is used during purification. The moiety X may form a hydrazone bond or oxime bond by reacting with a suitable moiety of the functionalized solid phase such as aldehyde, ketone, aminooxy or hydrazine.

The moiety T represents a spacer that is non-reactive under commonly applied purification conditions.

The moiety T is either directly bound to the moiety U or via the moiety V.

The moiety U contributes to the stability of the linker molecule under acidic conditions, particularly TFA>50%, in the presence of water pH<0. This is either achieved by using a heterocyclic moiety or a phenyl moiety that is bound to at least one of the electron-withdrawing moieties E, W and V.

If electron-withdrawing moieties (E, W, V) are attached to the phenyl moiety, the benzylic position of the linker molecule linked to the peptide gets less electron density and is thus less susceptible to acid catalyzed degradation. For sufficient stability of the inventive linker molecule under acidic conditions, a certain threshold of electron-withdrawal has to be met. This threshold is expressed as the sum of Hammett constants ($\sigma_m$ and $\sigma_p$) of V, W, E under acidic conditions being larger than 0.45. Hammett constants are calculated according to Hansch and Taft (1991), Chem. Rev. 91:165-195. A positive Hammett constant reflects the ability of the substituent to exert an electron withdrawing effect on the phenyl moiety and a negative value indicates that the substituent exerts an electron donating effect.

Hammett constants are empirically determined constants for substituents of the phenyl core in benzoic acid derivates in meta ($\sigma_m$) and para position ($\sigma_p$) resulting in different acidities (pKa). In the context of the present invention, the position is determined in relation to the binding of the moiety Y. For substituents in ortho position, Hammett values for the para position are a good approximation and therefore used in the context of the present invention to calculate the sum of Hammett values of the substituents V, W and E.

Of note, the Hammett constants are calculated for the substituents V, W and E under acidic conditions. For example, an amine moiety at neutral pH is characterized by the Hammett constants $\sigma_m=-0.16$ and $\sigma_p=-0.66$ and thus an electron-pushing substituent. Under acidic conditions, the amine moiety is protonated. For protonated amines, the Hammett constants are $\sigma_m=+0.86$ and $\sigma_p=+0.60$ indicating that protonated amines are electron-withdrawing substituents, this also includes aromatic amines which are able to withdraw electrons through a conjugated π-system from U in their protonated form whether directly as substituents on U or in π-conjugation of U.

The threshold of the sum of Hammett constants being larger than 0.45 applies for U being a phenyl moiety and Y being —$(CH_2)_m$—O—C(=O)— with m=1, since the —O—C(=O)— comprise a good leaving group in the benzylic position, facilitating the acid catalyzed degradation. Therefore electron-density in the aromatic ring should be low enough to prevent stabilization of cations in the benzylic position in Y.

TABLE 1

| substituent | $\sigma_m^{[a]}$ | $\sigma_p^{[a]}$ | substituent | $\sigma_m^{[a]}$ | $\sigma_p^{[a]}$ |
|---|---|---|---|---|---|
| —Br | 0.39 | 0.23 | —Cl | 0.37 | 0.23 |
| —$N_3$ | 0.37 | 0.08 | —$NO_2$ | 0.71 | 0.78 |
| —CONHMe | 0.35 | 0.36 | —N=$NC_6H_5$ | 0.32 | 0.39 |
| —SH | 0.25 | 0.15 | —$S^-$ | −0.36 | −1.21 |
| —OH | 0.12 | −0.35 | —$O^-$ | −0.47 | (−0.81) |
| —$NH_3^+$ | 0.86 | 0.60 | —$NH_2$ | −0.16 | −0.66 |
| —$NMe_3^{+[b]}$ | 0.88 | 0.82 | —$NMe_2$ | −0.16 | −0.83 |
| —$CH_2NH_3^+$ | 0.59 | 0.53 | —$CH_2NH_2$ | −0.03 | −0.11 |
| —$CH_2NMe_2H^+$ | 0.40 | 0.43 | —$CH_2NMe_2$ | 0.00 | 0.01 |
| —(4-pyrimidinyl) | 0.30 | 0.63 | —(4-pyridyl) | 0.27 | 0.44 |
| —SOMe | 0.52 | 0.49 | —SMe | 0.15 | 0.00 |
| —$SO_2Me$ | 0.60 | 0.72 | —SSMe | 0.22 | 0.00 |
| —$OCH_2CH_3$ | 0.10 | −0.24 | Et | −0.07 | −0.15 |

[a]$\sigma_m$ denotes Hammett values of substituents in meta position and $\sigma_p$ values of substituents in para position relative to the benzylic carbon, $\sigma_p$ are considered to be a good approximation for a-values for substituents in ortho position (all values from Hansch and Taft (1991), Chem. Rev. 91:165-195),
[b]—$NMe^{3+}$ is a good approximation for —$NMe_2H^+$ If the moiety Y is —$(CH_2)_m$—C(=O)—, this threshold is not necessary because —C(=O)— is not a good leaving group in the benzylic position.

For the stability of linker molecules under acidic conditions that comprise a heterocyclic moiety U, such extra threshold for the selection of specific moieties V, W and E is not necessary. As heterocyclic moieties per se are more electron-deficient compared to phenyl moieties, any combination of V, W and E appears to be sufficient for the stability of the linker molecule under acidic conditions. Especially when U is being a nitrogen containing heterocycle, the nitrogen will be protonated during acidic release of the peptide rendering the aromatic system of U especially low in electron density. Thus, not able to stabilize a benzylic cation.

Apart from mediating stability of a linker molecule under acidic conditions, the moieties V, W and E are important with regard to the release mechanism of the peptide. Furthermore, they may contribute to the solubility of the linker molecule under acidic conditions.

The moiety W is a reducible substituent that triggers the decay of the linker and thus the release of the peptide. A linker comprising a reduced moiety W is also referred to as reduced intermediate. In contrast to the stable linker molecule, the reduced intermediate is labile. The lability of the reduced intermediate is pH-dependent. If the moiety W is protonable, e.g. pyridyl, it also contributes to the solubility of the linker molecule under acidic conditions.

The moiety E is an electron-withdrawing substituent, which shows an electron-withdrawing effect under acidic conditions. For example, moieties that have a positive Hammett constant under acidic conditions are electron-withdrawing, particularly at pH 3 to 6, more particularly at pH 4.5. If the moiety E is protonable, it also contributes to the solubility of the linker molecule under acidic conditions.

In addition or alternatively to the moiety E, the moiety V may show an electron-withdrawing effect under acidic conditions. Also the moiety V may contribute to the stability and the solubility of the linker under acidic conditions.

Linker molecules according to the invention may release the peptide via an amine switch mechanism (see FIGS. 5, 6 and 7) or via a carbamate switch mechanism (see FIG. 8).

The moiety Y is either a —C(=O)— or a —O—C (=O)— moiety. Upon coupling of the linker molecule, an amide (—C(=O)—NH—) or a carbamate (—O—C (=O)—NH—) moiety is formed between the linker molecule and the N-terminus of the peptide. After purification, the peptides are released from the linker molecule and thus the purification media under reductive conditions either by 1.4 or 1.6 elimination or nucleophilic attack. The reductive stimulus transforms W into its reduced version, now functioning as an electron donating group and a nucleophile, thus enabling the release of the peptide.

In certain embodiments, X is selected from a moiety of formula 2 or 3.

In certain embodiments, X is selected from a moiety of formula 2.

The reaction time required for the coupling of the moiety X to a functionalized solid phase by formation of a hydrazone or oxime bond is longer when a linker with a moiety of formula 4 is used and shorter when a linker with a moiety of formula 2 or 3 is used. The formation of the hydrazone bond between an aldehyde or ketone moiety of a solid support and a moiety X of formula 3 is reversible. Due to this reversibility, the inventors observed up to approximately 10% loss of peptide material after each washing step during purification. In contrast to this, almost no loss of peptide material was observed when a linker with a moiety of formula 2 was used.

In certain embodiments, U is substituted by $C_{1-6}$-alkyl.
In certain embodiments, U is substituted by $C_{1-3}$-alkyl.
In certain embodiments, U is substituted by methyl.

If U is further substituted by one or more alkyl moieties, the Hammett values of the alkyl moieties are taken into consideration. In case of U being further substituted by a phenyl moiety or heteroatomic, the sum of Hammett values of V, W, E and the optional alkyl substituent is larger than 0.45. In certain embodiments, E is selected from piperidinyl, piperazinyl, pyridyl, pyrimidinyl, pyrazinyl, pyridazyl, —$N(C_2H_4)_2NH_2$, —$N(C_2H_4)_2N$—B, —N=N-phenyl, —N=N—$R^8$, —$(CH_2)_r$—NH—$C_{1-6}$-alkyl, —$(CH_2)_r$—N($C_{1-6}$-alkyl)$_2$—, —F, —Cl, —Br, —I, —CN, —$NO_2$, —$N_3$, —$CF_3$, —$SO_3H$, —$CO_2H$, —C(=O)$NH_2$, —$SO_2Me$, —SOMe, —$SO_2Et$, —SOEt with $R^8$ being pyridyl, pyrimidinyl, pyrazinyl, pyridazyl, —$C_1$-$C_6$-alkyl or —$(CH_2)_p$—$NMe_2$, in particular pyridyl or —$C_1$-$C_6$-alkyl, with p being 1, 2, 3 or 4, and B being an acid labile amine protecting group as defined herein, particularly —C(=O)OtBu (Boc) or C(=O) $CPh_3$, and r being 0, 1, 2, 3 or 4, particularly 0, 1 or 2. In certain embodiments, E is selected from piperidinyl, piperazinyl, pyridyl, pyrimidinyl, pyrazinyl, pyridazinyl, —$(CH_2)_r$—NH—$C_{1-6}$-alkyl, —$(CH_2)_r$—N($C_{1-6}$-alkyl)$_2$—, —N=N-phenyl, —N=N—$R^8$, —F, —Cl, —Br, —I, —CN, —$NO_2$, —$N_3$, —$CF_3$, —$SO_3H$, —$CO_2H$, wherein r is 0, 1, 2, 3 or 4, particularly 0, 1 or 2.

In certain embodiments, E is selected from piperidinyl, piperazinyl, pyridyl, pyrimidinyl, pyridazinyl —NH—$C_{1-6}$-alkyl, —N($C_{1-6}$-alkyl)$_2$—, —N=N-pyridinyl or —Br.

In certain embodiments, E is selected from piperidinyl, piperazinyl, pyridyl, pyrimidinyl, pyridazinyl —NH—$C_{1-6}$-alkyl, —N($C_{1-6}$-alkyl)$_2$—, or —Br.

In certain embodiments, E is selected from pyridyl, pyrimidinyl, pyridazinyl —NH—$C_{1-6}$-alkyl, —N($C_{1-6}$-alkyl)$_2$—, or —Br.

In certain embodiments, E is selected from pyridyl, pyrimidinyl, pyrazinyl, pyridazyl, —N=N-phenyl, —N=N—$R^8$, —F, —Cl, —Br, —I, —CN, —NO$_2$, —N$_3$, —CF$_3$, —SO$_3$H, —CO$_2$H, —C(=O)NH$_2$, —SO$_2$Me, —SOMe, —SO$_2$Et, —SOEt with $R^8$ being pyridyl, pyrimidinyl, pyrazinyl, pyridazyl, —$C_1$-$C_6$-alkyl or —(CH$_2$)$_p$—NMe$_2$, in particular pyridyl or —$C_1$-$C_6$-alkyl, with p being 1, 2, 3 or 4.

In certain embodiments, E is selected from pyridyl, pyrimidinyl, pyrazinyl, pyridazinyl, —N=N-phenyl, —N=N—$R^8$, —F, —Cl, —Br, —I, —CN, —NO$_2$, —N$_3$, —CF$_3$, —SO$_3$H, —CO$_2$H with $R^8$ being pyridyl, pyrimidinyl, pyrazinyl, pyridazyl, —$C_1$-$C_6$-alkyl or —(CH$_2$)$_p$—NMe$_2$, in particular pyridyl or —$C_1$-$C_6$-alkyl, with p being 1, 2, 3 or 4.

In certain embodiments, E is selected from piperidinyl, piperazinyl, pyridyl, pyrimidinyl, pyrazinyl, pyridazyl, —(CH$_2$)$_r$—NH—$C_{1-6}$-alkyl, —(CH$_2$)$_r$—N($C_{1-6}$-alkyl)$_2$—, particularly —(CH$_2$)$_r$—NH—$C_{1-3}$-alkyl, —(CH$_2$)$_r$—N($C_{1-3}$-alkyl)$_2$—, —F, —Cl, —Br, —I, —CN, —NO$_2$, —N$_3$, —CF$_3$, —SO$_3$H, —CO$_2$H, —C(=O)NH$_2$, —SO$_2$Me, —SOMe, —SO$_2$Et, —SOEt with r being 0, 1 or 2, particularly 0.

In certain embodiments, E is selected from pyridyl, pyrimidinyl, pyrazinyl, pyridazyl, —F, —Cl, —Br, —I, —CN, —NO$_2$, —N$_3$, —CF$_3$, —SO$_3$H, —CO$_2$H, —C(=O)NH$_2$, —SO$_2$Me, —SOMe, —SO$_2$Et, —SOEt.

In certain embodiments, E is selected from piperidinyl, piperazinyl, pyridyl, pyrimidinyl, pyrazinyl, pyridazinyl, —(CH$_2$)$_r$—NH—$C_{1-6}$alkyl, —(CH$_2$)$_r$—N($C_{1-6}$-alkyl)$_2$—, particularly —(CH$_2$)$_r$—NH—$C_{1-3}$alkyl, —(CH$_2$)$_r$—N($C_{1-3}$-alkyl)$_2$—, —F, —Cl, —Br, —I, —CN, —NO$_2$, —N$_3$, —CF$_3$, —SO$_3$H, —CO$_2$H.

In certain embodiments, E is selected from piperidinyl, piperazinyl, pyridyl, pyrimidinyl, pyrazinyl, pyridazinyl, —F, —Cl, —Br, —I, —CN, —NO$_2$, —N$_3$, —CF$_3$, —SO$_3$H, —CO$_2$H with r being 0, 1 or 2, particularly 0.

In certain embodiments, E is selected from pyridyl, pyrimidinyl, pyrazinyl, pyridazinyl, —F, —Cl, —Br, —I, —CN, —NO$_2$, —N$_3$, —CF$_3$, —SO$_3$H, —CO$_2$H.

In certain embodiments, E is selected from pyridyl, pyrimidinyl, pyridazinyl, —NH—$C_{1-6}$-alkyl, —N($C_{1-6}$-alkyl)$_2$—, particularly —NH—$C_{1-3}$-alkyl, —N($C_{1-3}$-alkyl)$_2$—, or —Br.

In certain embodiments, E is selected from pyridyl, pyrimidinyl, pyridazinyl or —Br.

In certain embodiments, n is 0, 1 or 2.

In certain embodiments, E is selected from pyridyl, pyrimidinyl, pyridazinyl and n is 1 or E is —Br and n is 1 or 2.

The peptide release via an amine switch (FIGS. 5, 6 and 7) requires a basic nitrogen that can be protonated. Such basic nitrogen may be provided by the moiety E.

In certain embodiments, E is selected from —(CH$_2$)$_r$—NH—$C_{1-6}$alkyl, —(CH$_2$)$_r$—N($C_{1-6}$-alkyl)$_2$—, particularly —(CH$_2$)$_r$—NH—$C_{1-3}$-alkyl, —(CH$_2$)$_r$—N($C_{1-3}$-alkyl)$_2$—, piperidinyl, piperazinyl, pyridyl, pyrimidinyl and pyridazinyl with r being 0, 1 or 2, particularly 0, wherein in particular n is 1.

In certain embodiments, E is selected from —(CH$_2$)$_r$—NH—$C_{1-6}$alkyl, —(CH$_2$)$_r$—N($C_{1-6}$-alkyl)$_2$—, particularly —(CH$_2$)$_r$—NH—$C_{1-3}$-alkyl, —(CH$_2$)$_r$—N($C_{1-3}$-alkyl)$_2$—, pyridyl, pyrimidinyl and pyridazinyl, r is 0, 1 or 2, particularly 0, and n is 1.

Particularly linker molecules that release the peptide by a carbamate switch (FIG. 8) comprise an electron withdrawing moiety that is not reduced by the reducing agents used for the reduction of the moiety W. Suitable substituents E for the carbamate switch may be non-protonable such as halogens or nitro substituents. Also substituents, which are characterized by a pKa of the corresponding acid <0 are suitable substituents E for the carbamate switch.

In certain embodiments, E is —F, —Cl, —Br, —I, —NO$_2$, —CF$_3$, —CN, —NC, BF$_2$, —PF$_4$, —OCF$_3$, —SOCF$_3$, —SOR$_8$, —SO$_2$R$_8$.

In certain embodiments, E is —Br.

In certain embodiments, E is —Br and n is 1 or 2.

If the solubility of the linker under acidic conditions shall be increased, e.g. for the purification of hydrophobic peptides, E may be selected from protonable moieties. In certain embodiments, E is selected from piperidinyl, piperazinyl, pyridyl, pyrimidinyl, pyrazinyl, pyridazyl, —N(C$_2$H$_4$)$_2$NH$_2$, —N(C$_2$H$_4$)$_2$N—B, —N=N—$R^8$, —(CH$_2$)$_r$—NH—$C_{1-6}$alkyl, —(CH$_2$)$_r$—N($C_{1-6}$-alkyl)$_2$—, —SO$_3$H, —CO$_2$H, —C(=O)NH$_2$, —SO$_2$Me, —SOMe, —SO$_2$Et, —SOEt with $R^8$ being selected from pyridyl, pyrimidinyl, pyrazinyl, pyridazyl, —(CH$_2$)$_p$—NMe$_2$, wherein p is 1, 2, 3 or 4, particularly 1 or 2.

In certain embodiments, B is selected from
Boc (—C(=O)OtBu), Eei (=CMeOEt, 1-ethoxyethylidene), trityl (—C(Ph)$_3$), —C(=O)CPh$_3$, Mmt (—C(Ph)$_2$C$_6$H$_4$OMe), DMT (—C(Ph)(C$_6$H$_4$OMe)$_2$), Cbz (—C(=O)OCH$_2$Ph), benzylideneamine (=CPh), phtalimides (=(CO)$_2$C$_6$H$_4$), p-toluenesulfonamides (—SO$_2$C$_6$H$_4$Me), benzylamine (—CH$_2$Ph), acetamides (—COMe), trifluoroacetamide (—COCF$_3$), Dde (1-(4,4-dimethyl-2,6-dioxocyclohex-1-ylidene)-3-ethyl) and 1-(4,4-dimethyl-2,6-dioxocyclohex-1-ylidene)-3-methylbutyl (ivDde), wherein particularly B is Boc or Eei, wherein more particularly B is Boc, or the
acetal- or ketal protecting groups are selected from

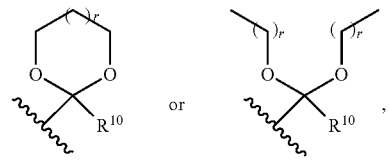

wherein r is 0 to 12, in particular 0 to 6, more particularly 0, 1 or 2, and $R^{10}$ is a —$C_1$-$C_{12}$-alkyl-, in particular $C_{1-6}$-alkyl, more particularly $C_{1-3}$-alkyl.

In certain embodiments, B is selected from
Boc (—C(=O)OtBu), Eei (=CMeOEt, 1-ethoxyethylidene), trityl (—C(Ph)$_3$), Mmt (—C(Ph)$_2$C$_6$H$_4$OMe), DMT (—C(Ph)(C$_6$H$_4$OMe)$_2$), Cbz (—C(=O)OCH$_2$Ph), benzylideneamine (=CPh), phtalimides (=(CO)$_2$C$_6$H$_4$), p-toluenesulfonamides (—SO$_2$C$_6$H$_4$Me), benzylamine (—CH$_2$Ph), acetamides (—COMe), trifluoroacetamide (—COCF$_3$), Dde (1-(4, 4-dimethyl-2,6-dioxocyclohex-1-ylidene)-3-ethyl) and 1-(4,4-dimethyl-2,6-dioxocyclohex-1-ylidene)-3-methylbutyl (ivDde), wherein particularly B is Boc or Eei, wherein more particularly B is Boc, or the acetal- or ketal protecting groups are selected from

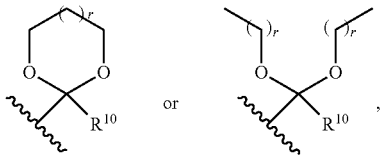

wherein r is 0 to 12, in particular 0 to 6, more particularly 0, 1 or 2, and $R^{10}$ is a —$C_1$-$C_{12}$-alkyl-, in particular $C_{1-6}$-alkyl, more particularly $C_{1-3}$-alkyl.

In certain embodiments, B is selected from Boc (—C(=O)OtBu), Eei (=CMeOEt, 1-ethoxyethylidene), trityl (—C(Ph)$_3$), Mmt (—C(Ph)$_2$C$_6$H$_4$OMe), DMT (—C(Ph)(C$_6$H$_4$OMe)$_2$), Cbz (—C(=O)OCH$_2$Ph), benzylideneamine (=CPh), phtalimides (=(CO)$_2$C$_6$H$_4$), p-toluenesulfonamides (—SO$_2$C$_6$H$_4$Me), benzylamine (—CH$_2$Ph), acetamides (—COMe), trifluoroacetamide (—COCF$_3$), Dde (1-(4,4-dimethyl-2,6-dioxocyclohex-1-ylidene)-3-ethyl) and 1-(4,4-dimethyl-2,6-dioxocyclohex-1-ylidene)-3-methylbutyl (ivDde).

In certain embodiment, B is Boc or Eei (=CMeOEt, 1-ethoxyethylidene).

In certain embodiment, B is Boc.

In certain embodiments, B is selected from acetal- or ketal protecting groups are selected from

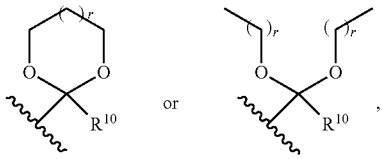

wherein r is 0 to 12, in particular 0 to 6, more particularly 0, 1 or 2, and $R^{10}$ is —$C_1$-$C_{12}$-alkyl-, in particular $C_{1-6}$-alkyl.

In certain embodiments, T is a linear or branched spacer comprising at least one of the moieties —$C_{1-12}$-alkyl-, (—$C_2H_4O$—)$_{1-12}$, —C(=O)—, —C(=O)-JR$^9$—, -JR$^9$—C(=O)—, -JR$^9$—, phenyl, 5- or 6-membered heteroaryl, wherein J is CH or N, in particular N, wherein $R^9$ is independently selected from H, $C_{1-4}$-alkyl, —$C_{1-6}$-alkyl-NH$_2$, —$C_{1-6}$-alkyl-NHB, —$C_{1-6}$-alkyl-NB$_2$, in particular from H and $C_{1-2}$-alkyl, more particularly $R^9$ is H, wherein B is an independently selected acid labile amine protecting group.

In certain embodiments, T is a linear or branched spacer, particularly a linear spacer, comprising 1 to 5 moieties independently selected from —$C_{1-12}$-alkyl-, (—$C_2H_4O$—)$_{1-12}$, —C(=O)—, —C(=O)-JR$^9$—, -JR$^9$—C(=O)—, -JR$^9$—, phenyl, 5- or 6-membered heteroaryl, In certain embodiments, T is a linear or branched spacer comprising at least one, particularly 1 to 5, of the moieties —$C_{1-12}$-alkyl-, —C(=O)—, —C(=O)—NR$^9$—, —NR$^9$—C(=O)—, —NR$^9$—, phenyl, piperazinyl, pyrroyl, pyrazoyl, imidazoyl, pyridinyl, pyrimidinyl, pyrazinyl and pyridazinyl, In certain embodiments, T is a linear or branched spacer comprising at least one, particularly 1 to 5, of the moieties —$C_{1-12}$-alkyl-, —C(=O)—, —C(=O)—NR$^9$—, —NR$^9$—C(=O)—, —NR$^9$—, phenyl, imidazoyl, pyridinyl, pyrimidinyl, pyrazinyl and pyridazinyl, In certain embodiments, T is a linear spacer.

In certain embodiments, T is a linear or branched spacer comprising at least one of the moieties —$C_{1-12}$-alkyl-, (—$C_2H_4O$—)$_{1-12}$, —C(=O)—, —C(=O)-JR$^9$—, -JR$^9$—C(=O)—, -JR$^9$—, wherein J is C or N, in particular N, wherein $R^9$ is independently selected from H, $C_{1-4}$-alkyl, —$C_{1-6}$-alkyl-NH$_2$, —$C_{1-6}$-alkyl-NHB, —$C_{1-6}$-alkyl-NB$_2$, in particular from H and $C_{1-2}$-alkyl, more particularly $R^9$ is H, wherein B is an independently selected acid labile amine protecting group.

In certain embodiments, the total length of the spacer T is between 0.5 and 100 nm.

In certain embodiments, T is selected from —$C_1$-$C_{12}$-alkyl-, in particular $C_{1-6}$-alkyl, more particularly $C_{1-3}$-alkyl, —$R^5$—C(=O)—, —$R^5$—C(=O)—NR$^9$—R$^6$—, —$R^5$—C(=O)—NR$^9$—, —C(=O)—NR$^9$—R$^6$—, —$R^5$—NR$^9$—C(=O)—R$^6$—, —$R^5$—NR$^9$—R$^{5'}$—NR$^{9'}$C(=O)—R$^6$—, —$R^5$—C(=O)—NR$^9$—R$^{5'}$—NR$^{9'}$—C(=O)—R$^6$—, —$R^5$—NR$^9$—, —$R^5$—NR$^9$—R$^6$—, —$R^5$—NR$^9$—R$^{5'}$—NR$^{9'}$—R$^6$—, —$R^5$—C(=O)—NR$^9$—R$^{5'}$—NR$^{9'}$—R$^6$—, —$R^5$—C(=O)—O—R$^6$—, —C(=O)—O—R$^6$—, —$R^5$-phenyl-R$^6$—, —$R^5$-phenyl-, -phenyl-R$^6$—, -phenyl-, —$R^5$-pyrroyl, —$R^5$-pyrazoyl, —$R^5$-imidazoyl, $R^5$-piperazinyl-, —$R^5$-pyridinyl, —$R^5$-pyrimidinyl, —$R^5$-pyrazinyl, —$R^5$-pyridazinyl, —$R^5$-pyrroyl-R$^6$—, —$R^5$-pyrazoyl-R$^6$—, —$R^5$-imidazoyl-R$^6$—, —$R^5$-piperazinyl-R$^6$—, —$R^5$-pyridinyl-R$^6$—, —$R^5$-pyrimidinyl-R$^6$—, —$R^5$-pyrazinyl-R$^6$—, —$R^5$-pyridazinyl-R$^6$—, pyrroyl-R$^6$—, pyrazoyl-R$^6$—, imidazoyl-R$^6$-piparazinyl-R$^6$—, pyridinyl-R$^6$—, pyrimidinyl-R$^6$—, pyrazinyl-R$^6$—, pyridazinyl-R$^6$—, pyrroyl, pyrazoyl, imidazoyl, piperazinyl, pyridinyl, pyrimidinyl, pyrazinyl and pyridazinyl.

In certain embodiments, T is selected from —$C_1$-$C_{12}$-alkyl-, in particular $C_{1-6}$-alkyl, more particularly $C_{1-3}$-alkyl, —$R^5$—C(=O)—, —$R^5$—C(=O)—NR$^9$—R$^6$—, —$R^5$—C(=O)—NR$^9$—, —C(=O)—NR$^9$—R$^6$—, —$R^5$—NR$^9$—C(=O)—R$^6$—, —$R^5$—NR$^9$—R$^{5'}$—NR$^{9'}$C(=O)—R$^6$—, —$R^5$—C(=O)—NR$^9$—R$^{5'}$—NR$^{9'}$—C(=O)—R$^6$—, —$R^5$—NR$^9$—, —$R^5$—NR$^9$—R$^6$—, —$R^5$—NR$^9$—R$^{5'}$—NR$^{9'}$—R$^6$—, —$R^5$—C(=O)—NR$^9$—R$^{5'}$—NR$^{9'}$—R$^6$—, —$R^5$—C(=O)—O—R$^6$—, —C(=O)—O—R$^6$—, —$R^5$-phenyl-R$^6$—, —$R^5$-phenyl-, -phenyl-R$^6$—, -phenyl-, —$R^5$-imidazoyl, —, —$R^5$-imidazoyl-R$^6$—, imidazoyl-R$^6$—, imidazoyl.

In certain embodiments, T is selected from —$C_1$-$C_{12}$-alkyl-, in particular $C_{1-6}$-alkyl, more particularly $C_{1-3}$-alkyl, —$R^5$—C(=O)—, —$R^5$—C(=O)—NR$^9$—R$^6$—, —$R^5$—C(=O)—NR$^9$—, —C(=O)—NR$^9$—R$^6$—, —$R^5$—NR$^9$—C(=O)—R$^6$—, —$R^5$—NR$^9$—R$^{5'}$—NR$^{9'}$—C(=O)—R$^6$—, —$R^5$—C(=O)—NR$^9$—R$^{5'}$—NR$^{9'}$—C(=O)—R$^6$—, —$R^5$—NR$^9$—, —$R^5$—NR$^9$—R$^6$—, —$R^5$—NR$^9$—R$^{5'}$—NR$^{9'}$—R$^6$—, —$R^5$—C(=O)—NR$^9$—R$^{5'}$—NR$^{9'}$—R$^6$—, —$R^5$—C(=O)—O—R$^6$—, —C(=O)—O—R$^6$—, —$R^5$-imidazoyl, —, —$R^5$-imidazoyl-R$^6$—, imidazoyl-R$^6$—, imidazoyl.

In certain embodiments, T is selected from —$C_1$-$C_{12}$-alkyl-, in particular $C_{1-6}$-alkyl, more particularly $C_{1-3}$-alkyl, —$R^5$—C(=O)—, —$R^5$—C(=O)—NR$^9$—R$^6$—, —$R^5$—C(=O)—NR$^9$—, —C(=O)—NR$^9$—R$^6$—, —$R^5$—NR$^9$—C(=O)—R$^6$—, —$R^5$—NR$^9$—R$^{5'}$—NR$^{9'}$—C(=O)—R$^6$—, —$R^5$—C(=O)—NR$^9$—R$^{5'}$—NR$^{9'}$—C(=O)—R$^6$—, —$R^5$—NR$^9$—, —$R^5$—NR$^9$—R$^6$—, —$R^5$—NR$^9$—R$^{5'}$—

NR$^{9'}$—R$^6$—, —R$^5$—C(=O)—NR$^9$—R$^{5'}$—NR$^{9'}$—R$^6$—, —R$^5$—C(=O)—O—R$^6$—, —C(=O)—O—R$^6$—.

In certain embodiments, T is selected from —C$_1$-C$_{12}$-alkyl-, in particular C$_{1-6}$-alkyl, more particularly C$_{1-3}$-alkyl, —R$^5$—C(=O)—, —R$^5$—C(=O)—NR$^9$—, —R$^5$—NR$^9$—C(=O)—R$^6$—, —R$^5$—C(=O)—NR$^9$—R$^6$—, —R$^5$—C(=O)—NR$^9$—R$^{5'}$—NR$^{9'}$C(=O)—R$^6$—, in particular C$_{1-3}$-alkyl, —R$^5$—C(=O)—NR$^9$—, —R$^5$—NR$^9$—C(=O)—R$^6$—, more particularly C$_{1-3}$-alkyl or —R$^5$—C(=O)—NR$^9$—, with R$^5$, R$^{5*}$, R$^6$, R$^{9'}$ and R$^9$ being as defined above.

In certain embodiments, T is a linear or branched spacer comprising at least one, particularly 1 to 5, of the moieties —C$_{1-12}$-alkyl-, —C(=O)—, —C(=O)—NR$^9$—, —NR$^9$—C(=O)—, —NR$^9$—, phenyl, 5- to 6-membered heteroaryl, wherein R$^9$ is independently selected from H, C$_{1-4}$-alkyl, —C$_{1-6}$-alkyl-NH$_2$, —C$_{1-6}$-alkyl-NHB, —C$_{1-6}$-alkyl-NB$_2$, —R$^{15}$, —C$_{1-6}$alkyl-R$^{15}$, —C$_{1-6}$-alkyl-NH—R$^{15}$, in particular from H and C$_{1-2}$-alkyl, more particularly R$^9$ is H, wherein B is an independently selected acid labile amine protecting group, wherein R$^{15}$ is a blocking agent that is able to react with an aldehyde moiety, in particular R$^{15}$ is selected from cysteinyl, threoninyl, 2-mercaptoethanol, cysteamine, ethandithiole, hydroxylamine, O-methylhydroxylamine, N-methylhydroxylamine, dithiothreitol, hydrazine, in particular cysteinyl and N-methylhydroxylamine, more particularly cysteinyl, wherein
   amine and/or thiol moieties of the blocking agent may be protected by an independently selected acid labile amine protecting group B, particularly Boc, and/or an acid labile thiol protecting group, particularly trityl.

In certain embodiments, T is a linear or branched spacer comprising at least one, particularly 1 to 5, of the moieties —C$_{1-12}$-alkyl-, —C(=O)—, —C(=O)—NR$^9$—, —NR$^9$—C(=O)—, —NR$^9$—, phenyl, pyrroyl, pyrazoyl, imidazoyl, piperazinyl, pyridinyl, pyrimidinyl, pyrazinyl and pyridazinyl, In certain embodiments, T is a linear or branched spacer comprising at least one, particularly 1 to 5, of the moieties —C$_{1-12}$-alkyl-, —C(=O)—, —C(=O)—NR$^9$—, —NR$^9$—C(=O)—, —NR$^9$—, phenyl, imidazoyl, pyridinyl, pyrimidinyl, pyrazinyl and pyridazinyl, In certain embodiments, T is a linear or branched spacer comprising at least one of the moieties —C$_{1-12}$-alkyl-, —C(=O)—, —C(=O)—NR$^9$—, —NR$^9$—C(=O)—, —NR$^9$—, wherein R$^9$ is independently selected from H, C$_{1-4}$-alkyl, —C$_{1-6}$alkyl-NH$_2$, —C$_{1-6}$-alkyl-NHB, —C$_{1-6}$-alkyl-NB$_2$, —R$^{15}$, —C$_{1-6}$alkyl-R$^{15}$, —C$_{1-6}$-alkyl-NH—R$^{15}$, in particular from H and C$_{1-2}$-alkyl, more particularly R$^9$ is H, wherein B is an independently selected acid labile amine protecting group, R$^{15}$ is a blocking agent that is able to react with an aldehyde moiety, in particular R$^{15}$ is selected from cysteinyl, threoninyl, 2-mercaptoethanol, cysteamine, ethandithiole, hydroxylamine, O-methylhydroxylamine, N-methylhydroxylamine, dithiothreitol, hydrazine, in particular cysteinyl and N-methylhydroxylamine, more particularly cysteinyl, wherein
   amine and/or thiol moieties of the blocking agent may be protected by an independently selected acid labile amine protecting group B, particularly Boc, and/or an acid labile thiol protecting group, particularly trityl.

As described above, the spacer T is generally non-reactive under commonly applied purification conditions with the exception of the removal of protecting groups under acidic conditions. The spacer T may enhance the solubility of the linker molecule. In particular branched spacers that comprise a protected or unprotected amine moiety at R$^9$ contribute to an enhanced solubility. Under acidic conditions, the amine protection group B is removed and the amine is protonated.

In certain embodiments, T is a linear or branched spacer comprising at least one of the moieties —C$_{1-12}$-alkyl-, —C(=O)—, —C(=O)—NR$^9$—, —NR$^9$—C(=O)—, —NR$^9$—, wherein R$^9$ is independently selected from H, C$_{1-4}$-alkyl, —C$_{1-6}$-alkyl-NH$_2$, —C$_{1-6}$-alkyl-NHB, —C$_{1-6}$-alkyl-NB$_2$, in particular from H and C$_{1-2}$-alkyl, more particularly R$^9$ is H, wherein B is an independently selected acid labile amine protecting group.

The spacer T may also comprise a blocking function. In particular a branched spacer may comprise a blocking agent that is suitable to bind to aldehyde moieties. When the solid phase used for peptide purification comprises aldehyde moieties, e.g. agarose beads, the moiety X of the linker compound may be covalently bound to the solid phase, e.g by formation of a oxime bond. Non-reacted aldehyde moieties may cause unwanted side reactions during subsequent purification. To prevent such side reactions, the non-reacted aldehyde moieties of the solid phase can be blocked by the blocking function of the spacer, e.g. a cysteinyl moiety.

In certain embodiments, T is a linear or branched spacer comprising at least one of the moieties —C$_{1-12}$-alkyl-, —C(=O)—, —C(=O)—NR$^9$—, —NR$^9$—C(=O)—, —NR$^9$—, wherein R$^9$ is independently selected from H, C$_{1-4}$-alkyl, —R$^{15}$, —C$_{1-6}$-alkyl-R$^{15}$, —C$_{1-6}$-alkyl-NH—R$^{15}$, in particular from H and C$_{1-2}$-alkyl, more particularly R$^9$ is H, wherein B is an independently selected acid labile amine protecting group,
   R$^{15}$ is a blocking agent that is able to react with an aldehyde moiety, in particular R$^{15}$ is selected from cysteinyl, threoninyl, 2-mercaptoethanol, cysteamine, ethandithiole, hydroxylamine, O-methylhydroxylamine, N-methylhydroxylamine, dithiothreitol, hydrazine, in particular cysteinyl and N-methylhydroxylamine, more particularly cysteinyl, wherein
   amine and/or thiol moieties of the blocking agent may be protected by an independently selected acid labile amine protecting group B, particularly Boc, and/or an acid labile thiol protecting group, particularly trityl.

In certain embodiments, T is selected from —C$_1$-C$_{12}$-alkyl-, in particular C$_{1-6}$-alkyl, more particularly C$_{1-3}$-alkyl, —R$^5$—C(=O)—NR$^9$—R$^6$—, —C(=O)—NR$^9$—R$^6$—, —R$^5$—NR$^9$—C(=O)—R$^6$—, —R$^5$—C(=O)—O—R$^6$—, —C(=O)—O—R$^6$—, —R$^5$—NR$^9$—R$^5$—NR$^9$C(=O)—R$^6$—, particularly from —C$_1$-C$_{12}$-alkyl-, in particular C$_{1-6}$-alkyl, more particularly C$_{1-3}$-alkyl, —R$^5$—NR$^9$—C(=O)—R$^6$—, —R$^5$—C(=O)—NR$^9$—R$^6$—, —R$^5$—NR$^9$—R$^5$—NR$^9$C(=O)—R$^6$—, most particularly —R$^5$—NR$^9$—C(=O)—R$^6$—, with R$^5$, R$^6$ and R$^9$ being as defined above.

As described above, the moieties U, V, W and E contribute to the stability of the linker under acidic conditions. For example, linkers comprising a moiety U or V that comprises an amine or a heterocycle such as pyridine are stable under acidic conditions, particularly TFA>50%, in the presence of water pH<0, as the amine or heterocycle is protonated. Furthermore, the protonated linker improves the solubility of the linker-peptide complex. If the pH is higher than the pKa of the linker, the linker will rapidly decompose during the desired release of the peptide as the last step.

In certain embodiments, V is an electron-withdrawing moiety selected from —NR$^{11}$—C(=O)—, —C(=O)—NR$^{11}$—, —S(=O)—, —NR$^{12}$—(CH$_2$)$_p$—, -piperazinyl-(CH$_2$)$_p$—, -pyridinyl, pyrimidinyl, pyrazinyl, pyridazinyl,

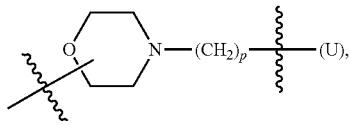

—C(=O)—, —C(=O)—O—, wherein
  $R^{11}$ is selected from H and $C_{1-4}$-alkyl, in particular from H and $C_{1-2}$-alkyl, more particularly $R^{11}$ is H,
  $R^{12}$ is selected from H and $C_{1-4}$-alkyl, in particular from H and $C_{1-2}$-alkyl, more particularly $R^{12}$ is methyl,
  p is 0, 1 or 2, particularly 0 or 1.

In certain embodiments, V is an electron-withdrawing moiety selected from —NR$^{11}$—C(=O)—, —C(=O)—NR$^{11}$—, —S(=O)—, —NR$^{12}$—(CH$_2$)$_p$—, -piperazinyl-(CH$_2$)$_p$—, -pyridinyl, pyrimidinyl, pyrazinyl, pyridazinyl,

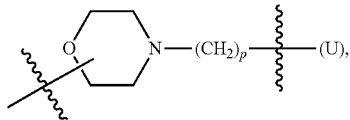

—C(=O)—, —C(=O)—O—, wherein the pyridinyl moiety is connected to U at position 3.

In certain embodiments, V is selected from —NR$^{11}$—C(=O)—, —C(=O)—NR$^{11}$—, —S(=O)—, —NR$^{12}$—(CH$_2$)$_p$—, -piperazinyl-(CH$_2$)$_p$—.

In certain embodiments, V is selected from —NR$^{11}$—C(=O)—, —C(=O)—NR$^{11}$—, —NR$^{12}$—(CH$_2$)$_p$—, -piperazinyl-(CH$_2$)$_p$—.

In certain embodiments, V is selected from —NH—C(=O)—, —C(=O)—NH—, —N—(CH$_3$)—, —NH—, -piperazinyl-(CH$_2$)$_p$—.

In certain embodiments, V is selected from —NH—C(=O)—, —C(=O)—NH—, —N—(CH$_3$)—, -piperazinyl-(CH$_2$)$_p$—.

In certain embodiments, V is selected from —NH—C(=O)—, —C(=O)—NH—, —N—(CH$_3$)—, -piperazinyl-(CH$_2$)$_p$— with p being 0 or 1.

In certain embodiments, V is selected from —NH—C(=O)—, —C(=O)—NH— and -piperazinyl-(CH$_2$)$_p$— with p being 0 or 1, particularly p being 0.

Particularly linker molecules that release the peptide via a carbamate switch (FIG. 8) do not comprise a basic nitrogen atom, wherein such atom has a pKa of the corresponding acid below 2. In certain embodiments, V is selected from —NR$^{11}$—C(=O)—, —C(=O)—NR$^{11}$— and —S(=O)—, particularly form —NH—C(=O)— and —C(O=)—NH—, more particularly V is —NH—C(=O)—.

V is an electron-withdrawing moiety selected from —NR$^{11}$—C(=O)—, —C(=O)—NR$^{11}$—, —S(=O)—, —NR$^{12}$—, -piperazinyl-, -pyridinyl, pyrimidinyl, pyrazinyl, pyridazinyl,

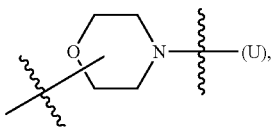

—C(=O)—, —C(=O)—O—, wherein R$^{11}$ is selected from H and $C_{1-4}$-alkyl, in particular from H and $C_{1-2}$-alkyl, more particularly R$^{11}$ is H, R$^{12}$ is selected from H and $C_{1-4}$-alkyl, in particular from H and $C_{1-2}$-alkyl, more particularly R$^{12}$ is methyl.

V is an electron-withdrawing moiety selected from —NR$^{11}$—C(=O)—, —C(=O)—NR$^{11}$—, —S(=O)—, —NR$^{12}$—, -piperazinyl-, -pyridinyl, pyrimidinyl, pyrazinyl, pyridazinyl, —C(=O)—, —C(=O)—O—, wherein R$^{11}$ is selected from H and $C_{1-4}$-alkyl, in particular from H and $C_{1-2}$-alkyl, more particularly R$^{11}$ is H, R$^{12}$ is selected from H and $C_{1-4}$-alkyl, in particular from H and $C_{1-2}$-alkyl, more particularly R$^{12}$ is methyl.

V is an electron-withdrawing moiety selected from —NR$^{11}$—C(=O)—, —C(=O)—NR$^{11}$—, —S(=O)—, —NR$^{12}$—, -piperazinyl-, -pyridinyl-, pyrimidinyl, wherein R$^{11}$ is selected from H and $C_{1-4}$-alkyl, in particular from H and $C_{1-2}$-alkyl, more particularly R$^{11}$ is H, R$^{12}$ is selected from H and $C_{1-4}$-alkyl, in particular from H and $C_{1-2}$-alkyl, more particularly R$^{12}$ is methyl.

V is an electron-withdrawing moiety selected from —NR$^{11}$—C(=O)—, —C(=O)—NR$^{11}$—, —NR$^{12}$—, -piperazinyl-, -pyridinyl-, pyrimidinyl, wherein R$^{11}$ is selected from H and $C_{1-4}$-alkyl, in particular from H and $C_{1-2}$-alkyl, more particularly R$^{11}$ is H, R$^{12}$ is selected from H and $C_{1-4}$-alkyl, in particular from H and $C_{1-2}$-alkyl, more particularly R$^{12}$ is methyl.

V is an electron-withdrawing moiety selected from —NH—C(=O)—, —C(=O)—HN—, —N—(CH$_3$)—, -piperazinyl-, -pyridinyl-, pyrimidinyl, pyrazinyl, pyridazinyl.

V is an electron-withdrawing moiety selected from —NH—C(=O)—, —C(=O)—HN—, —N—(CH$_3$)—, -piperazinyl-, -pyridinyl-, pyrimidinyl.

In certain embodiments, V is an electron-withdrawing moiety selected from —NR$^{11}$—C(=O)—, —C(=O)—NR$^{11}$—, —S(=O)—, —NR$^{12}$—, -pyridinyl, pyrimidinyl, pyrazinyl, pyridazyl, —C(=O)—, —C(=O)—O—.

In certain embodiments, V is selected from —NR$^{11}$—C(=O)—, —C(=O)—NR$^{11}$—, —S(=O)—, —NR$^{12}$— and -pyridinyl-, pyrimidinyl, wherein R$^{11}$ is selected from H and $C_{1-4}$-alkyl, in particular from H and $C_{1-2}$-alkyl, more particularly R$^{11}$ is H, and R$^{12}$ is selected from H and $C_{1-4}$-alkyl, in particular from H and $C_{1-2}$-alkyl, more particularly R$^{12}$ is methyl.

In certain embodiments, V is selected from —NR$^{11}$—C(=O)—, S(=O)—, —NR$^{12}$—, -pyridinyl-, pyrimidinyl, wherein R$^{11}$ is selected from H and $C_{1-4}$-alkyl, and R$^{12}$ is selected from H and $C_{1-4}$-alkyl.

In certain embodiments, V is selected from —NR$^{11}$—C(=O)—, S(=O)—, —NR$^{12}$—, -pyridinyl-, pyrimidinyl, wherein R$^{11}$ is selected from H and $C_{1-2}$-alkyl, and R$^{12}$ is selected from H and $C_{1-2}$-alkyl.

In certain embodiments, V is selected from —NH—C(=O)—, —N—(CH$_3$)—, -pyridinyl-, pyrimidinyl.

Particularly linker molecules that release the peptide via an amine switch require a basic nitrogen atom. The basic nitrogen atom may be provided via the moiety V, E or U (U=heteroaryl). If U is a phenyl, the basic nitrogen atom may be provided via the moiety V or E.

In certain embodiments, E and V are selected as described above, wherein in case of U being a phenyl, at least one moiety E or V is selected from
  E: piperidinyl, piperazinyl, pyridyl, pyrimidinyl, pyrazinyl, pyridazyl, —N(C$_2$H$_4$)$_2$NH$_2$, —N(C$_2$H$_4$)$_2$N—B, =N—R$^8$, —(CH$_2$)$_r$—NH—C$_{1-6}$-alkyl, —(CH$_2$)$_r$—N(C$_{1-6}$alkyl)$_2$—, —N$_3$, —SO$_3$H, —CO$_2$H, —C(=O)

NH$_2$, —SO$_2$Me, —SOMe, —SO$_2$Et, —SOEt with R$^8$ being selected from pyridyl, pyrimidinyl, pyrazinyl, pyridazyl, —(CH$_2$)$_p$—NMe$_2$, p and B being defined as described herein, and V: —NR$^{12}$—(CH$_2$)$_p$—, -piperazinyl-(CH$_2$)$_p$—, -pyridinyl, pyrimidinyl, pyrazinyl, pyridazinyl,

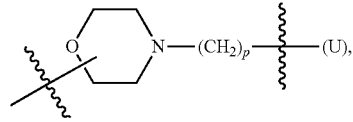

in particular —NR$^{12}$—(CH$_2$)$_p$—, -piperazinyl-(CH$_2$)$_p$—, -pyridinyl-, pyrimidinyl, with R$^{12}$ and p being defined as described herein.

As described above, W is a reducible moiety. Upon reduction of W, the reduced intermediate further decays in a pH-dependent manner to release the peptide with a free N-terminus.

In certain embodiments, W is selected from —N$_3$, —NO$_2$, —S(=O)—R$^8$, —S—S—R$^8$, —O—CH$_2$—N$_3$, —O—C(=O)—O—CH$_2$—N$_3$, —N=N-phenyl, —=N—R$^8$,

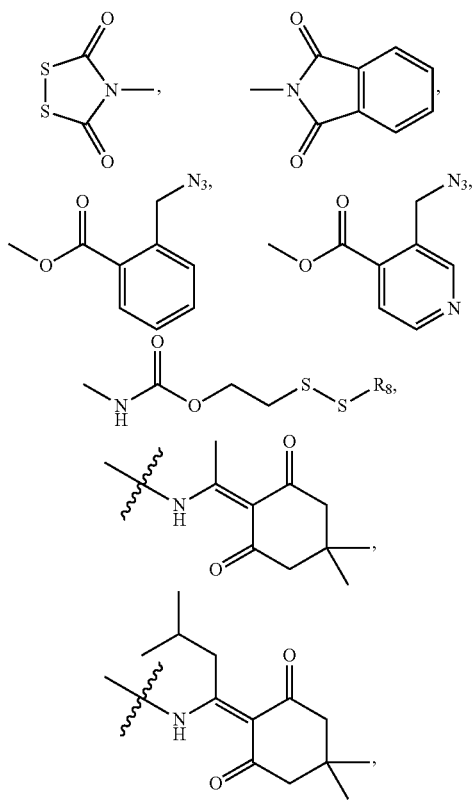

wherein
R$^8$ is pyridyl, pyrimidinyl, pyrazinyl, pyridazyl, —C$_1$-C$_6$-alkyl or —(CH$_2$)$_p$—NMe$_2$, in particular pyridyl or —C$_1$-C$_6$-alkyl, with p being 1, 2, 3 or 4. The C$_{1-6}$-alkyl may be linear or branched, e.g. butyl or tertbutyl.

In certain embodiments, W is selected from —N$_3$, —NO$_2$, —S(=O)—R$^8$, —S—S—R$^8$, —O—CH$_2$—N$_3$, —O—C(=O)—O—CH$_2$—N$_3$, —N=N-phenyl, —=N—R$^8$,

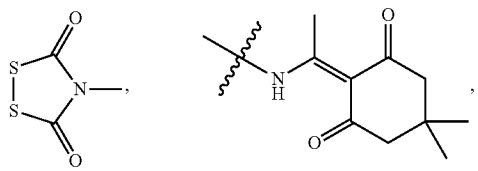

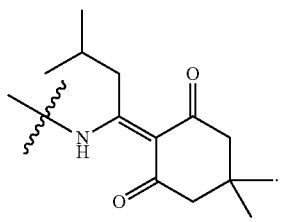

In certain embodiments, W is selected from —N$_3$, —S(=O)—R$^8$, —S—S—R$^8$, —O—CH$_2$—N$_3$, —=N—R$^8$, in particular —N$_3$, —=N—R$^8$, —O—CH$_2$—N$_3$, —S—S—R$^8$, wherein R$^8$ is pyridyl, pyrimidinyl, pyrazinyl, pyridazyl, —C$_1$-C$_6$-alkyl or —(CH$_2$)$_p$—NMe$_2$, in particular pyridyl or —C$_1$-C$_6$-alkyl, with p being 1, 2, 3 or 4.

In certain embodiments, W is selected from —N$_3$, —S(=O)—R$^8$, —S—S—R$^8$, —O—CH$_2$—N$_3$, —=N—R$^8$, in particular —N$_3$, —=N—R$^8$, —O—CH$_2$—N$_3$, —S—S—R$^8$, wherein R$^8$ is pyridyl, pyrimidinyl, pyrazinyl, pyridazyl, —C$_1$-C$_6$-alkyl or —(CH$_2$)$_p$—NMe$_2$, in particular pyridyl or —C$_1$-C$_6$-alkyl, with p being 1, 2, 3 or 4.

In case R$^8$ is a C$_{1-6}$alkyl, the alkyl moiety may be linear or branched, e.g. tert-butyl. In particular in case of W being —S—S—R$^8$, R$^8$ may be pyridyl or —C$_1$-C$_4$-alkyl, particularly pyridyl or tert-butyl.

Linkers that comprise a moiety W=—S—S—R$^8$ may be cleaved with thiols. Therefore, the cleavage of the peptide-linker complex from the synthesis resin used during SPPS under acidic conditions (e.g. TFA>50%, in the presence of water pH<0) may be performed without thiols when such linkers are used for peptide purification.

In certain embodiments, W is selected from —N$_3$, —S(=O)—R$^8$, —S—S—R$^8$, —O—CH$_2$—N$_3$, —=N—R$^8$, in particular —N$_3$, —=N—R$^8$, —O—CH$_2$—N$_3$, —S—S—R$^8$, wherein R$^8$ is pyridyl, pyrimidinyl, pyrazinyl, pyridazyl or —C$_1$-C$_6$-alkyl or, in particular pyrimidinyl, pyridyl or —C$_1$-C$_6$-alkyl, more particularly pyridyl or —C$_1$-C$_6$-alkyl.

In certain embodiments, W is selected from —N$_3$, —S—S—R$^8$ with R$^8$ being —C$_1$-C$_6$-alkyl and —NO$_2$.

Linker molecules that release the peptide via an amine switch with an azide reductive safety lock (FIG. 5) or by a carbamate switch (FIG. 8) comprise a reducible moiety —N$_3$. In certain embodiments, W is —N$_3$.

Linker molecules that release the peptide via an amine switch with a reductive safety lock without azide (FIG. 6) comprise a reducible moiety such as —NO$_2$ or —S—S-tertbutyl. In certain embodiments, W is selected from —S—S—R$^8$ with R$^8$ being —C$_1$-C$_6$-alkyl, —NO$_2$,

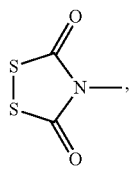 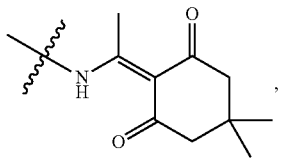

—N═N—R$^8$ with R$^8$ being pyridyl, pyrimidinyl, pyrazinyl or pyridazyl,

In certain embodiments, W is selected from —S—S—R$^8$ with R$^8$ being —C$_1$-C$_6$-alkyl, —NO$_2$, —N═N—R$^8$ with R$^8$ being pyridyl, pyrimidinyl, pyrazinyl or pyridazyl, particularly —NO$_2$ or —S—S—R$^8$ with R$^8$ being —C$_1$-C$_6$-alkyl.

Linker molecules that release the peptide via an amine switch with nucleophilic release (FIG. 7) comprise a reducible moiety such as —N$_3$, —S—S—R$^8$ with R$^8$ being a C$_{1-6}$-alkyl, in particular tertbutyl or R$^8$ being pyridinyl.

As described above, a linker molecule may contribute to the solubility of the linker-peptide construct under acidic conditions, particularly during purification of hydrophobic peptides. Solubility may also be mediated by the moiety W, i.e. W is selected from a group that introduces enhanced solubility towards the peptide that is going to be purified in a pH range of 0-7.

In certain embodiments, W is selected from —S(═O)—R$^8$, —S—S—R$^8$, ═N—R$^8$,

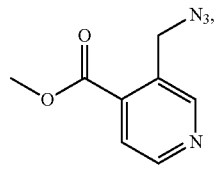

wherein
R$^8$ is pyridyl, pyrimidinyl, pyrazinyl, pyridazyl, —(CH$_2$)$_p$—NHBoc or —(CH$_2$)$_p$—NMe$_2$, in particular pyridyl or —(CH$_2$)$_p$—NHBoc—, with p being 1, 2, 3 or 4.

In certain embodiments, U is selected from phenyl or a five- or six-membered heterocycle, wherein the five- or six-membered heterocycle comprises 1 or 2 heteroatoms.

In certain embodiments, U is selected from phenyl or a five- or six-membered heterocycle, wherein the five- or six-membered heterocycle comprises 1 heteroatom.

In certain embodiments, U is selected from phenyl or a six-membered heterocycle.

In certain embodiments, U is selected from phenyl or a six-membered heterocycle, wherein the six-membered heterocycle comprises 1 or 2 heteroatoms.

In certain embodiments, the five- or six-membered heteroaryl moiety of U comprises 1 or 2 heteroatoms, in particular the five-membered heteroaryl moiety of the moiety U is selected from pyrazole, imidazole, and the six-membered heteroaryl moiety of the moiety U is selected from pyridine, pyridazine, pyrimidine, pyrazine, particularly pyridine.

In certain embodiments, U is selected from phenyl or a six-membered heterocycle, wherein the six-membered heterocycle comprises 1 heteroatom. In certain embodiments, the five-membered heterocycle of the moiety U is selected from pyrazole, imidazole, and the six-membered heterocycle of the moiety U is selected from pyridine, pyridazine, pyrimidine, pyrazine.

In certain embodiments, U is selected from phenyl, pyridine, pyridazine, pyrimidine, pyrazine, particularly phenyl or pyridine, more particularly phenyl.

Linkers according to the invention may release the peptide by an amine switch (FIGS. 5 to 7) or a carbamate switch (FIG. 8). These release mechanisms require a reducible substituent W in ortho or para position relative to the moiety Y, In certain embodiments, U is selected from a moiety of formula 5 or 6,

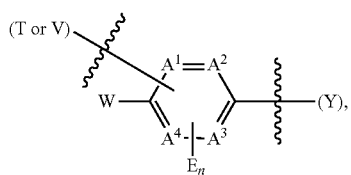

(5)

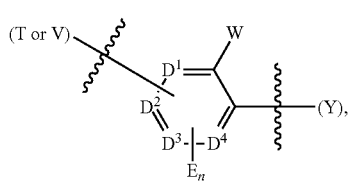

(6)

wherein
T, V, Y, W and E are defined as described above,
U is bound to the moiety T or V,
A$^1$, A$^2$, A$^3$, A$^4$ and D$^1$, D$^2$, D$^3$, D$^4$ are independently from each other selected from C, N, S and O, in particular from C and N, and
n is an integer between 0 and 3, particularly 0, 1 or 2.

In certain embodiments, 2 to 4 moieties of A$^1$, A$^2$, A$^3$ and A$^4$ or of D$^1$, D$^2$, D$^3$ and D$^4$ are C, particularly 3 or 4 moieties of A$^1$, A$^2$, A$^3$ and A$^4$ or of D$^1$, D$^2$, D$^3$ and D$^4$ are C.

In certain embodiments, all moieties A$^1$, A$^2$, A$^3$ and A$^4$ or of D$^1$, D$^2$, D$^3$ and D$^4$ are C, In certain embodiments, U is selected from a moiety of formula 5, 6, 7 or 8,

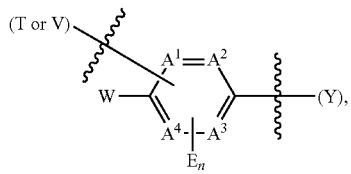

(5)

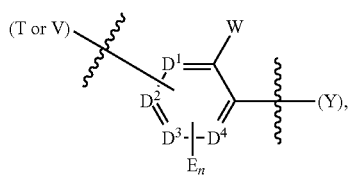

(6)

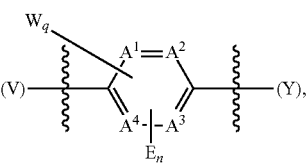

(7)

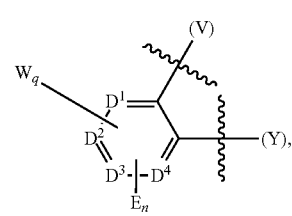

(8)

wherein
T, V, Y, W and E are defined as described above,
in case of formula 5 and 6, U is bound to the moiety T or V,
in case of formula 7 and 8, U is bound to the moiety V, $A^1, A^2, A^3, A^4$ and $D^1, D^2, D^3, D^4$ are independently from each other selected from C, N, S and O, in particular from C and N, wherein 2 to 4 moieties of $A^1, A^2, A^3$ and $A^4$ or of $D^1, D^2, D^3$ and $D^4$ are C, particularly 3 or 4 moieties of $A^1, A^2, A^3$ and $A^4$ or of $D^1, D^2, D^3$ and $D^4$ are C, more particularly all moieties $A^1, A^2, A^3$ and $A^4$ or of $D^1, D^2, D^3$ and $D^4$ are C, n is
  in case of formulas 5 and 6 an integer between 0 and 3,
  in case of formulas 7 and 8 an integer between 0 and 4,
q is an integer between 0 and 4, wherein the sum of n and q is equal or lower than 4.

In certain embodiments, U is selected from a moiety of formula 5 or 6.

In certain embodiments, U is selected from a moiety of formula 5, 6, 7 or 8, wherein
  T, V, Y, W and E are defined as described above,
  in case of formula 5 and 6, U is bound to the moiety T or V,
  in case of formula 7 and 8, U is bound to the moiety V,
  $A^1, A^2, A^3, A^4$ and $D^1, D^2, D^3, D^4$ are independently from each other selected from C, N, S and O, in particular from C and N,
  n is
    in case of formulas 5 and 6 an integer between 0 and 2,
    in case of formulas 7 and 8 an integer between 0 and 2, in particular 0 and 1,
  q is an integer between 0 and 2, in particular 0 and 1.

In certain embodiments, U is selected from a moiety of formula 9, 10, 11 or 12, in particular of formula 9 or 10,

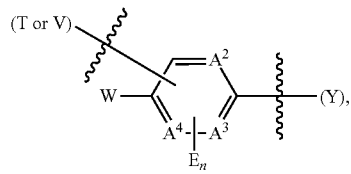

(9)

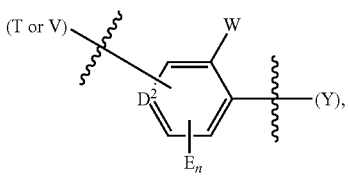

(10)

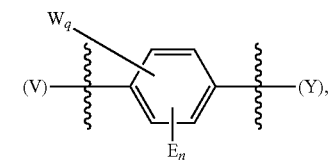

(11)

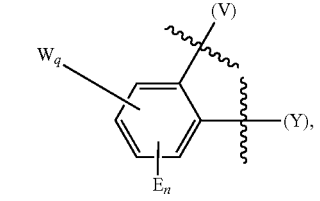

(12)

wherein
  T, V, Y, W, E, q and n are defined as described above,
  in case of formula 9 and 10, U is bound to the moiety T or V,
  in case of formula 11 and 12, U is bound to the moiety V,
  all moieties $A^2, A^3$ and $A^4$ are C or two of $A^2, A^3$ and $A^4$ are C and the other two of $A^2, A^3$ and $A^4$ is N, in particular $A^2$ and $A^3$ are both C, and
  $D^2$ is C or N, in particular C.

In certain embodiments, U is selected from a moiety of formula 9, 10, 11 or 12, particularly of formula 9 or 10,

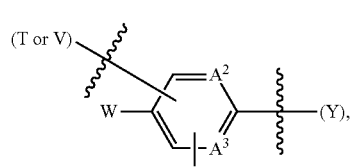

(9)

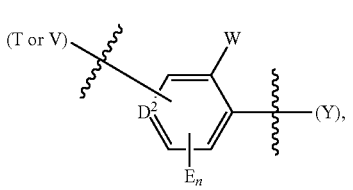

(10)

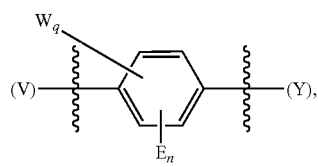

(11)

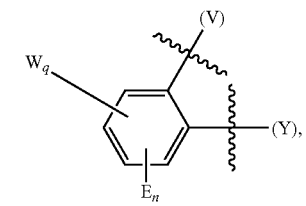

(12)

wherein
  T, V, Y, W, E, q and n are defined as described above,
  in case of formula 9 and 10, U is bound to the moiety T or V,
  in case of formula 11 and 12, U is bound to the moiety V,
  $A^2$ and $A^3$ are both C or one of $A^2$ and $A^3$ is C and the other one of $A^2$ and $A^3$ is N,
  $D^2$ is C or N.

If the moiety U comprises a N-containing heteroaryl, the N atom is protonated under acidic conditions and increases therefore the solubility of the linker molecule.

In certain embodiments, U is selected from a moiety of formula 13, 14, 15, 16, 17, 18, 19, 20 or 21, in particular of formula 13 to 19, more particular of formula 15 or 19,

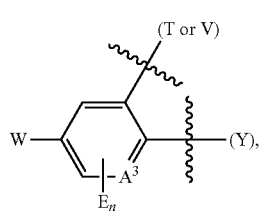

(13)

(14)
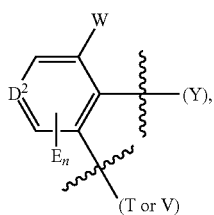

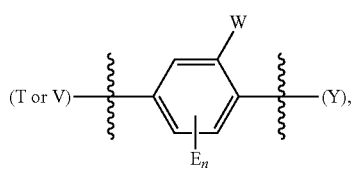
(15)

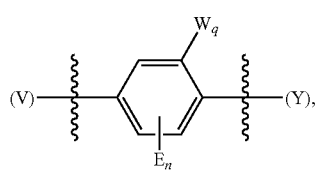
(16)

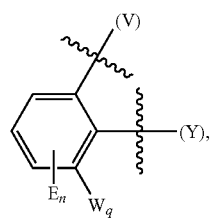
(17)

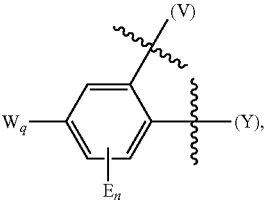
(18)

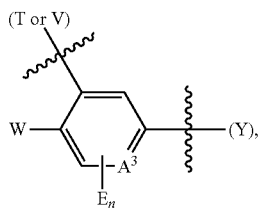
(19)

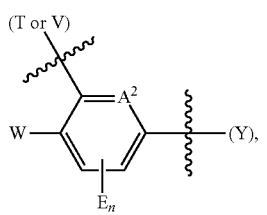
(20)

(21)
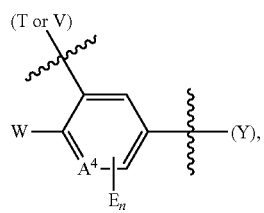

wherein
T, V, Y, W, E, q and n are defined as described above,
in case of formula 13, 14 and 15, U is bound to the moiety T or V,
in case of formula 16, 17 and 18, U is bound to the moiety V,
$A^2$, $A^3$ and $A^4$ is C, N or $N^+Me$, in particular C,
$D^2$ is C or N.

In certain embodiments, U is selected from a moiety of formula 13, 14, 15, 16, 17, 18, 19, 20, 21 or 22,

(22)
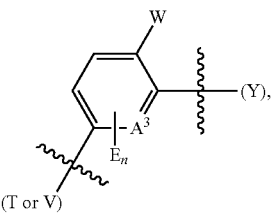

wherein T, V, Y, W, E, q and n are defined as described above,
in case of formula 13, 14, 15, 19, 20, 21 and 22 U is bound to the moiety T or V,
in case of formula 16, 17 and 18, U is bound to the moiety V,
$A^2$, $A^3$ and $A^4$ is C or N, in particular C,
$D^2$ is C or N. In certain embodiments, U is selected from a moiety of formula 13, 14, 15, 16, 17 or 18,

(13)
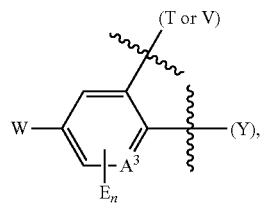

(14)
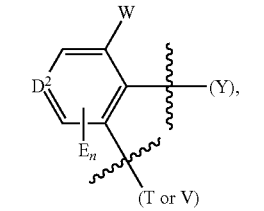

-continued

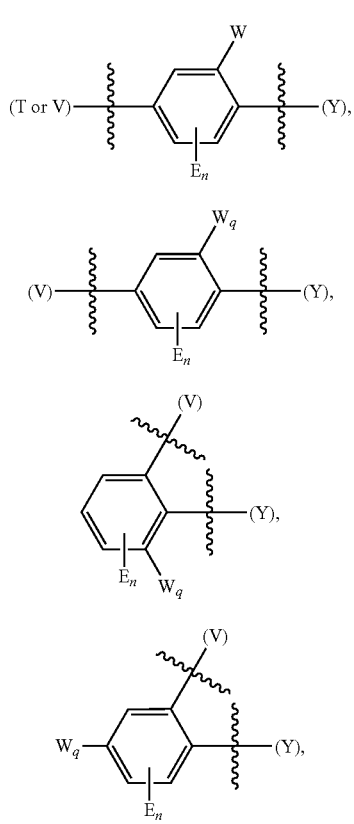

wherein
T, V, Y, W, E, q and n are defined as described above,
in case of formula 13, 14 and 15, U is bound to the moiety T or V,
in case of formula 16, 17 and 18, U is bound to the moiety V,
$A^3$ is C or N,
$D^2$ is C or N.

In certain embodiments, U is selected from a moiety of formula 13, 14, 15, 21 or 22, wherein
T, V, Y, W, E and n are defined as described above,
U is bound to the moiety T or V,
$A^3$ and $A^4$ is C or N, in particular C,
$D^2$ is C or N.

In certain embodiments, U is selected from a moiety of formula 13, 21 or 22.

Particularly for linker molecules that release the peptide via a carbamate switch, U is a phenyl. In certain embodiments, U is selected as described above and all A and all D are C.

For the amine switch with reductive safety lock (FIGS. 5 and 6) and the carbamate switch (FIG. 8), the moiety Y is particularly —$(CH_2)_m$—O—C(=O)— to allow the release of $CO_2$ when the decay of the linker is triggered by a change in pH to release the peptide with a free N-terminus.

In certain embodiments, U is a moiety of formula 13, 14, 15, 16, 17, 18, 19, 20, 21 or 22 and Y is —$(CH_2)_m$—O—C(=O)—.

In certain embodiments, U is a moiety of formula 13, 14, 15, 21 or 22, and Y is —$(CH_2)_m$—O—C(=O)—.

In certain embodiments, U is a moiety of formula 13 or 21 and Y is —$(CH_2)_m$—O—C(=O)—.

For the amine switch with nucleophilic release (FIG. 7), the linker is only stable under acidic conditions, if the moiety Y forms an amide bond with the peptide. In certain embodiments, Y is —$(CH_2)_m$—C(=O)—.

The peptide may be coupled to the peptide via common amino acid coupling if the linker molecule ends with —COOH. In certain embodiments, Y is —$(CH_2)_m$—C(=O)— and Z is —OH.

For the amine switch with nucleophilic release, U is particularly a moiety of formula 22, Y is —$(CH_2)_m$—C(=O)— and Z is —OH.

In certain embodiments, Z is selected from: —F, —Cl, —Br, —I, —$N_3$, —OH, —O(C=O)$CH_2$(C=O)OH—$SR^{14}$, —$OCF_3$, —$OCH_2CF_3$, —$OSO_2CF_3$, —$SO_2C_6H_4CH_3$, —$SO_2CF_3$, —$SO_2CH_3$

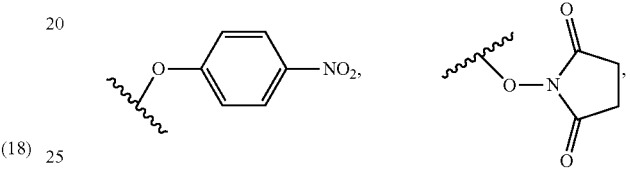

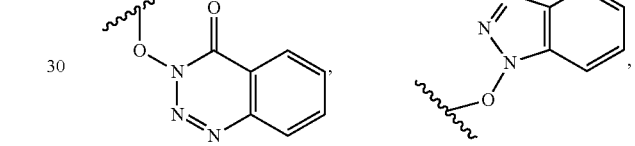

in particular —OH, —Cl,

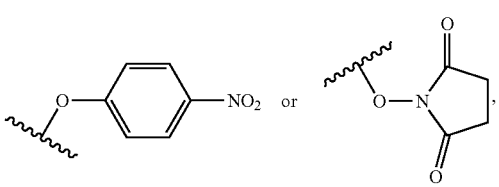 [SMILES: *Oc1ccc([N+](=O)[O-])cc1 ; *ON1C(=O)CCC1=O]

in particular —OH,

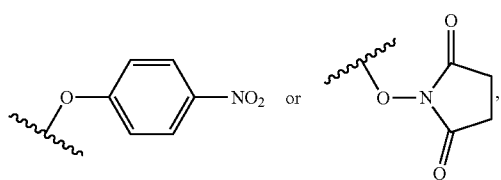

wherein R$^{14}$ is an C$_1$-C$_6$-alkyl-, an acrylic- or benzylic substituent.

Linker molecules of type 1 that are suitable for the release of the peptide by an amine switch with azide reductive safety lock (FIG. 5) may be composed of the following moieties:
- U is phenyl or pyrimidyl, particularly U is of formula 13, 14, 15, 21 or 22,
- W is —N$_3$,
- n of E is 1 and E is selected from pyridyl, pyrimidinyl, pyridazinyl, —N(CH$_3$)$_2$, —N=N-pyridyl or n is 0, particularly n is 0,
- a of V is 1 and V is selected from -piperazinyl-, -piperazinyl-CH$_2$—, —N(CH$_3$)—, pyrimidinyl, pyridyl, particularly from -piperazinyl-, -piperazinyl-CH$_2$—, —N(CH$_3$)—, and
- Y is —(CH$_2$)$_m$—O—C(=O)— with m being 1, 2 or 3, in particular 1 or 2, more particularly 1.

The pyridyl moiety is connected to U at position 3 or 5.

In certain embodiments, U is selected from a moiety of formula 13, 14, 15, 21 or 22, Linker molecules of type 2 that are suitable for the release of the peptide by an amine switch without an azide (FIG. 6) may be composed of the following moieties:
- U is pyridinyl or phenyl, particularly U is of formula 13, 14 or 21,
- W is selected from —S—S-tertbutyl, —NO$_2$, —N=N-pyridyl,

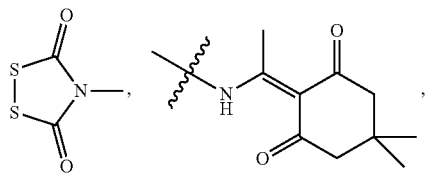

particularly from —S—S-tertbutyl, —NO$_2$,
- n of E is 0,
- a of V is 1 and V is selected from —C(=O)—NH— and piperazinyl, and
- Y is —(CH$_2$)$_m$—O—C(=O)— with m being 1, 2 or 3, in particular 1 or 2, more particularly 1.

In certain embodiments, U is selected from a moiety of formula 13, 14 or 21,

Linker molecules of type 3 that are suitable for the release of the peptide by an amine switch with a nucleophilic release (FIG. 7) may be composed of the following moieties:
- U is phenyl or pyridinyl, particularly phenyl, more particularly U is a moiety of formula 13 or 14,
- W is —N$_3$, —S—S-tertbutyl, —S—S-pyridyl, particularly —N$_3$,
- n of E is 0,
- a of V is 1 and V is piperazinyl, —NH—, —C(=O)—NH—, particularly piperazinyl, and
- Y is —(CH$_2$)$_m$—C(=O)— with m being 1, 2 or 3, in particular 1 or 2, more particularly 1.

In certain embodiments, U is selected from a moiety of formula 13 or 14, wherein in particular all moieties D and A are C.

Linker molecules of type 4 that are suitable for the release of the peptide by a carbamate switch (FIG. 8) may be composed of the following moieties:
- U is phenyl, particularly U is of formula 13 or 15, wherein in particular the moiety A is C,
- W is —N$_3$,
- n of E is 1 or 2 and E is —Br,
- a of V is 1 and V is —NH—C(=O)—, and
- Y is —(CH$_2$)$_m$—O—C(=O)— with m being 1, 2 or 3, in particular 1 or 2, more particularly 1.

In certain embodiments, U is selected from a moiety of formula 13 or 15, wherein in particular the moiety A is C, In certain embodiments, Z is selected from: —F, —Cl, —Br, —I, —N$_3$, —OH, —SR$^{14}$, —OCF$_3$, —OCH$_2$CF$_3$, —OSO$_2$CF$_3$, —SO$_2$C$_6$H$_4$CH$_3$, —SO$_2$CF$_3$, —SO$_2$CH$_3$

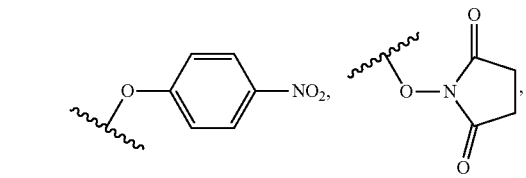

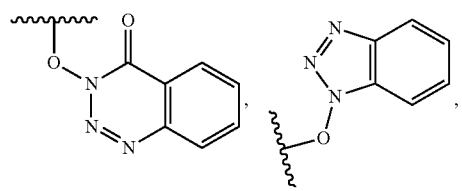

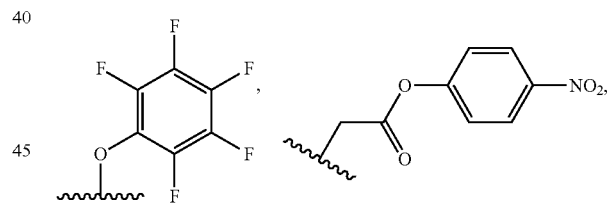

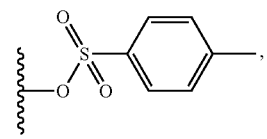

in particular —OH, —Cl,

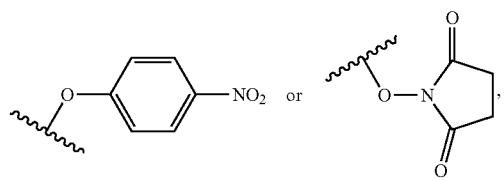 [SMILES: *Oc1ccc([N+](=O)[O-])cc1 ; *ON1C(=O)CCC1=O]

in particular —OH,

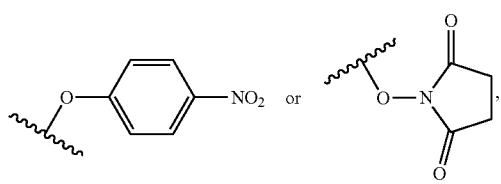

wherein R¹⁴ is an C₁-C₆-alkyl-, an acrylic- or benzylic substituent.

In case of Z being —OH, the —OH moiety is activated by a coupling reagent as commonly used e.g. in solid phase peptide synthesis, and functions as a leaving group.

In certain embodiments, the compound of formula 1 is selected from a compound of formula X1, X2, X3, X4, X5, X6, X7, X8, X9, X10, X11, X12, X14, X15, X16, X17, X18, X19, X20, X21, X22, X23 X24, X25, X26, X27, x28, X29, X30, X31, X32, X33, X34, X35, X36, X37, X38, X39, X40, X41, X42, X43, X44, X45, X46 or X47.

(X1)

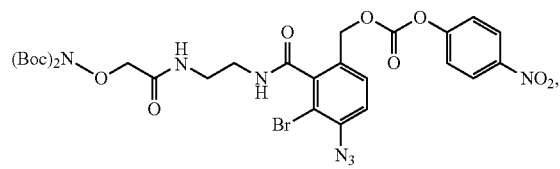

(X2)

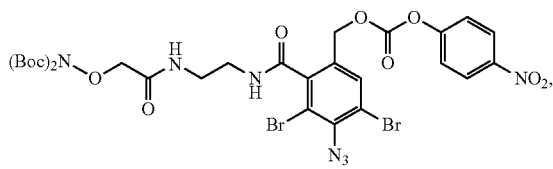

(X3)

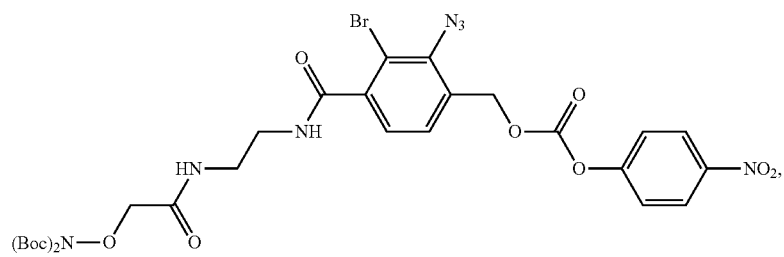

(X4)

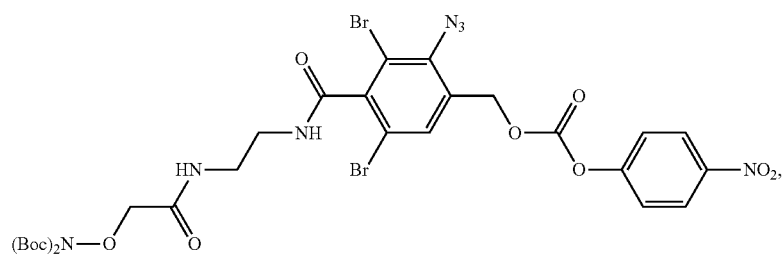

(X5)

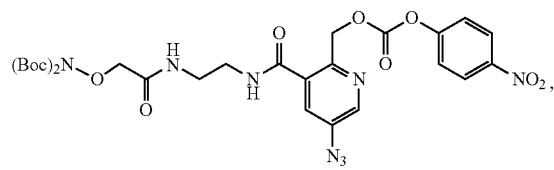

(X6)

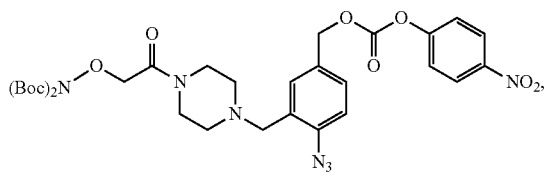

(X7)

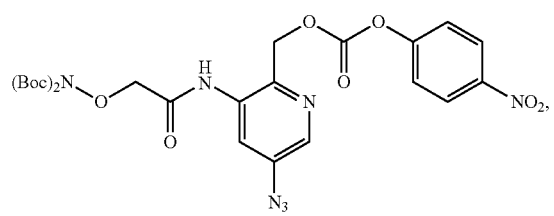

(X8)

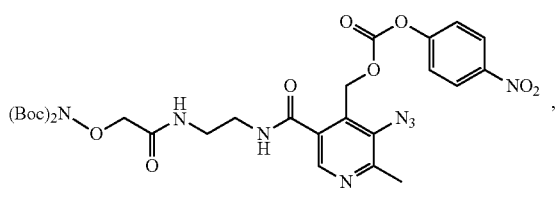

-continued
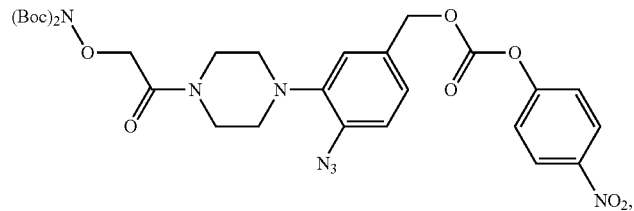
(X9)
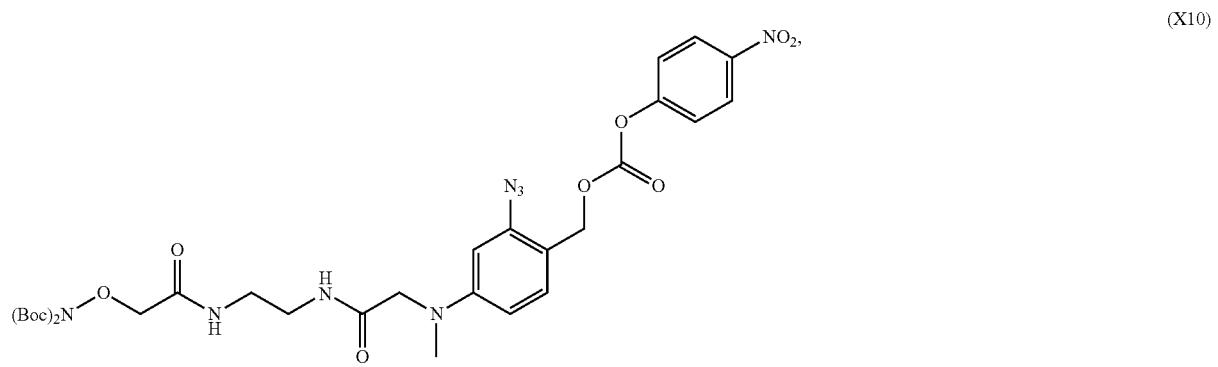
(X10)
(X11)                    (X12)
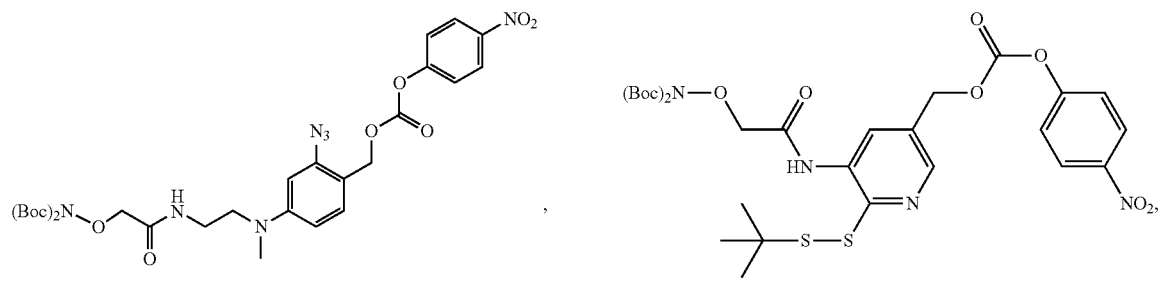
(X13)                    (X14)
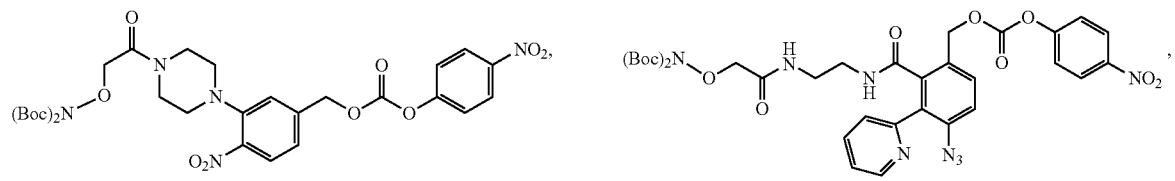
(X15)                    (X16)
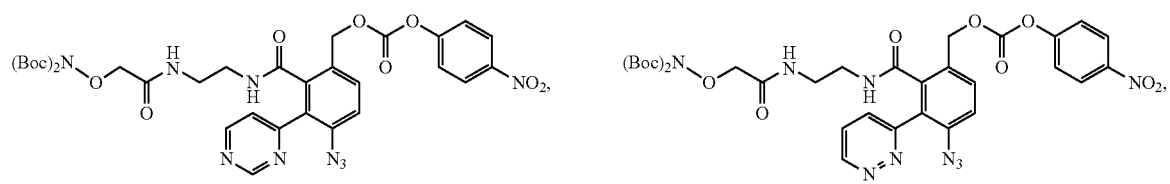
(X17)                    (X18)
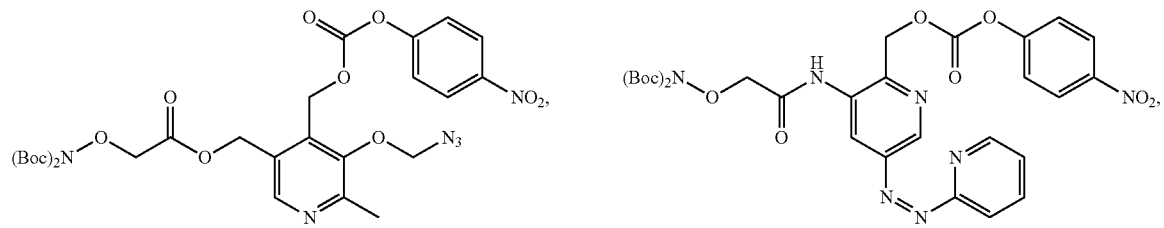

-continued
(X19)
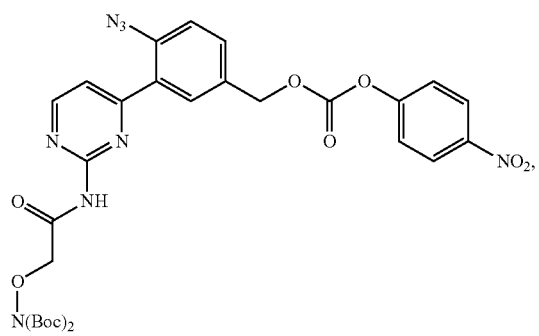
(X20)
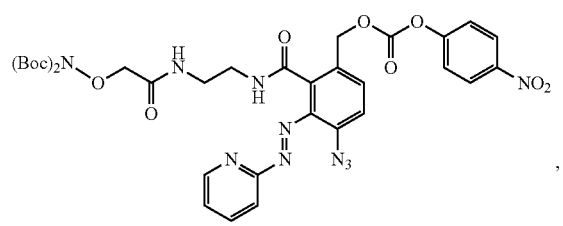
(X21)
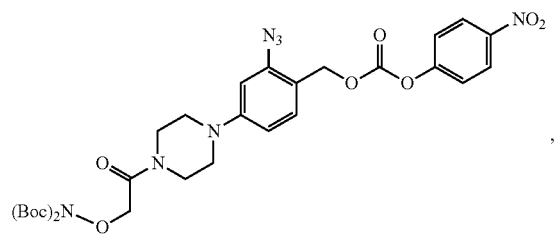
(X22)
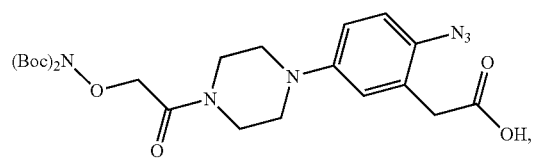
(X23)
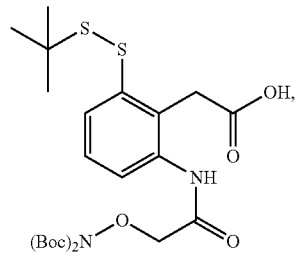
(X24)
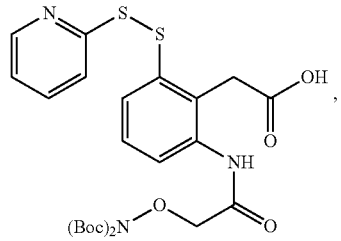
(X25)
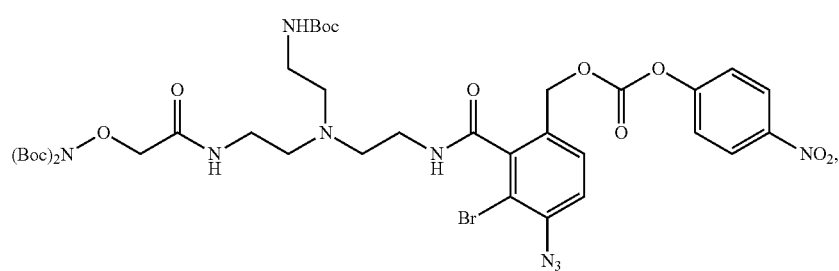
(X26)
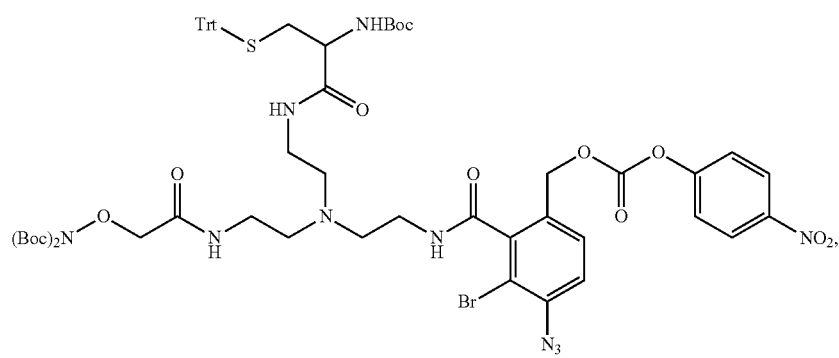

-continued
(X27) 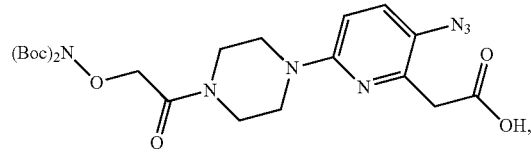
(X28) 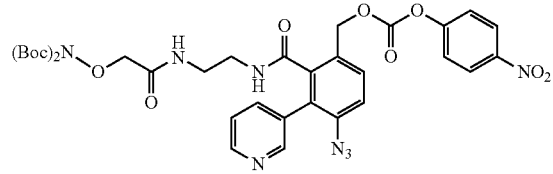
(X29) 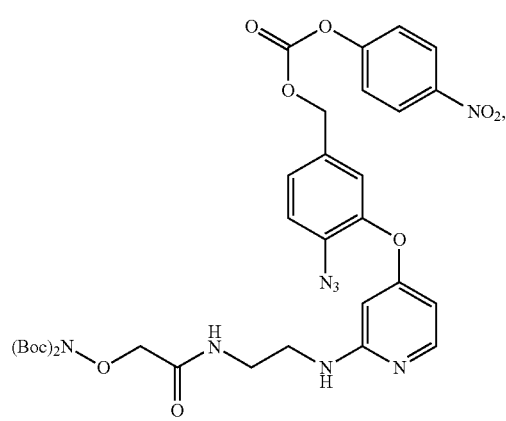
(X30) 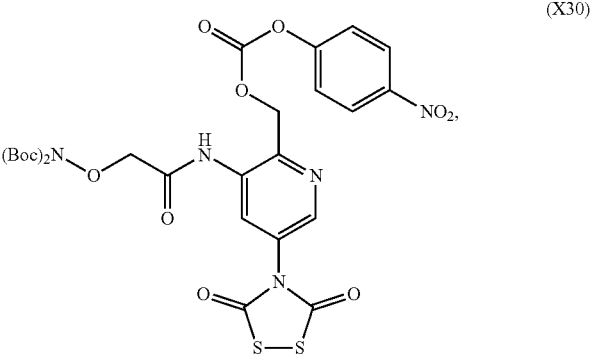
(X31) 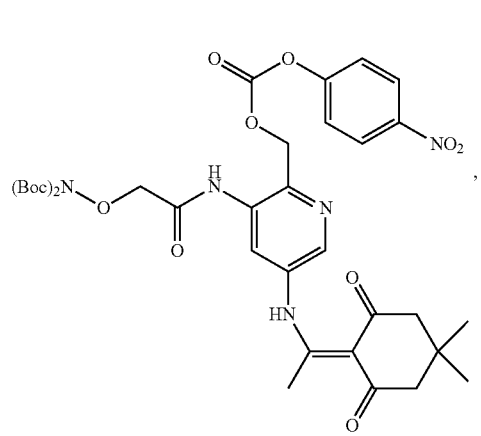
(X32) 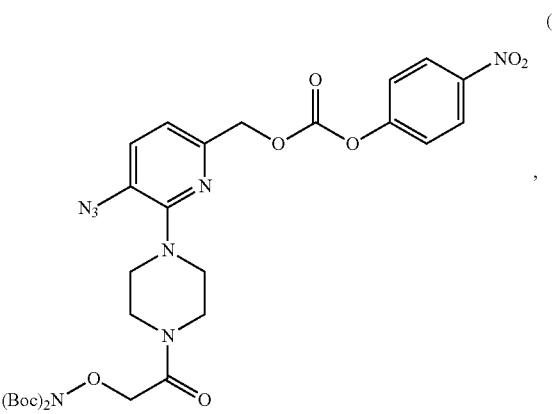
(X33) 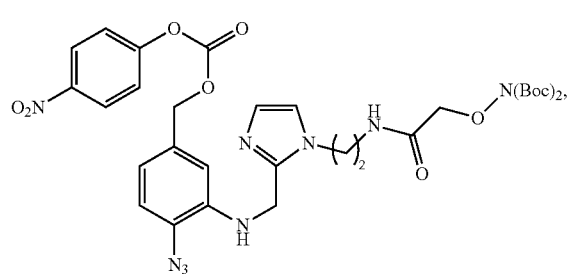
(X34) 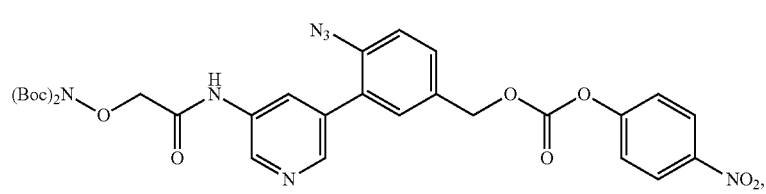

-continued
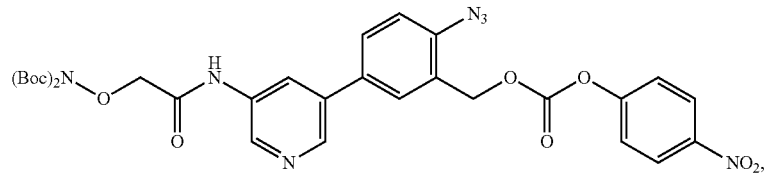
(X35)
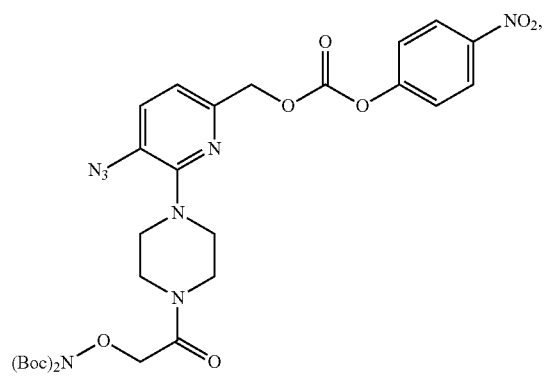
(X36)
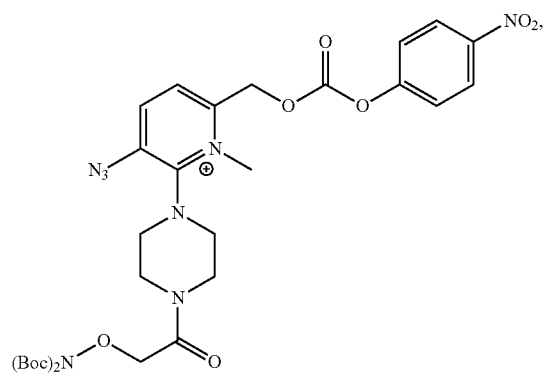
(X37)
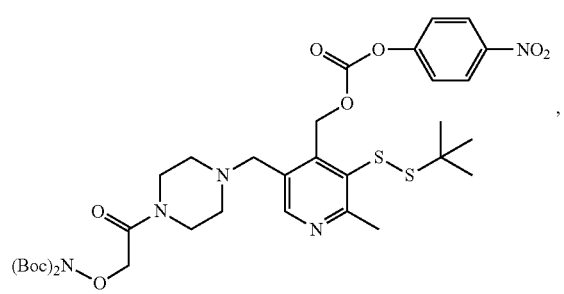
(X38)
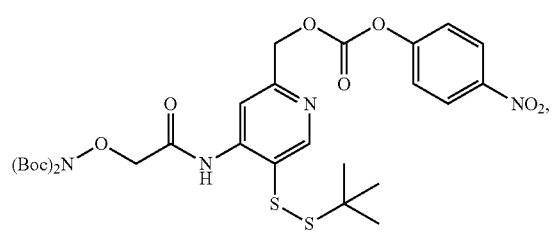
(X39)
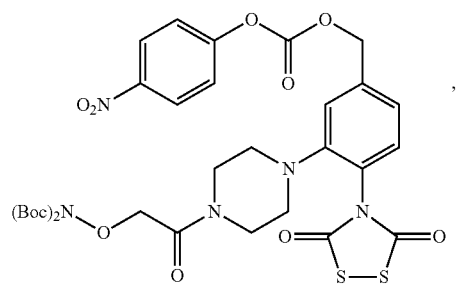
(X40)
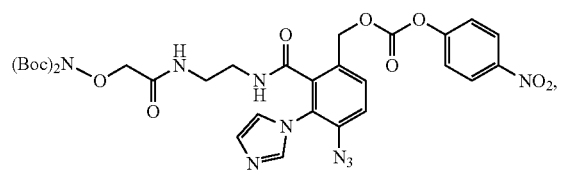
(X41)
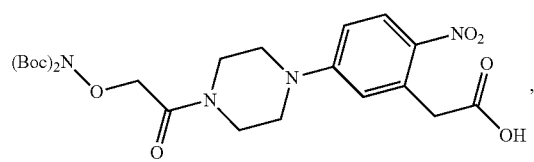
(X42)
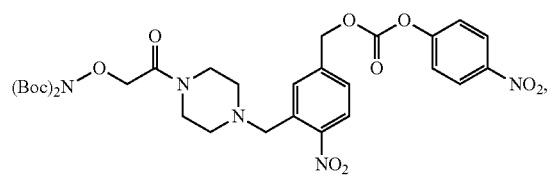
(X43)

-continued (X44)
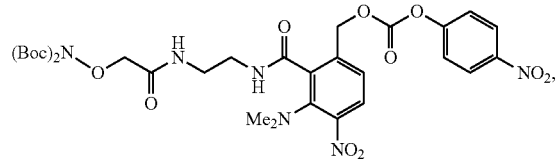

(X45)
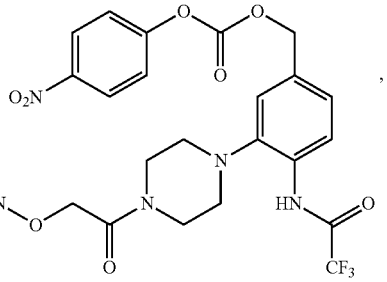

(X46)
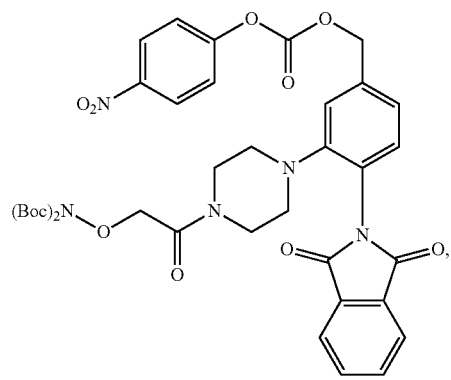

(X47)
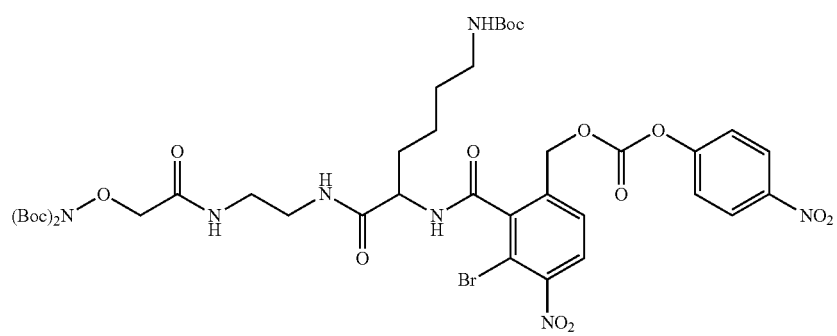

A second aspect of the invention aims at a method for purifying peptides.

According to a second aspect of the invention, a method for purifying peptides is provided. The method comprises the steps of
- providing a crude linker-modified peptide, wherein the crude peptide is covalently bound to a linker molecule according to the first aspect of the invention,
- in a coupling step, coupling the linker-modified peptide with a solid support yielding an immobilized linker-modified peptide,
- in a releasing step, releasing the peptide by adding a reducing agent under acidic conditions.

The linker molecule according to the first aspect of the invention may be used in a method for purifying peptide. In a first step, a crude peptide mixture is contacted with a linker molecule according to the first aspect of the invention and a crude peptide is coupled to a linker molecule yielding a crude linker-modified peptide. The crude peptide is coupled to a linker molecule by standard methods that are generally known to a general expert in the field of chemistry, biochemistry or pharmacy.

During purification, the stability of the linker molecule can be addressed by adjusting the pH. Under acidic conditions (in particular at a pH below the pKa of the most basic heteroatom of the linker molecule), the linker molecule is stable due to the fact that this heteroatom is protonated and withdraws electrons (FIG. 5, 6, 7). Upon binding of the linker to a peptide and immobilization on a solid support, the peptide is released via a reduced intermediate under reducing conditions, e.g. adding a reducing agent such as triphenylphoshine under acidic conditions. The reduced intermediate is characterized by a reduced linker moiety, e.g. an azaylide. The linker moiety of the reduced intermediate decays over time or upon a trigger, such as increasing the pH, in particular to pH>pKa of the most basic heteroatom of the linker moiety of the reduced intermediate. Thus, all steps before the release of the peptide (coupling, optional washing and reduction of the linker) are performed under acidic conditions. Upon increase of the pH to a pH above the pKa of the most basic heteroatom of the linker moiety of the reduced intermediate, the reduced intermediate linker moiety decays by 1.4/1.6 elimination reaction or nucleophilic attack and the peptide is released.

The most basic heteroatom of the linker molecule/linker moiety of the reduced intermediate relates to the following: For example, the moiety U consists of a pyridine substituted by —$N_3$. The heteroatom N of pyridine has a $pK_a$~5 which is higher than the $pK_a$ of the —$N_3$ moiety or the reduced —$N_3$ moiety ($pK_a$ of —$NH_3$ approx. 4.6). Thus, the most basic heteroatom is the N of the pyridine moiety. By shifting the pH to pH>5, the linker moiety of the reduced intermediate undergoes an elimination reaction and the peptide is released. This mechanism is referred to as amine switch.

Alternatively, the linker molecule may decay by a carbamate switch (FIG. 8). Suitable linker molecules comprise an electron-withdrawing moiety such as —Br and a reducible moiety, e.g. —$N_3$. The linker molecule is stable under TFA conditions due to the electron withdrawal. Upon reduction, the linker molecule is stable when the pH is higher than the pKa of the carbamate. Finally, the peptide is released via 1.6 elimination by decreasing the pH to pH<pKa of the carbamate.

In certain embodiments, the pH in all steps before adding a reducing agent is pH<pKa of the most basic heteroatom of the linker moiety.

In certain embodiments, the peptide is released via an intermediate.

In certain embodiments, the peptide is released via a reduced intermediate characterized by a reduced linker moiety of the immobilized linker-modified peptide by adding a reducing agent under acidic conditions.

In certain embodiments, a reduced intermediate characterized by a reduced linker moiety of the immobilized linker-modified peptide is achieved in the releasing step and the peptide is released from said reduced intermediate by a trigger, in particular a change in temperature and/or pH, more particularly by increasing the pH to pH>pKa of the most basic heteroatom of the linker moiety of the reduced intermediate in case of an amine switch, or by decreasing the pH to pH<pKa of the carbamate in case of a carbamate switch.

In certain embodiments, a reduced intermediate characterized by a reduced linker moiety of the immobilized linker-modified peptide is achieved in the releasing step and the peptide is released from said reduced intermediate by a trigger, in particular a change in temperature and/or pH, more particularly by increasing the pH to pH>pKa of the most basic heteroatom of the linker moiety of the reduced intermediate.

The peptide is released from the intermediate spontaneously or by a trigger.

In certain embodiments, the trigger is a change in temperature and/or pH.

In certain embodiments, the change in temperature is an increase of the temperature from ambient temperature (20° C. to 30° C.) to a higher temperature, wherein the higher temperature does not exceed 100° C., particularly 70° C., more particularly 50° C.

As described above, linker that are suitable for an amine switch, decay—if they are reduced—when the pH is increased to pH above the pKa of the most basic heteroatom.

In certain embodiments, the trigger is a shift in pH, in particular increasing the pH.

In certain embodiments, the peptide is released from a reduced intermediate by increasing the pH to pH>pKa of the most basic heteroatom of the linker moiety of the reduced intermediate.

Linkers that are suitable for a carbamate switch dacay—it they are reduced—when the pH is decreased to a pH below the pKa of the carbamate.

In certain embodiments, the trigger is a shift in pH, in particular decreasing the pH.

In certain embodiments, the peptide is released from a reduced intermediate by decreasing the pH to pH<pKa of the carbamate of the linker moiety.

If the reduced intermediate is stable under acidic conditions (amine switch) or at pH>pKa of the carbamate (carbamate switch), an additional washing step can be performed to remove excess reducing agent. As a reducing agent may react not only with the linker moiety but also with the peptide, unwanted side reactions between the reducing agent and the peptide are reduced by the additional washing step. Furthermore, none volatile reducing agents or products of their usage are also impurities, that would have to be removed by an additional purification step.

In certain embodiments, the reducing agent is removed by washing after the reduced intermediate is formed and before the peptide is released from the reduced intermediate.

In certain embodiments, the reducing agent is removed using MeCN.

In certain embodiments, the linker molecule according to the first aspect of the invention comprises a moiety W and/or E that comprises an azide (—$N_3$) moiety.

In certain embodiments, the linker-modified peptide is additionally bound to a synthesis resin and the synthesis resin is cleaved off before the coupling step is performed, in particular at pH<pKa of the most basic heteroatom of the linker molecule.

The cleavage of the peptide off the synthetic support is achieved by usage of TFA, finalized by precipitating the peptide (e.g. after 2-8 h) out of the TFA mixture providing a crude peptide mixture. For the precipitation, cold ether ($Et_2O$, $iPr_2O$, MeOtBu, THF/Hexane (1:1)) can be used.

The crude peptide mixture is dissolved in a suitable organic solvent, particular DMSO, and a buffer system, particularly 10 volume percent of sodium citrate buffer 0.1 M at pH 4.5, is added.

The solid support for the coupling step is an aldehyde modified solid support, in particular agarose beads, polylysine, polyethylene glycol, polyamide, polystyrene and copolymers of those, to which the dissolved crude peptide mixture is added.

In certain embodiments, the solid support comprises aldehyde moieties.

In certain embodiments, non-reacted aldehyde moieties of the solid support are blocked using a blocking agent after performing the coupling step.

In certain embodiments, the blocking agent reacts with aldehyde moieties of the solid support and comprises a thiol and/or amine moiety.

In certain embodiments, the blocking agent is selected from cysteine, threonine, 2-mercaptoethanol, cysteamine, ethandithiole, hydroxylamine, O-methylhydroxylamine, N-methylhydroxylamine, dithiothreitol, hydrazine.

In certain embodiments, the blocking agent is selected from cysteine and N-methylhydroxylamine.

The coupled product is washed, particularly with DMSO, 6 M guanidium hydrochloride, EtOH/water (7:3) with 0.1 M NaCl, water, MeCN.

In certain embodiments, the releasing step is performed at pH<pKa of the most basic heteroatom of the linker molecule.

In certain embodiments, the releasing step is performed at pH<pKa of the carbamate of the linker molecule.

In certain embodiments, the reducing agent is selected from triphenylphosphine, trimethylphosphine, triethylphosphine, tributylphosphine or tris(2-carboxyethyl)phosphine, trimethyl phosphite, triethyl phosphite, tributyl phosphine, diethyl phosphite, 5,5'-Dithiobis(2-nitrobenzoic acid), sodium dithionite (Na$_2$S$_2$O$_4$), ethandithiole, Propandithiol, dithioerythritol, dithiothreitol, Na$_2$S, NaSH, glutathione, 2,2'-dithiodipyridine, BH$_3$, 4,4,5,5-tetramethyl-1,3,2-dioxaborolane, catechol borane, borane tetrahydrofuran, borane dimethyl sulfide, borane dimethylamine complex, borane triphenylphosphine complex, borane tert-butylamine, LiAlH$_4$, LiBH$_4$, NaBH$_4$, NaBH$_3$CN, NaBH(OMe)$_3$, NaBH(OCCH$_3$)$_3$, LiAlH(OCMe$_3$)$_3$, hydroquinone, sodium ascorbate, ascorbic acid, ascorbic acid with Kl, hydrazine, NH=NH, formaldehyde.

In certain embodiments, the reducing agent is selected form dithioerythritol, dithiothreitol, triphenylphosphine, ascorbic acid with Kl, tributylphosphine, trimethylphosphine, tris(2-carboxyethyl)phosphine, sodium dithionite (Na$_2$S$_2$O$_4$), borane dimethyl sulfide, borane triphenylphosphine complex, NaBH$_4$, ascorbic acid In certain embodiments, the reducing agent is selected from dithioerythritol, dithiothreitol, ascorbic acid with Kl, triphenylphosphine and trimethylphosphine.

In certain embodiments, the reducing agent is selected from triphenylphosphine, trimethylphosphine, triethylphosphine, tributylphosphine or tris(2-carboxyethyl)phosphine, trimethyl phosphite, triethyl phosphite, tributyl phosphine, diethyl phosphite, 5,5'-Dithiobis(2-nitrobenzoic acid), sodium dithionite (Na$_2$S$_2$O$_4$), ethandithiole, Propandithiol, dithiothreitol, Na$_2$S, NaSH, glutathione, 2,2'-dithiodipyridine, BH$_3$, 4,4,5,5-tetramethyl-1,3,2-dioxaborolane, catechol borane, borane tetrahydrofuran, borane dimethyl sulfide, borane dimethylamine complex, borane triphenylphosphine complex, borane tert-butylamine, LiAlH$_4$, LiBH$_4$, NaBH$_4$, NaBH$_3$CN, NaBH(OMe)$_3$, NaBH(OCCH$_3$)$_3$, LiAlH(OCMe$_3$)$_3$, hydroquinone, sodium ascorbate, ascorbic acid, hydrazine, NH=NH, formaldehyde.

In certain embodiments, the reducing agent is selected from triphenylphosphine, tributylphosphine, trimethylphsophine, triethylphosphine or tris(2-carboxyethyl)phosphine, sodium dithionite (Na$_2$S$_2$O$_4$), borane dimethyl sulfide, borane triphenylphosphine complex, NaBH$_4$, ascorbic acid.

In certain embodiments, the reducing agent is selected from triphenylphosphine, trimethylphsophine, triethylphosphine or tris(2-carboxyethyl)phosphine, sodium dithionite (Na$_2$S$_2$O$_4$), borane dimethyl sulfide, borane triphenylphosphine complex, NaBH$_4$, ascorbic acid.

In certain embodiments, the reducing agent is selected from triphenylphosphine, sodium dithionite (Na$_2$S$_2$O$_4$), borane dimethyl sulfide, borane triphenylphosphine complex, NaBH$_4$, ascorbic acid.

In certain embodiments, the reducing agent is selected from triphenylphosphine and trimethylphosphine.

In certain embodiments, the reducing agent is triphenylphosphine.

In certain embodiments, method comprises the steps of
providing a crude linker-modified peptide, wherein the crude peptide is covalently bound to a linker molecule according to the first aspect of the invention, wherein the linker molecule comprises a moiety W and/or E that comprises an azide moiety,
in a coupling step, coupling the linker-modified peptide with a solid support yielding an immobilized linker-modified peptide,
in a releasing step, releasing the peptide by adding a reducing agent under acidic conditions.

In certain embodiments, method comprises the steps of
providing a crude linker-modified peptide, wherein the crude peptide is covalently bound to a linker molecule according to the first aspect of the invention, wherein the linker molecule comprises a moiety W and/or E that comprises an azide moiety,
in a coupling step, coupling the linker-modified peptide with a solid support yielding an immobilized linker-modified peptide,
in a releasing step, releasing the peptide by adding a reducing agent under acidic conditions yielding a reduced intermediate followed by increasing the pH pH>pKa of the most basic heteroatom of the linker moiety of the reduced intermediate.

In certain embodiments, method comprises the steps of
providing a crude linker-modified peptide, wherein the crude peptide is covalently bound to a linker molecule according to the first aspect of the invention, wherein the linker molecule comprises a moiety W and/or E that comprises an azide moiety,
in a coupling step, coupling the linker-modified peptide with a solid support yielding an immobilized linker-modified peptide,
in a releasing step, releasing the peptide by adding a triphenylphosphine, trimethylphosphine, triethylphosphine or tris(2-carboxyethyl)phosphine, particularly triphenylphosphine, under acidic conditions yielding a reduced intermediate followed by increasing the pH pH>pKa of the most basic heteroatom of the linker moiety of the reduced intermediate.

According to a sub-aspect of the second aspect of the invention, a method for purifying a crude peptide prepared by solid-phase peptide synthesis is provided.

In certain embodiments, the method for purifying peptides comprises the steps of
a) providing a peptide bound to a synthetic resin, wherein the peptide is additionally covalently bound to a linker molecule according to claim 1, wherein the linker molecule comprises a moiety W and/or E that comprises an azide moiety,
b) cleaving of the peptide off the synthetic resin
c) coupling the cleaved peptide mixture with a solid support
d) releasing the peptide with triphenylphosphine, or trimethylphosphine, triethylphosphine or tris(2-carboxyethyl)phosphine, particularly triphenylphosphine.

The cleavage of the peptide off the synthetic support is achieved by usage of TFA, finalized by precipitating the peptide (e.g. after 2-8 h) out of the TFA mixture providing a crude peptide mixture. For the precipitation, cold ether (Et$_2$O, iPr$_2$O, MeOtBu, THF/Hexane (1:1)) can be used.

The crude peptide mixture is dissolved in a suitable organic solvent, particular DMSO, and a buffer system, particularly 10 volume percent of sodium citrate buffer 0.1 M at pH 4.5, is added.

The solid support for the coupling step is an aldehyde modified solid support, in particular agarose beads, polylysine, polyethylene glycol, polyamide, polystyrene and copolymers of those, to which the dissolved crude peptide mixture is added.

The coupled product is washed, particularly with DMSO, 6 M guanidium hydrochloride, EtOH/water (7:3) with 0.1 M NaCl, water, MeCN.

In certain embodiments, triphenylphosphine, trimethylphosphine, triethylphosphine or tris(2-carboxyethyl)phosphine, particularly triphenylphosphine, is added in MeCN/AcOH (9:1). In certain embodiments, the addition is made for 15 min.

In certain embodiments, triphenylphosphine, trimethylphosphine, triethylphosphine or tris(2-carboxyethyl)phosphine is added in MeCN/AcOH/H$_2$O (90:5:5) and/or wherein after the addition of triphenylphosphine, trimethylphosphine, triethylphosphine or tris(2-carboxyethyl)phosphine, particularly triphenylphosphine, the formed azaylide is washed out, in particular with MeCN or MeCN/H$_2$O (9:1).

In certain embodiments, triphenylphosphine, trimethylphosphine, triethylphosphine or tris(2-carboxyethyl)phosphine, particularly triphenylphosphine, is added in MeCN/AcOH/H$_2$O (90:5:5). In certain embodiments, the addition is made for 15 min.

In certain embodiments, after the addition of triphenylphosphine, trimethylphosphine, triethylphosphine or tris(2-carboxyethyl)phosphine the formed azaylide is washed, in particular with MeCN or MeCN/H$_2$O (9:1).

In certain embodiments, after the addition of triphenylphosphine, trimethylphosphine, triethylphosphine or tris(2-carboxyethyl)phosphine the formed azaylide is washed, in particular with MeCN.

In certain embodiments, the formed azaylide is hydrolyzed, in particular with H$_2$O/TFA. The ration can be 99.95% water to 50% water.

When the linker, in particular U, E, W or V are nitrogen containing heterocycles the pH should be above the pKa of the heterocyclic moiety, this might be already the case in the TFA-water hydrolysis mixture or by addition of a buffer solution with the desired pH.

In certain embodiments, an elution step is performed after the hydrolysis, in particular with TFA/H$_2$O, more particular with a ratio of 9:1.

In certain embodiments, an elution step is performed after the hydrolysis, in particular with TFA/H$_2$O, more particular with a ratio of 95:5.

In certain embodiments, the hydrolysis product is precipitated, in particular by adding cold ether, more particular Et$_2$O, iPr$_2$O, MeOtBu, THF/Hexane (1:1).

Terms and Definitions

In the context of the present invention, "electron-withdrawing group" or "EWG" is any chemical group that is able to draw electrons away from its connected atom or acrylic system through inductive or mesomeric effect.

In the context of the present invention, Hammett constants are constants as calculated and described in Hansch and Taft (1991), Chem. Rev. 91:165-195. A positive Hammett constant reflects the ability of a substituent to exert an electron withdrawing effect on a phenyl moiety and a negative value indicates that a substituent exerts and electron donating effect. The electron withdrawing effect is stronger the larger the Hammett constant is. Hammett constants are empirically determined constants for substituents of phenyl moieties in meta ($\sigma_m$) and para position ($\sigma_p$). In the context of the present invention, the position is determined in relation to the binding of the moiety Y. For substituents in ortho position, Hammett values for the para position are a good approximation and therefore used in the context of the present invention to calculate the sum of Hammett values of the substituents V, W and E.

In the context of the present invention, the term "under acidic conditions" relates to a pH below pH 7, in particular a pH below the pKa of the linker, more particularly TFA>50%, in the presence of water pH<0.

In the context of the present invention, the term alkyl refers to a linear or branched saturated hydrocarbon. For example, the term $C_{1-12}$ alkyl signifies saturated linear or branched hydrocarbon having 1, 2, 3, 4, 5, 6, 7, 8, 9, 10, 11 or 12 carbon atoms. Non-limiting examples for a $C_1$-$C_4$ alkyl are methyl, ethyl, propyl, n-butyl, 2-methylpropyl and tert-butyl.

EXAMPLES

Example 1 of Linker Type 4: Purification of Naturally Occurring and Research Peptides P1 and P2

The inventive method for the purification of peptides was applied to two peptides of different polarity, these were H-ARTKQTARKSTGGKA-OH (SEQ ID NO: 1) (P1) fragment 2-16 of the Histone H3 protein and H-AKADEVSLHKWYG-NH$_2$ (SEQ ID NO: 2) (P2) is a peptide sequence intended for research.

Figure 1:
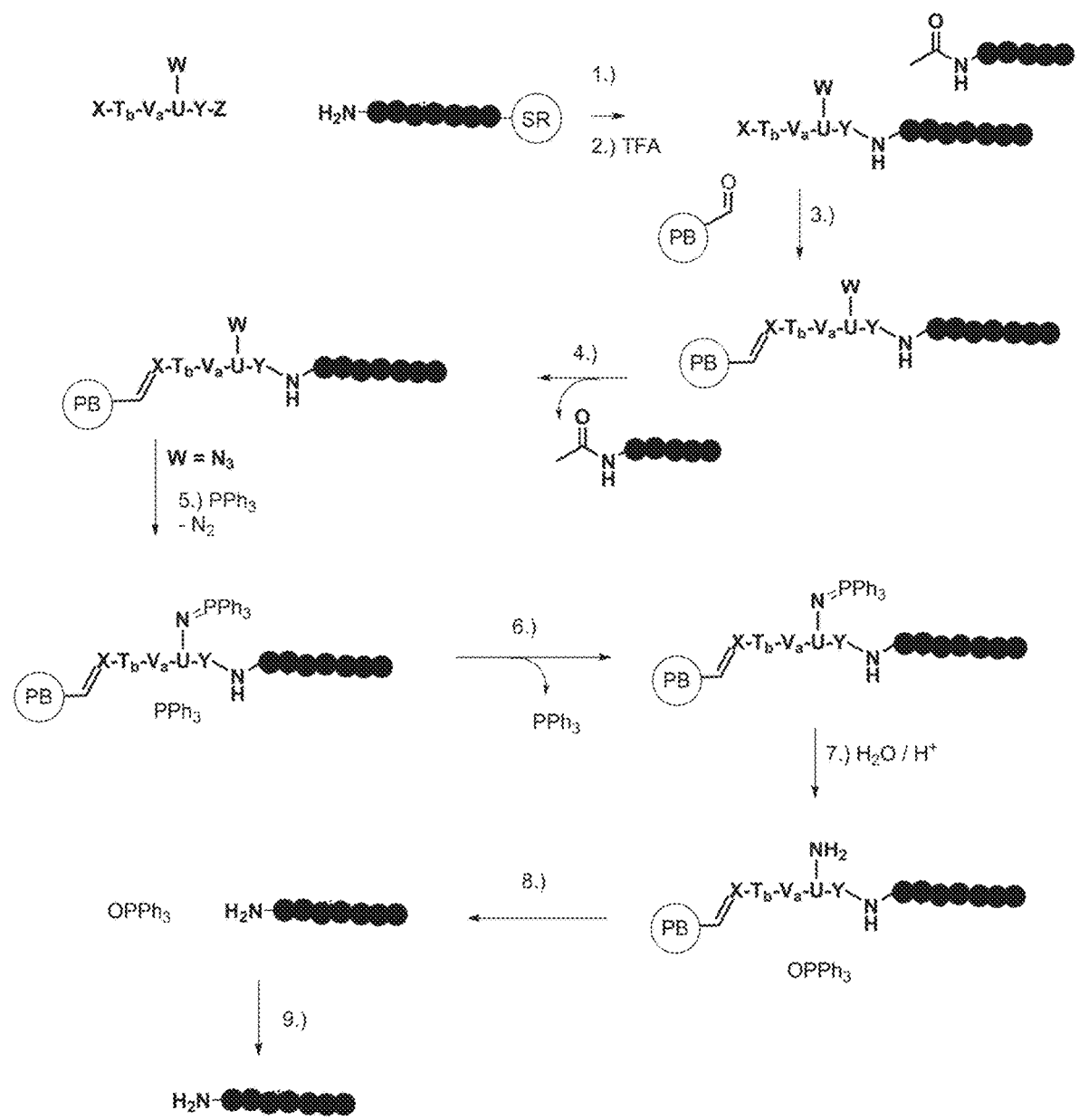
FIG. 1 shows a schematic representation of the inventive peptide purification by usage of linkers of the type X-$T_b$-$V_a$-U(W)—Y—Z, wherein W as $N_3$ and the method is described in claim 10. SR=synthetic resin, PB=purification beads; 1.) 4 eg. X-$T_b$-$V_a$-U(W)—Y—Z, 6 eq. Oxyma, 6 eq. DIEA, 2 h. 3.) Dissolution of crude peptide with DMSO and addition of 10 volume % of NaCitrate pH 4.5., 90 min. 4.) washing. 5.) PPh3 in MeCN/AcOH 9:1, 15 min. 6.) Washing with MeCN. 7) Hydrolysis with H$_2$O/TFA. 8.) 1,6- or 1,4-elimination. 9.) Final ether precipitation.

The peptide sequences were synthesized under standard solid phase peptide synthesis conditions, whereby the synthetic resin was treated with acetic anhydride and pyridine after each amino-acid coupling to block unreacted amino groups. Linker X1 was coupled to P1 on resin by usage of 4 eq. linker, 6 eq. oxyma and 6 eq. diisopropylamine (DIEA) in DMF for 2 h. The inventive method is shown in FIG. 1. Linker X2 was coupled to P1 and P2 on resin by usage of 4 eq. linker, 6 eq. oxyma and 6 eq. DIEA for 2 h. Thereafter, peptides were cleaved of the synthetic resin by a mixture of TFA/PhOH/PhSH/H$_2$O/ethanedithiol (EDT, 82.5:5:5:2.5) The crude peptide mixture was dissolved in Dimethylsulfoxide (DMSO). Aldehyde modified agarose beads were washed each 3× with water and NaCitrate buffer 0.1 M at pH 4.5. To the DMSO solutions of the peptides 10 vol. % of NaCitrate buffer was added, then the solution was applied to the agarose beads for 90 minutes, what immobilized the desired peptide quantitatively on the agarose beads. Subsequently washing each 3× was performed with 8 M urea, DMSO, EtOH/water (7:3), 0.1M NaCl, water, MeCN to remove any acetylated termination sequences and other impurities. The cleavage of the immobilized linker was carried out by treating the agarose resin with 50 mg PPh$_3$ per mL MeCN/AcOH (9:1). Afterwards the support was rinsed 4× with MeCN and a solution of H$_2$O/MeCN/TFA (70:29:1) was added for 180 min. Thereafter, the supernatant was filtered into a centrifuge tube and the support was rinsed 3× with TFA/H$_2$O (9:1) into the same tube. Et$_2$O was added 10-fold to initiate precipitation and the peptide was gained by centrifugation of the tube and disposal of the organic supernatant.

Figure 2:
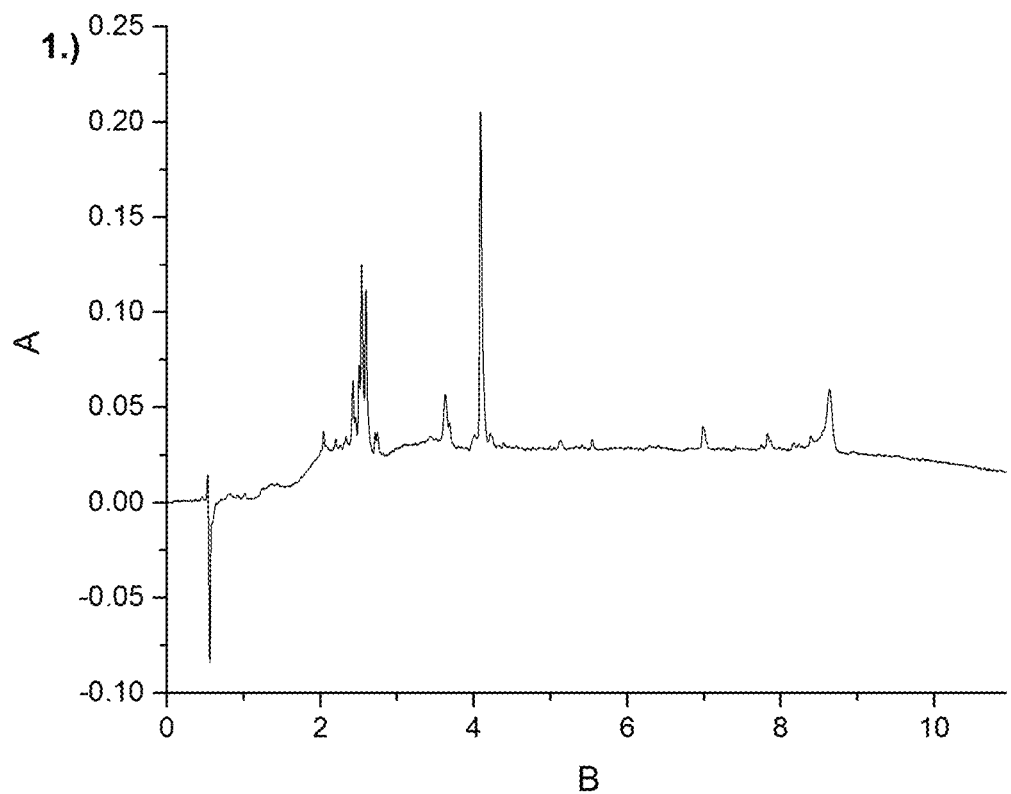
FIG. 2 shows an example of the inventive peptide purification of peptide P1 (H-ARTKQTARKSTGGKA-OH) (SEQ ID NO: 1) by usage of inventive linker molecule X1 and X2. A=absorption (210 nm), B=time/min; 1.) Chromatogram of crude peptide sample before linker coupling to P1. 2.) Chromatogram of P1 after purification by usage of linker X1 and method as described in claim 10. 3.) Chromatogram of P1 after purification by usage of linker X2 and method as described in claim 10.
Figure 2:
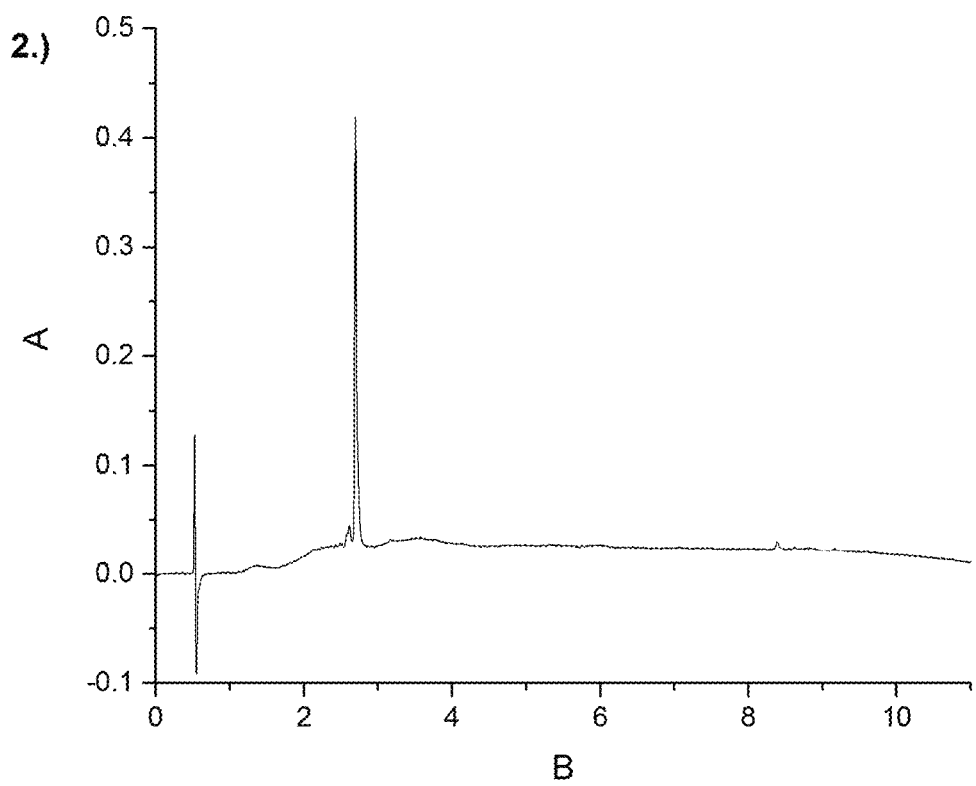
Figure 2:
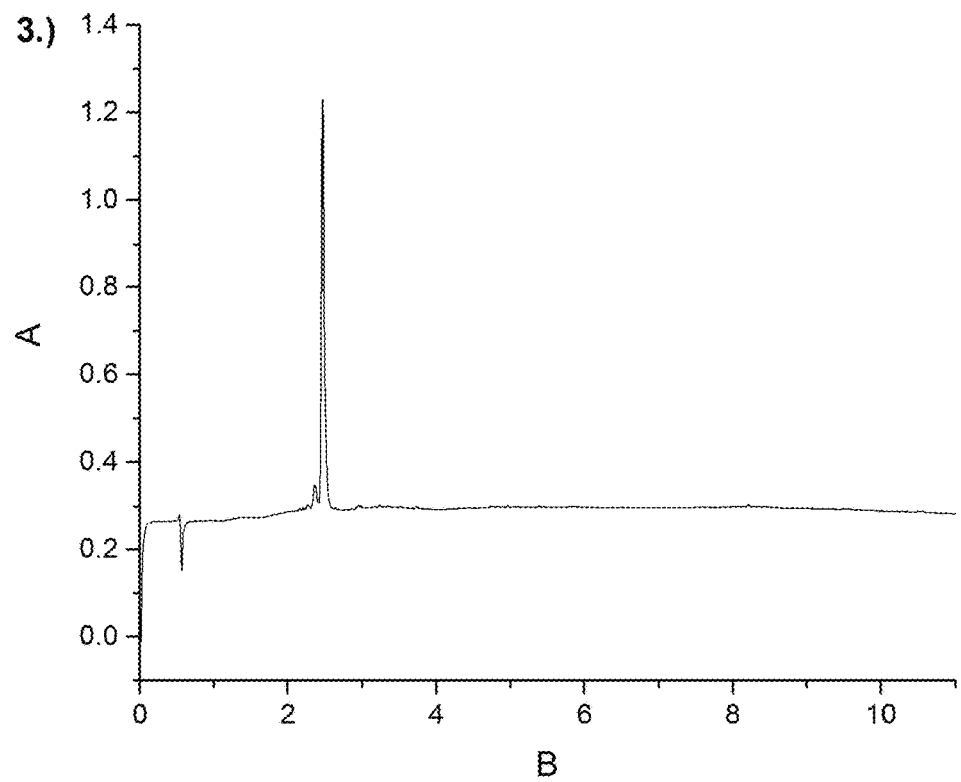
Figure 3:
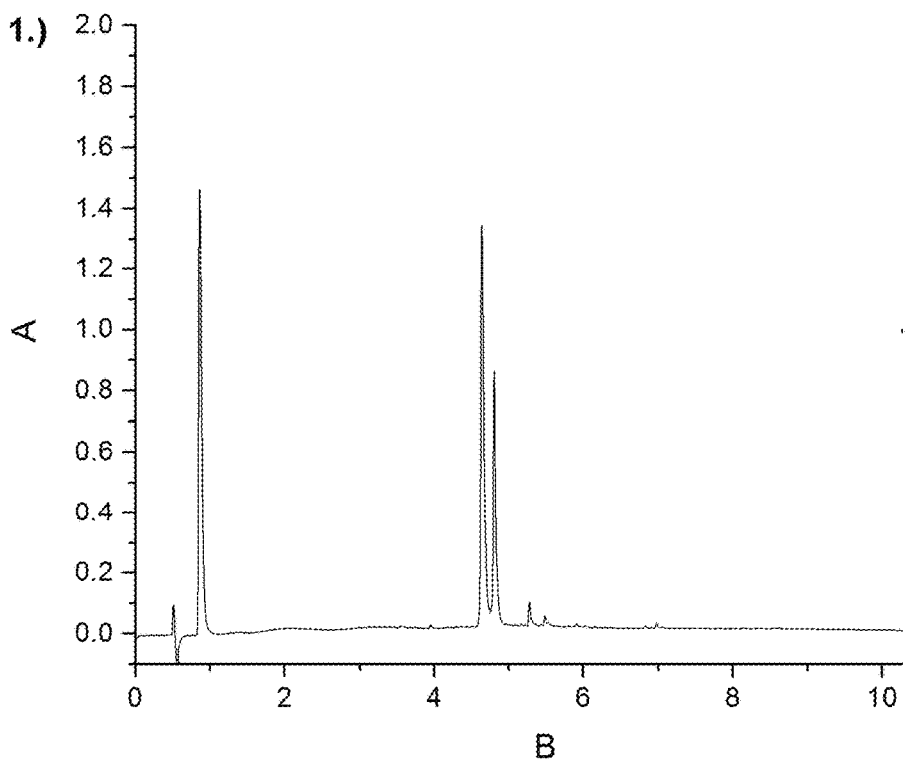
FIG. 3 shows an example of the inventive peptide purification of peptide P2 (H-AKADEVSLHKWYG-NH 2) (SEQ ID NO: 2) by usage of inventive linker molecule X2. A=absorption (210 nm), B=time/min; 1.) Chromatogram of crude peptide sample before linker coupling to P2. 2.) Chromatogram of P2 after purification by usage of linker X2 and method as described in claim 10. ~3-amino benzoic acid used as internal standard for peptide quantification.
Figure 3:
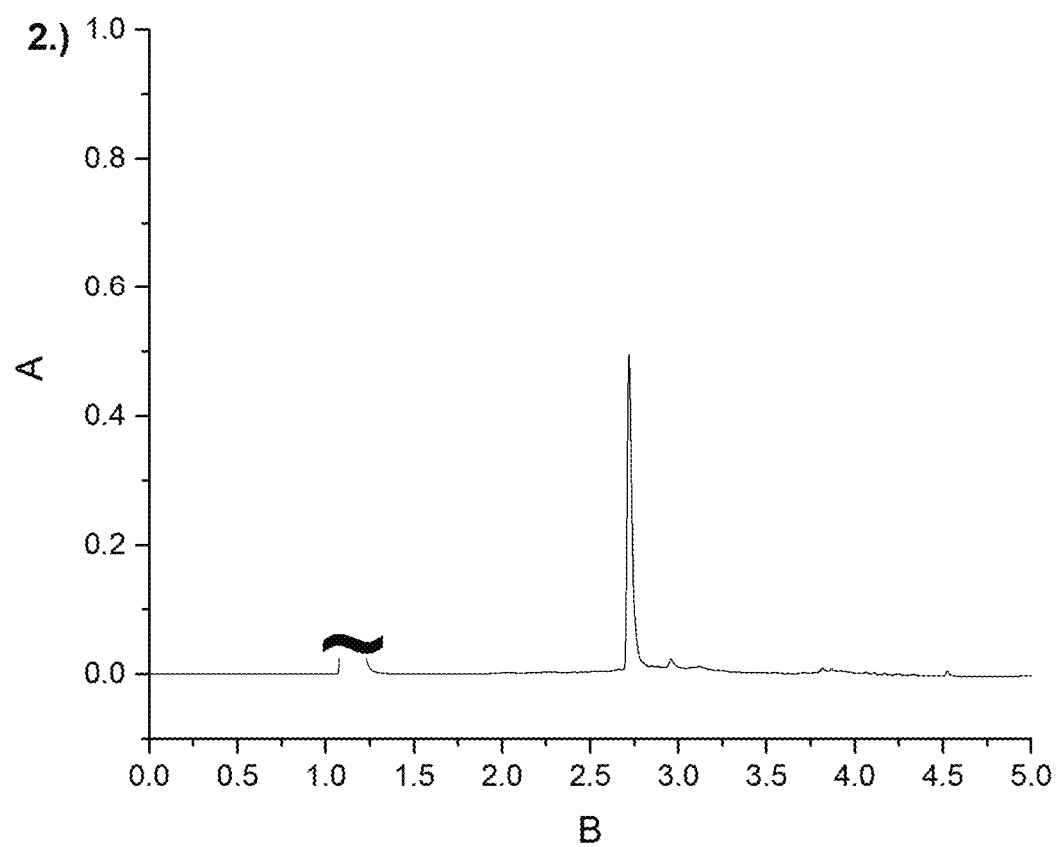

UPLC-MS was used to verify the purity of the individual phases. The UPLC-chromatograms of the non-purified (without linker molecule) and purified peptides are shown in FIG. 2 and FIG. 3, further results are summarized in Table 2. Identities of the peptides were confirmed by ESI-MS. The amount of 26 mg (recovery 62%) of Peptide P1 was gained by usage of X1 in a 93% purity (originally 41%) in the purification of 100 µmol P1. By usage of X2 linker 21 mg (recovery 50%) was gained in 93% purity. P2 was purified in 5 µmol scale by usage of X2 linker, whereby 4 mg (recovery 73%) was gained with a purity of 95% (originally 55%).

TABLE 2

| No. | sequence and linker | UV-purity crude | UV-purity purified/ recovery | calculated vs. found ESI mass |
|---|---|---|---|---|
| P1 (SEQ ID NO: 1) | H-ARTKQTARKSTGGKA-OH with X1 | 41% | 93%/62% | $MH^{2+}_{calc.}$: 780.95 m/z<br>$MH^{2+}_{found.}$: 780.63 m/z |
| P2 (SEQ ID NO: 2) | H-ARTKQTARKSTGGKA-OH with X2 | 55% | 93%/50% | $MH^{2+}_{calc.}$: 780.95 m/z<br>$MH^{2+}_{found.}$: 780.57 m/z |
| P1 (SEQ ID NO: 1) | H-AKADEVSLHKWYG-NH$_2$ with X2 | 41% | 95%/73% | $MH^{2+}_{calc.}$: 752.89 m/z<br>$MH^{2+}_{found.}$: 752.04 m/z |

Purity and recoveries of various peptides after application of the purification process according to the invention Example 2 of Linker Type 4: Purification of Naturally Occurring and Research Peptides (P3, P4, P5 and P6)

In a second set five peptides were synthesized. These were H-YFTGSEVENVSVNVH-NH$_2$ (SEQ ID NO: 3) (P3) a fragment 81-95 of the human cytomegalovirus lower matrix phosphoprotein (CMV), H-PSNPFYEALST-NH$_2$ (SEQ ID NO: 4) (P4) fragment 510-520 of humane Lemur Tyrosine Kinase 3 (LMTK3), H-DAEFRHDSGYEVHHQKLVFF-NH$_2$ (SEQ ID NO: 5) (P5) fragment 1-20 of humane amyloid beta and H-CKADEVSMHKWYG-NH$_2$ (SEQ ID NO: 6) (P6) a peptide sequence intended for research.

The peptide sequences P3, P4, P5 and P6 were synthesized in 100 µmol scale under standard solid phase peptide synthesis conditions, whereby the synthetic resin was treated with acetic anhydride and pyridine after each amino-acid coupling to block unreacted amino groups. Linker X1 was coupled to P3, P4, P5 and P6 on resin by usage of 4 eq. linker X1 (301 mg), 6 eq. oxyma (86 mg) and 6 eq. diisopropylamine (DIEA, 105 µL) for 2 h in 1.3 mL DMF.

Thereafter, peptides were cleaved of the synthetic resin by a mixture of TFA/PhOH/PhSH/H$_2$O/ethanedithiol (EDT, 82.5:5:5:5:2.5) and precipitated in cold diethylether. The crude peptide mixture was dissolved in 4.5 mL Dimethylsulfoxide (DMSO). Aldehyde modified agarose beads (1.5 mL settled beads) were washed each 3× with water and 0.1 M Na Citrate buffer at pH 4.5. To the DMSO solutions of the peptides 10 vol. % (500 µL) of NaCitrate buffer with 8 M guanidium hydrochloride was added. Then the solution was applied to the agarose beads for 90 minutes, what immobilized the desired peptides quantitatively on the agarose beads. Subsequently a 1 w % solution of L-cysteine in 0.1 M NaCitrate buffer at pH 4.5 was added directly to the immobilisation mixture for 15 min to block unreacted aldehyde groups. Afterwards, the purification media was washed each 3× with DMSO, 6 M guanidium hydrochloride, EtOH/water (7:3) with 0.1 M NaCl, water and MeCN to remove any acetylated termination sequences and other impurities. The cleavage of the immobilized linker was carried out by treating the agarose resin with 10 mL of 50 mg per mL PPh$_3$ MeCN/AcOH/H$_2$O (90:5:5). Afterwards the support was rinsed 3× with MeCN/H$_2$O (9:1) and 2 mL of a solution of H$_2$O/TFA (60:40) was added for 60 min. Thereafter, to the supernatant 2 mL TFA was added and the resulting mixture was filtered into a centrifuge tube and the support was rinsed 2× with TFA/H$_2$O (95:5) into the same tube. Et$_2$O was added 5-fold relative to the TFA-water amount to initiate precipitation and the peptide was gained by centrifugation of the tube and disposal of the organic supernatant.

Figure 4:
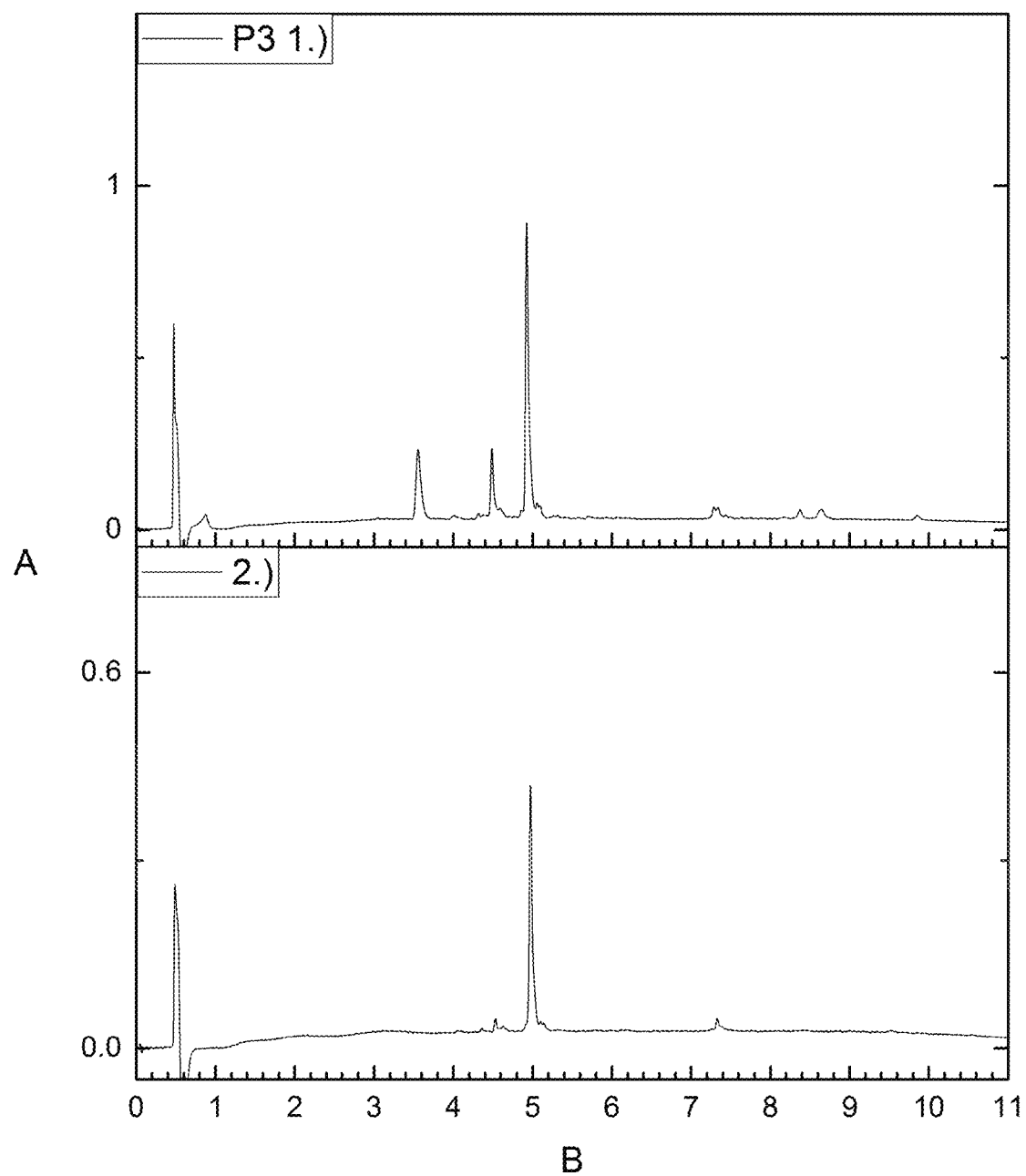
FIG. 4 shows four examples of the inventive peptide purification of peptides P3 (H-YFTGSEVENVSVNVH-NH$_2$) (SEQ ID NO: 3), P4 (H-PSNPFYEALST-NH$_2$) (SEQ ID NO: 4), P5 (H-DAEFRHDSGYEVHHQKLVFF-NH$_2$)
Figure 4:
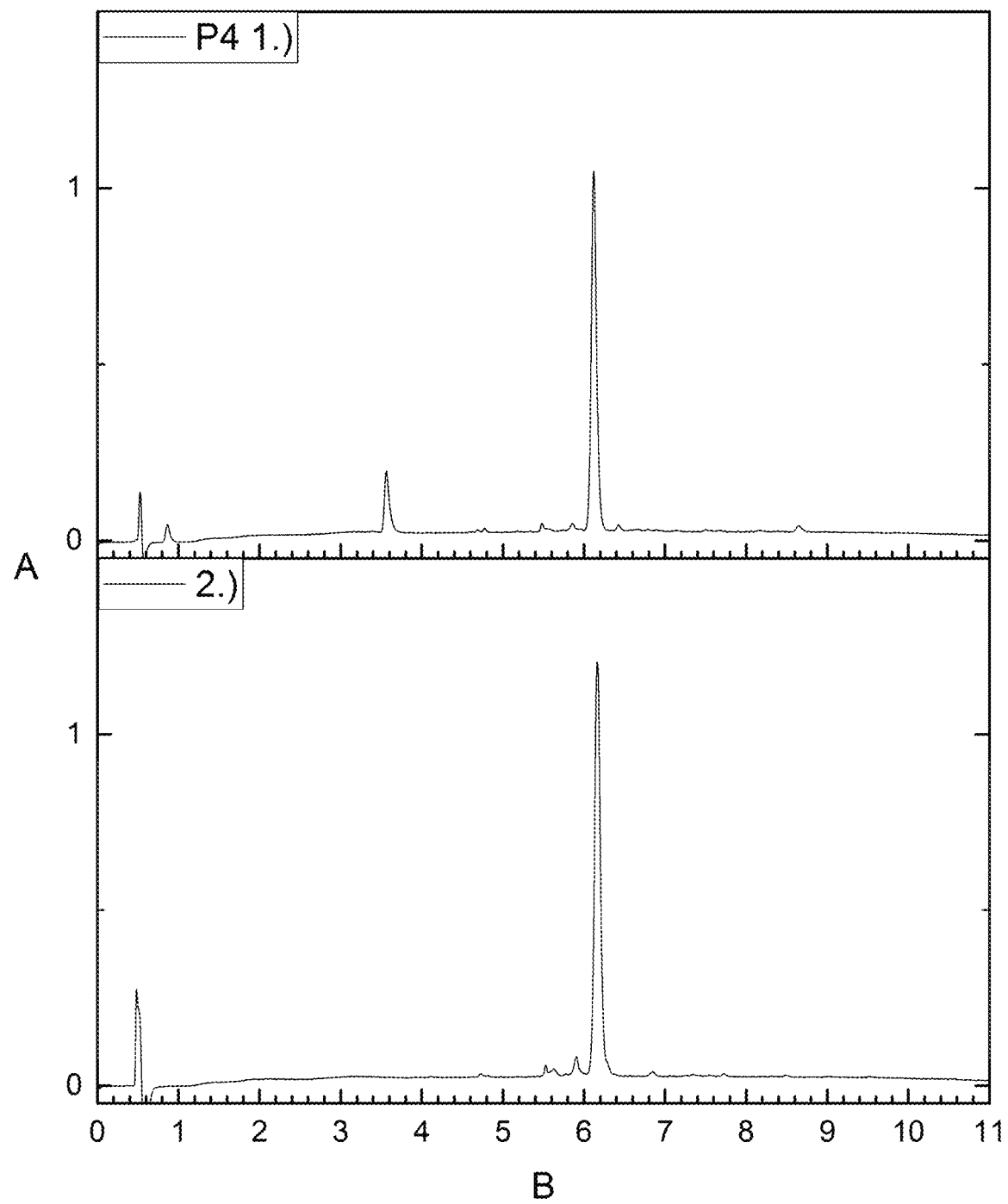
Figure 4:
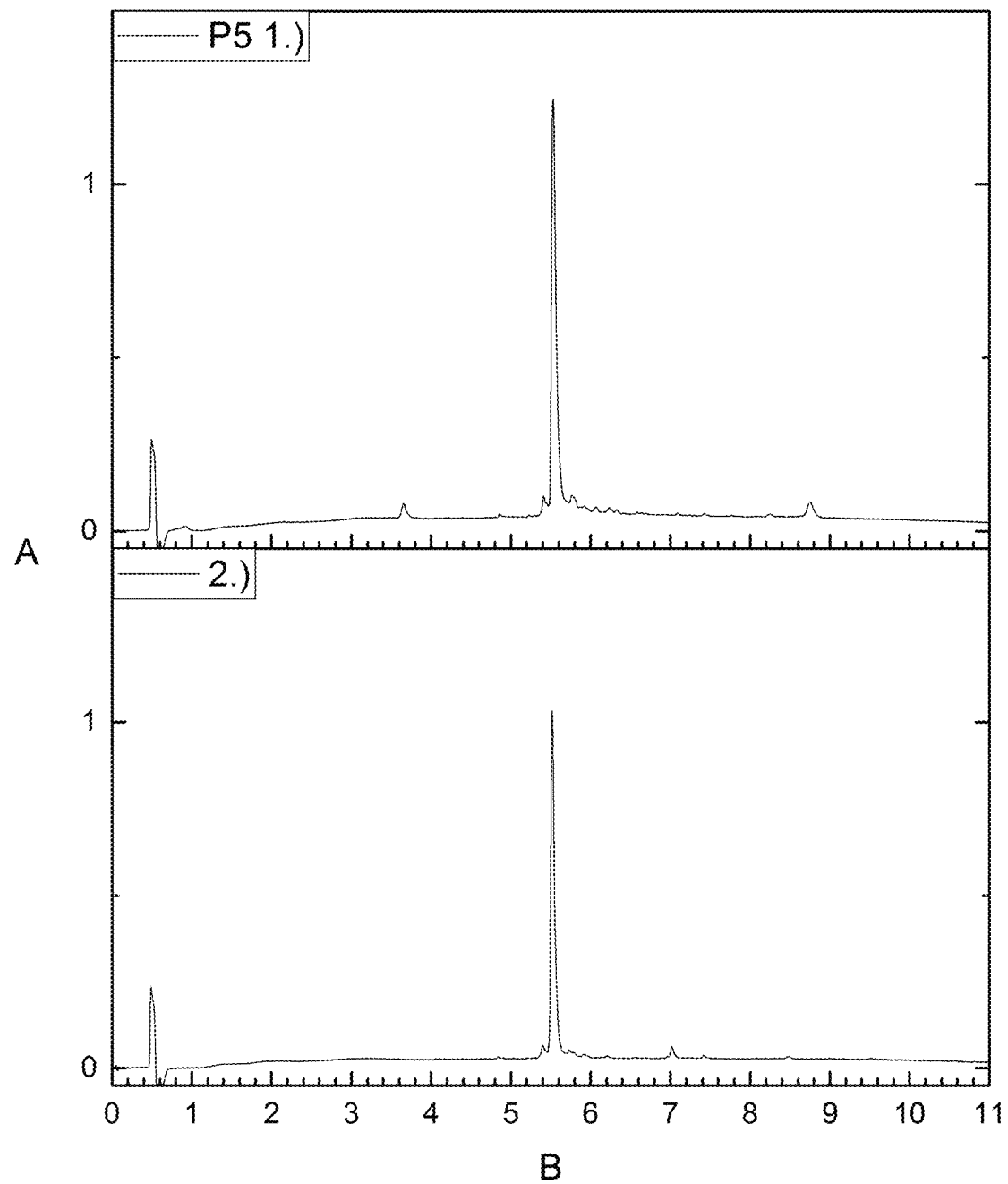
Figure 4:
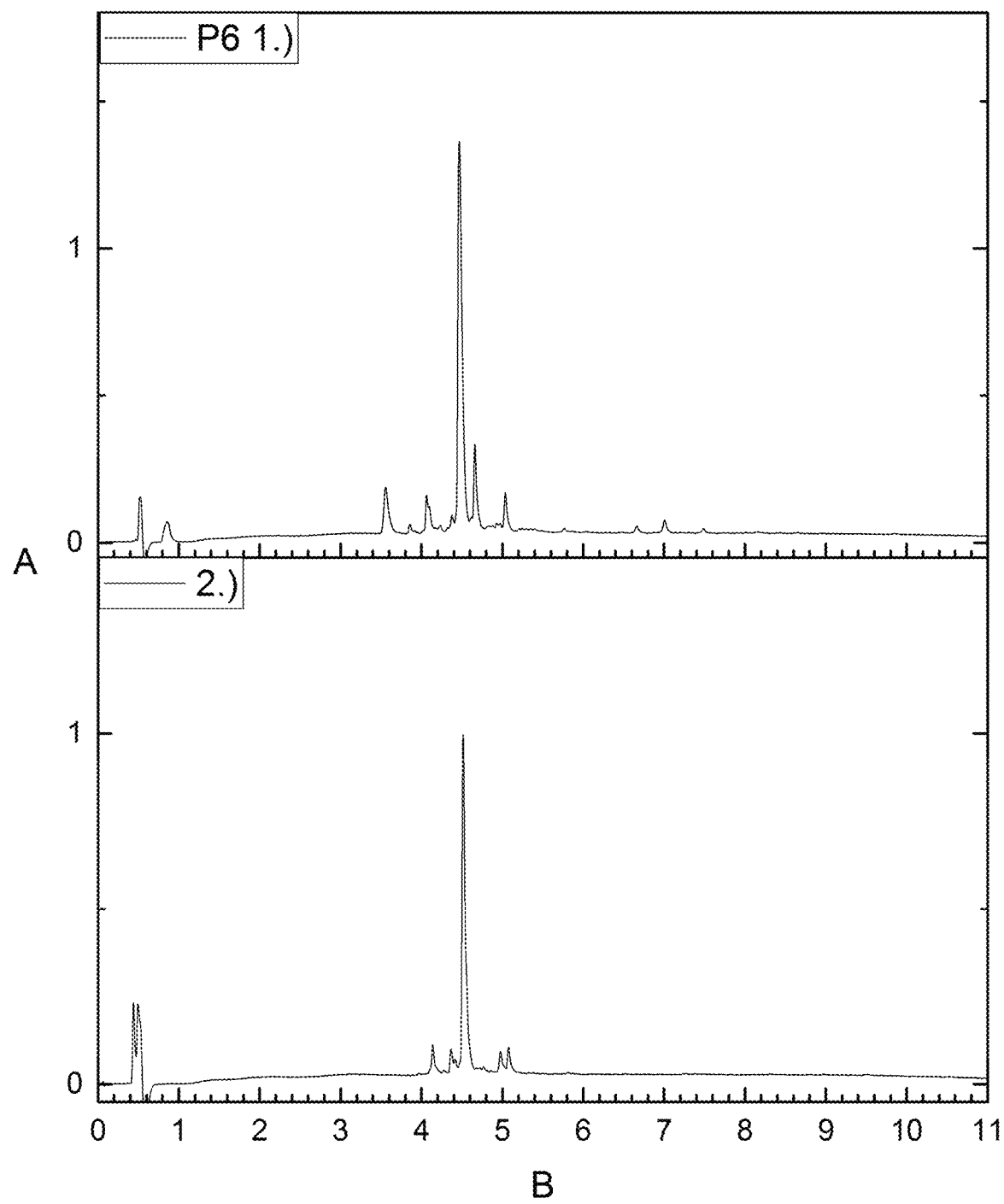

UPLC-MS was used to verify the purity of the individual phases. The UPLC-chromatograms of the non-purified (without linker molecule) and purified peptides are shown in FIG. 4. Identities of the peptides were confirmed by ESI-MS. The yielded peptide amounts after lyophilisation, the calculated recoveries and UV-purities before and after purification are given in Table 3.

TABLE 3

| No. | sequence and linker | UV-purity crude | UV-purity purified/ recovery | calculated vs. found ESI mass |
|---|---|---|---|---|
| P3 (SEQ ID NO: 3) | H-YFTGSEVENVSVNVH-NH$_2$ with X1 | 56% | 81%/74%, 36 mg | $MH^{2+}_{calc.}$: 840.41 m/z<br>$MH^{2+}_{found.}$: 840.50 m/z |
| P4 (SEQ ID NO: 4) | H-PSNPFYEALST-NH$_2$ with X1 | 78% | 91%/76%, 79 mg | $MH^{2+}_{calc.}$: 612.80 m/z<br>$MH^{2+}_{found.}$: 612.87 m/z |
| P5 (SEQ ID NO: 5) | H-DAEFRHDSGYEVHHQKLVFF-NH$_2$ with X1 | 60% | 87%/66%, 75 mg | $MH^{2+}_{calc.}$: 820.73 m/z<br>$MH^{2+}_{found.}$: 820.94 m/z |
| P6 (SEQ ID NO: 6) | H-CKADEVSMHKWYG-NH$_2$ with X1 | 60% | 74%/66%, 57 mg | $MH^{2+}_{calc.}$: 776.86 m/z<br>$MH^{2+}_{found.}$: 777.05 m/z |

Purity and recoveries of various peptides after application of the purification process according to the invention.

Example 1 of Type 1 Linker: Purification of Research Peptide P2

The inventive method for the purification of peptides with a type 1 linker was applied to peptide H-AKADEV-SLHKWYG-NH$_2$ (SEQ ID NO: 2) (P2), which is a peptide sequence intended for research.

The peptide was synthesized under standard solid phase peptide synthesis conditions, whereby the synthetic resin was treated with acetic anhydride and pyridine after each amino-acid coupling to block unreacted amino groups. Linker X9 of type 1 was coupled to P2 on resin using 4 eq. linker, 6 eq. oxyma and 6 eq. diisopropylamine (DIEA) in dimethylformamide (DMF) for 2 h. Thereafter, the peptide was cleaved off the synthetic resin by a mixture of TFA/TIS/DTT/H$_2$O (84:2:6:8) and precipitated in diethyl ether. 30 mg of linker modified peptide was gained. The inventive method for this linker type 1 is shown in FIG. 5. Of the crude peptide mixture 1.9 mg was dissolved in 100 μL Dimethylsulfoxide (DMSO). Aldehyde modified agarose beads were added to a cartridge with each 75 μL 50% bead suspension in H$_2$O/EtOH (4:1) slurry, thereafter the beads were washed 3× with water and 0.1 M NaCitrate buffer at pH 4.5. To the DMSO solutions of the peptides 10 vol. % (10 μL) of NaCitrate buffer with 7 M guanidium hydrochloride was added. Then 110 μL of this solution was applied to the agarose beads for 90 minutes, what immobilized the desired peptides quantitatively on the agarose beads (UPLC analysis of immobilization supernatant). Subsequently 100 μL of a 2 w % solution of L-cysteine in 0.1 M NaCitrate buffer at pH 4.5 was added to beads, after the immobilization mixture was filtered off for 15 min to block unreacted aldehyde groups and to reverse imine formation. Afterwards, the purification media was washed each 500 μL of 3× with DMSO with 0.9 M guanidium hydrochloride, EtOH/water (7:3) with 0.1 M NaCl, to remove any acetylated termination sequences and other impurities. The cleavage of the immobilized linker peptide was carried out by treating the agarose resin with 200 μL TCEP (25 mg/mL) per reactor for 30 min. Afterwards the support was rinsed 3× with H$_2$O containing 0.1% TFA. The peptide was released from the agarose by using the amine switch, thus 200 μL of a 0.2 M NH$_4$HCO$_3$ solution at pH 9 were added to the beads for 15 min. This deprotonated the piperazinyl moiety and released the peptide. The identity of desired peptide was confirmed by ESI/MS (FIG. 9, Table 4).

TABLE 4

| No. | sequence and linker | UV-purity crude | UV-purity purified/ recovery | calculated vs. found ESI mass |
|---|---|---|---|---|
| P2 (SEQ ID NO: 2) | H-AKADEV SLHKWYG-NH$_2$ with X9 | 77% | 48%/ 45% | MH$^{2+}_{calc.}$: 752.89 m/z MH$^{2+}_{found.}$: 752.89 m/z |

Purity and recoveries of the peptide after application of the purification process according to the invention

Example 1 of Type 2 Linker: Purification of Research Peptide P2

The inventive method for the purification of peptides with a type 2 linker was applied to peptide H-AKADEVSL-HKWYG-NH$_2$ (SEQ ID NO: 2) (P2), which is a peptide sequence intended for research.

The peptide was synthesized under standard solid phase peptide synthesis conditions, whereby the synthetic resin was treated with acetic anhydride and pyridine after each amino-acid coupling to block unreacted amino groups. Linker X13 was coupled to P2 on resin using 4 eq. linker, 6 eq. oxyma and 6 eq. diisopropylamine (DIEA) in dimethylformamide (DMF) for 3 h. The inventive method of this linker type 2 is shown in FIG. 6. Thereafter, the peptide was cleaved off the synthetic resin by a mixture of TFA/TIS/DTT/H$_2$O (84:2:6:8). The crude peptide mixture was dissolved in dimethyl sulfoxide (DMSO). Aldehyde modified agarose beads were washed each 3× with water and 0.1 M NaCitrate buffer at pH 4.5. 10 vol. % of 6 M GdmCl in the NaCitrate buffer were added to the DMSO solution of the peptide. The resulting solution was added to the agarose beads and the mixture was shaken for 90 minutes to immobilize the desired peptide quantitatively onto the agarose beads. The supernatant was removed and the residue was treated with 1 w. % L-Cys in NaCitrate buffer for 15 min. Subsequently, the beads were washed each 3× with DMSO, 6 M aqueous GdmCl, EtOH/0.1 M NaCl (7:3), water, MeCN, 0.1 vol. % TFA in EtOH to remove any acetylated termination sequences and other impurities. The cleavage of the immobilized linker was carried out by treating the agarose resin with 10 eq. SnCl$_2$ in EtOH (0.5 M) for 3 h. Afterwards, the support was rinsed each 3× with 0.1 vol. % TFA in EtOH, 0.1 vol. % TFA in H$_2$O, MeCN/H$_2$O (9:1). A solution of 0.2 M aqueous NH$_4$HCO$_2$ at pH 8.85/MeCN (1:1) was added for 15 min. The supernatant was filtered into a centrifuge tube and the support was rinsed 2× with H$_2$O into the same tube. The purified peptide was obtained by lyophilization of the residue.

UPLC-MS was used to verify the purity of the individual steps. The UPLC-chromatograms of the non-purified (without linker molecule) and purified peptide are shown in FIG. 9. Identities of the peptide were confirmed by ESI-MS (Table 5). 36 mg (recovery 73%) peptide P2 with a final purity of 97% (originally 77%) were obtained using X13 and 50 μmol crude P2 in a purification experiment.

TABLE 5

| No. | sequence and linker | UV-purity crude | UV-purity purified/ recovery | calculated vs. found ESI mass |
|---|---|---|---|---|
| P2 (SEQ ID NO: 2) | H-AKADEV SLHKWYG-NH$_2$ with X13 | 77% | 97%/ 73% | MH$^{2+}_{calc.}$: 752.89 m/z MH$^{2+}_{found.}$: 752.31 m/z |

Purity and recoveries of the peptide after application of the purification process according to the invention

Example 1 of Type 3 Linker: Purification of Research Peptide P2

The inventive method for the purification of peptides with a type 3 linker was applied to peptide H-AKADEVS-LHKWYG-NH$_2$ (SEQ ID NO: 2) (P2), which is a peptide sequence intended for research.

The peptide was synthesized under standard solid phase peptide synthesis conditions, whereby the synthetic resin was treated with acetic anhydride and pyridine after each amino-acid coupling to block unreacted amino groups.

Linker X22 of type 3 was coupled to P2 on resin using 4 eq. linker, 3.6 eq. 2-(6-Chlor-1H-benzotriazol-1-yl)-1,1,3,3-tetramethylaminium-hexafluorophosphat (HCTU), 4 eq. Oxyma and 8 eq. diisopropylamine (DIEA) in dimethylformamide (DMF) for 2 h. Thereafter, the peptide was cleaved off the synthetic resin by a mixture of TFA/TIS/DTT/H$_2$O (84:2:6:8) and precipitated in diethyl ether. 27 mg of linker modified peptide was gained. The inventive method for this linker type 3 is shown in FIG. 7. Of the crude crude peptide mixture 2.1 mg was dissolved in 100 µL Dimethylsulfoxide (DMSO). Aldehyde modified agarose beads were added to a cartridge with each 75 µL 50% bead suspension in H$_2$O/EtOH (4:1) slurry, thereafter the beads were washed 3× with water and 0.1 M NaCitrate buffer at pH 4.5. To the DMSO solutions of the peptides 10 vol. % (10 µL) of NaCitrate buffer with 7 M guanidium hydrochloride was added. Then 110 µL of this solution was applied to the agarose beads for 90 minutes, what immobilized the desired peptides quantitatively on the agarose beads (UPLC analysis of immobilization supernatant). Subsequently 100 µL of a 2 w % solution of L-cysteine in 0.1 M NaCitrate buffer at pH 4.5 was added to beads, after the immobilization mixture was filtered off for 15 min to block unreacted aldehyde groups and to reverse imine formation. Afterwards, the purification media was washed each 500 µL of 3× with DMSO with 0.9 M guanidium hydrochloride, EtOH/water (7:3) with 0.1 M NaCl, to remove any acetylated termination sequences and other impurities. The cleavage of the immobilized linker peptide was carried out by treating the agarose resin with 200 µL TCEP (25 mg/mL) per reactor for 30 min. Afterwards the support was rinsed 3× with H$_2$O containing 0.1% TFA. The peptide was released from the agarose by using the amine switch with nucleophilic release, thus 200 µL of a 0.2 M NEt$_3$ in water solution at pH 7 were added to the beads for 100 h. This deprotonated the piperazinyl and aniline —NH$_3^+$ moiety then released the peptide by nucleophilic attack of the aniline —NH$_2$. The identity of desired peptide was confirmed by ESI/MS (FIG. 9, Table 6).

TABLE 6

| No. | sequence and linker | UV-purity crude | UV-purity purified/ recovery | calculated vs. found ESI mass |
|---|---|---|---|---|
| P2 (SEQ ID NO: 2) | H-AKADEV SLHKWYG-NH$_2$ with X22 | 77% | 26%/ 20% | MH$^{2+}_{calc.}$: 752.89 m/z MH$^{2+}_{found.}$: 752.23 m/z |

Purity and recoveries of the peptide after application of the purification process according to the invention

Chemical Synthesis of Carbamate Switch (Type 4) Linker Molecules X1 and X2

Synthetic Steps for the Synthesis of 2-((2-(2-bis-(tert-Butoxycarbonyl)-(aminooxy)acetamido) ethyl)carbamoyl)-4-azido-3-bromobenzyl (4-nitrophenyl) carbonate (X1)

6-Amino-7-Bromophthalide

To a cooled solution (0° C.) of 6-aminophthalide (5.13 g, 34.05 mmol) in THF (80 mL) was added N-bromosuccinimide (6.12 g, 34.05 mmol, 1 eq). The cooling bath was removed and the solution stirred for 1 h, then the solvent was removed under reduced pressure. The yellow residue was taken up in ethyl acetate (400 ml) and washed three times with water (200 mL each). The organic phase was dried over magnesium sulfate, filtered and the solvent removed under reduced pressure to give 6-amino-7-bromophthalide as a brown solid (6.53 g, 28.63 mmol, 84%). R$_f$=0.2 (cyclohexane/ethyl acetate 2:1); UPLC-MS: t$_R$=1.45 min (gradient 10-90% B in 5 min); UPLC-purity (210 nm)=83.1%; ESI-MS: (calculated MH$^+$: 227.97, 229.96, found: 228.01, 230.01)

6-azido-7-Bromophthalide

6-Amino-5-bromophthalide (5.54 g, 24.17 mmol) was added to 0° C. cold hydrochloric acid (1 M, 100 mL). To the cooled suspension was dropwise added conc. sulfuric acid while stirring until the solid was completely dissolved (25 mL), the solution was further cooled until it reached 0° C. again. A solution of sodium nitrite (3.34 g, 48.34 mmol, 2 eq.) in water (17 mL) was added slowly (formation of nitrous gases if solution too warm). After stirring for 10 minutes, a solution of sodium azide (3.14 g, 48.34 mmol, 2 eq). in water (20 mL) was slowly added dropwise (caution: formation of hydrazoic acid). After 30 min, the suspension was extracted with ethyl acetate (200 mL). The aqueous phase was filtered and the filter cake was washed three times with water (100 mL each) and once with cyclohexane (150 mL). 6-azido-7-bromophthalide (6.58 g (94%), 24.17 mmol, quant.) was obtained as a yellow solid. R$_f$=0.3 (cyclohexane/ethyl acetate 2:1); UPLC-MS: t$_R$=2.24 min (gradient 10-90% B in 5 min); UPLC-purity (210 nm)=50.3%

N-(2-(2-bis-(tert-Butoxycarbonyl)-(aminooxy)acetamido)ethyl)-3-azido-2-bromo-6-(hydroxymethyl)benzamide 6-Azido-7-bromophthalide (5.54 g (94%), 24.17 mmol) was taken up in acetonitrile (150 mL) and the suspension heated to 50° C. with stirring. Ethylenediamine (23.4 mL, 350.47 mmol, 14.5 eq.) was added, thus solid completely dissolved after 10 minutes. After 1 h stirring at 50° C., the solvent and excess ethylenediamine were removed under reduced pressure to give a red oil as a residue (8.49 g). Saturated brine (80 mL) was added, the resulting suspension was sonicated for 30 min, stirred at 40° C. for 30 min, and filtered. The filter cake was washed once with saturated brine (50 mL) and once with cyclohexane (100 mL). After drying the filter cake, the title compound was obtained as a yellow solid (3.84 g, 12.2 mmol, 50.6%). Product 3 was also obtained from the filtrate by extraction with ethyl acetate (six times with 150 ml each time) (4.79 g, 15.22 mmol, 63.1%). R$_f$=0.1 (DCM/MeOH 8:2); UPLC-MS: t$_R$=1.03 min (gradient 10-90% B in 5 min); UPLC-purity (210 nm)=83.5%; ESI-MS: (calculated MNa$^+$: 336.01, 338.01 g/mol, found: 335.95, 337.96 m/z).

N-(2-(2-bis-(tert-Butoxycarbonyl)-(aminooxy)acetamido)ethyl)-3-azido-2-bromo-6-(hydroxymethyl)benzamide To a stirred solution of bis-(tert-butoxycarbonyl)-(aminooxy)acetic acid ((Boc)$_2$AOAc-OH, 4.71 g, 15.86 mmol, 1.3 eq.) and NHS (1.84 g, 15.86 mmol, 1.3 eq.) in acetonitrile (40 mL) is added dicyclohexylcarbodiimide (DCC, 3.30 g, 15.86 mmol, 1.3 eq.). After stirring for 1 h, the solution is separated from the resulting white precipitate by filtration and the filter cake is washed with acetonitril (40 mL). The filtrate is diluted to 120 mL with acetonitrile. N-(2-(2-bis-(tert-Butoxycarbonyl)-(aminooxy)acetamido)ethyl)-3-azido-2-bromo-6-(hydroxymethyl)benzamide (3.79 g, 12.06 mmol, 1 eq) is taken up in acetonitrile (30 mL) and the suspension is sonicated for 50 min. The filtrate with (Boc)$_2$AOAc-NHS is then added to this suspension and the reaction mixture is stirred for 2.5 hours. After removal of the solvent under reduced pressure, ethyl acetate (150 ml) is added to the resulting orange oil (10.47 g) and the suspension is sonicated for 10 minutes and stirred at 50° C. for 10 minutes. After the suspension was washed, (three times with 80 mL 5 w % NaHCO$_3$ solution (pH 8), once with 80 mL 2% citric acid solution (pH 4.5) and twice with 80 mL brine), the organic phase was separated and dried with magnesium sulfate and the solvent was removed under reduced pressure, a yellow foam was obtained as a crude product (6.84 g). After drying the crude product under high vacuum, the product was obtained as a yellow solid (6.43 g, 75.89% purity (determined with UV/vis), 8.31 mmol, 68.91% yield). Rf=0.15 (DCM/MeOH 95:5); UPLC-MS: $t_R$=2.60 min (10-90% MeCN in 3 min), UPLC-purity (21 nm)=79.1%, ESI-MS: (calculated MNa$^+$: 609.13, 611.13 g/mol, found: 609.03, 611.06 m/z).

2-((2-(2-bis-(tert-Butoxycarbonyl)-(aminooxy)acetamido)ethyl)carbamoyl)-4-azido-3-bromobenzyl (4-nitrophenyl) carbonate N-(2-(2-bis-(tert-Butoxycarbonyl)-(aminooxy)acetamido)ethyl)-3-azido-2-bromo-6-(hydroxymethyl) benzamide (6.39 g (79%), 8.26 mmol) was dissolved in DCM (20 mL) and cooled to 0° C. To the solution was first added anhydrous pyridine (1.00 mL, 12.48 mmol, 1.5 eq.) with stirring and then slowly a solution of p-nitrophenyl chloroformate (2.52 g, 12.48 mmol, 1.5 eq.) in DCM (20 mL). The reaction mixture was warmed to room temperature and stirred for 1 h. Under reduced pressure, the solvent is removed and the resulting orange oil (9.99 g) is dissolved in 150 mL ethyl acetate. The suspension was filtered, and the solvent was removed from the filtrate under reduced pressure to give a yellow foamy solid as a crude product (8.85 g). After purification by column chromatography (silica gel, cyclohexane: ethyl acetate 2:1 to 1:1), the product (3.82 g) was taken up in 100 mL diethyl ether, treated with ultrasound for 10 min, stirred for 30 min at 40° C. and then overnight at −20° C. stored. The product was filtered and washed with 100 mL −20° C. cold diethyl ether and dried after high vacuum as a pale-yellow solid (2.47 g, 3.29 mmol, 39.5%).

$R_f$=0.25 (Ethyl acetate/Cyclohexane 2:1), UPLC-MS: $t_R$=3.18 min (10-90% MeCN in 5 min), UPLC-purity (278 nm)=88.4%, ESI-MS: (calculated MNa$^+$: 774.13, 776.13 g/mol, found: 773.91, 775.88 m/z).

$^1$H NMR (500 MHz, DMSO) δ8.71 (s, 1H), 8.32 (d, J=9.2 Hz, 2H), 7.95 (s, 1H), 7.62 (d, J=8.3 Hz, 1H), 7.57 (d, J=9.2 Hz, 1H), 7.52 (d, J=8.3 Hz, 1H), 5.25 (s, 2H), 4.36 (s, 2H), 3.33 (m, 4H), 1.46 (s, 18H).

Synthetic Steps for the Synthesis of 2-((2-(2-bis-(tert-Butoxycarbonyl)-(aminooxy)acetamido) ethyl) carbamoyl)-4-azido-3,5-dibromobenzyl (4-nitrophenyl) carbonate (X2)

5,7-Dibromo-6-Aminophthalide

6-Aminophthalide (20.00 g, 132.75 mmol) was provided in a 1 L round bottom flask with a stirring bar and 550 mL THF and 30 mL MeCN was added at 0° C. To the solution N-bromosuccinimide was added slowly as a solid through a powder funnel after which the solution turned brownish. The ice-bath was removed then after some time the solution turned yellow. After 2 h stirring at room-temperature UPLC-MS and TLC indicated complete conversion to the dibromide. The solvent was removed under reduced pressure at a rotational evaporator. The remaining solid was dissolved in 600 ml Ethyl acetate and washed 3 times with water. The organic phase was dried with MgSO$_4$ and after evaporation 39.86 g (129.86 mmol, 98%) of the desired product was gained as a pale yellow solid. $R_f$=0.6 (cyclohexanes/Ethyl acetate 2:1), UPLC-MS: $t_R$=2.36 min (10-90% MeCN in 3 min), UPLC-purity (254 nm)=87.0%, ESI-MS: (calculated M$^+$: 307.95 g/mol, found: 307.76 m/z).

5,7-Dibromo-6-Azidophthalide 5,7-Dibromo-6-aminophthalide (38.50 g, 124.18 mmol) was dissolved in 200 mL concentrated H$_2$SO$_4$ in a 2 L flask, the brown solution was cooled with a big ice bucket then it was slowly added 235 mL 1 M HCl, a precipitate formed during HCl addition. NaNO$_2$ (17.31 g, 248.35 mmol, 2 eq) was dissolved in 32 mL water and was added slowly to the suspension after it reached 5° C. The precipitate dissolved thereafter. The solution was further stirred for 15 min at 0° C. and subsequently, NaN$_3$ (16.31 g, 248.35 mmol, 2 eq) in 75 mL water was added dropwise by Pasteur pipette. Strong formation of gases (N$_2$, HN$_3$) was observed. The foamy solution was stirred for 1 h, thereafter 500 ml water was added under cooling with ice. After foam-building had ceased and solution had reached room-temperature the suspension was filtered by the use of a Büchner funnel, while 2 L of water was used to transfer the solid into the funnel and thereby wash the solid. After drying the wet product in a crystallizing dish under reduced pressure, the product was yielded as a slightly brownish solid (36.01 g, 108.16 mmol, 87.1%). $R_f$=0.45 (cyclohexanes/Ethyl acetate 2:1), UPLC-MS: $t_R$=2.89 min (10-90% MeCN in 3 min), UPLC-purity (254 nm)=95.3%, N-(2-aminoethyl)-3-azido-2,4-dibromo-6-(hydroxymethyl)benzamide 5,7-Dibromo-6-azidophtalide (18.00 g, 53.52 mmol) was dissolved in Ethyl acetate (490 mL) insoluble impurities were filtered off and ethylenediamine (52.73 mL, 749.32 mmol, 14 eq) was added at 0° C. The reaction was stirred at room temperature for 1 h, after which UPLC-MS showed quantitative conversion. The reaction mixture was transferred into a separation funnel to which 100 mL Brine was added. After separation of the aqueous phase the organic phase was dried with MgSO$_4$ and the desired product was gained after evaporating the organic solvent on rotational evaporator as an orange solid. (20.50 g, 52.16 mmol, 97.4%). $R_f$=0.25 (DCM/MeOH 8:2), UPLC-MS: $t_R$=1.80 min (10-90% MeCN in 3 min), UPLC-purity (254 nm)=84.2%, ESI-MS: (calculated M$^+$: 393.93 g/mol, found: 393.87 m/z).

N-(2-(2-bis-(tert-Butoxycarbonyl)-(aminooxy)acetamido)ethyl)-3-azido-2,4-dibromo-6-(hydroxymethyl)benzamide Bis-(tert-Butoxycarbonyl)-(aminooxy)acetic acid ((Boc)$_2$AOAcOH, 17.30 g, 58.18 mmol, 1.1 eq.) and N-hydroxysuccinimide (NHS, 6.76 g, 58.18 mmol, 1.1 eq.) was dissolved in 350 mL Acetonitril. To this solution was added dicyclohexylcarbodiimide (DCC, 12.13 g, 58.18 mmol, 1.1 eq.) as a solid, after dissolution of DCC a white precipitate formed. The reaction mixture was stirred for 1 h at room temperature where the (Boc)$_2$AOAc-NHS ester was quantiatively formed according to UPLC-MS. Thereafter the mixture was filtered into a 1 L flask to remove the DCC-urea. N-(2-aminoethyl)-3-azido-2,4-dibromo-6-(hydroxymethyl)benzamide (20.5 g, 52.90 mmol) was dissolved in 530 mL Ethyl acetate and subsequently added to the solution of (Boc)$_2$AOAc-NHS. The mixture was stirred at room temperature for 1 h after which the completion of the reaction was confirmed by TLC and UPLC-MS. Additional formed precipitate was filtered off and the organic phase was washed 2× with 5% NaHCO$_3$ (each 200 mL), 1× brine and 2×2% citric acid solution(pH 4.5)/brine 1:1 (each 150 mL). The organic phase was dried with MgSO$_4$ and hence, the organic solvent was removed in vacuo and the title compound was obtained as a pale yellow oil (37.70 g, 56.58 mmol, quantitativ). R$_f$=0.4 (DCM/MeOH 95:5), UPLC-MS: t$_R$=2.97 min (10-90% MeCN in 3 min), UPLC-purity (254 nm)=54.2%, ESI-MS: (calculated M$^+$: 667.05, MNa$^+$: 689.04 g/mol, found: 688.95 m/z).

2-((2-(2-bis-(tert-Butoxycarbonyl)-(aminooxy)acet-amido)ethyl)carbamoyl)-4-azido-3,5-dibromobenzyl (4-nitrophenyl) carbonate N-(2-(2-bis-(tert-Butoxycarbonyl)-(aminooxy)acet-amido)ethyl)-3-azido-2,4-dibromo-6-(hydroxymethyl)benzamide (37.70 g (94%), 52.90 mmol was provided in CH$_2$Cl$_2$ (170 mL) and (dry, stored over molecular sieve) pyridine (4.72 mL, 58.50 mmol, 1.1 eq) was added. Thereafter, 4-nitrophenylchloroformiate (12.03 g, 58.50 mmol, 1.1 eq) was added slowly as a solid at room temperature keeping temperature constant by usage of a water bath. Reaction may cause DCM to evaporate at the center of the flask. Indicated by LCMS and TLC indicated a complete reaction after 1 h. Dichloromethane was removed in vacuo yielding 52 g crude brown oil and the residue was dissolved in 500 mL ethyl acetate and washed 2× 2% citric acid solution (pH 4.5)/brine 1:1 (each 250 mL) and 1× brine 150 mL. The organic phase was dried by usage of MgSO$_4$. Afterwards this suspension was filtered over a 50 g silica plug in a glass frit, whereas the orange and reddish impurities remained on silica. The organic solvent was removed from the filtrate under reduced pressure till a highly viscous slightly amber oil remained. To this oil 70 ml of Et$_2$O was added and the two-phasic emulsion was turned on a rotational evaporator at 45° C. for 10 min till one homogeneous phase was formed. A small sand corn was added to the flask as a crystallization initiator and the flask was put in a refrigerator overnight (16 h). In the flask a sluggish precipitate had formed. Further 200 mL of cold (−25° C.) ether was added to the flask and the flask was gently shaken and stirred in an ice-bath. The white star-like crystals were transferred and washed with additional 200 mL cold Et$_2$O into a paper filter filled Büchner-funnel. Thus, yielding the title compound as a white solid (29.95 g, 36.02 mmol, 68.1%). R$_f$=0.6 (Ethyl acetate/Cyclohexane 2:1), UPLC-MS: t$_R$=2.86 min (30-95% MeCN in 3 min), UPLC-purity (278 nm)=93.5%, ESI-MS: (calculated MH$^+$: 832.06, MNa$^+$: 854.04 g/mol, found: 853.87 m/z).

$^1$H NMR (400 MHz, DMSO) δ8.73 (s, 1H), 8.33 (d, J=9.1 Hz, 2H), 7.93 (s, 1H), 7.57 (d, J=9.1 Hz, 2H), 5.24 (s, 2H), 4.36 (s, 2H), 3.40-3.32 (m, 4H), 1.46 (s, 18H).

Chemical Synthesis of Amine Switch with Azide Reductive Safety Lock (Type 1) Linker Molecules X6 and X9

Synthetic Steps for the Synthesis of 3-((4-(2-bis-(tert-Butoxycarbonyl)-(aminooxy)acetyl)piperazin-1-yl)methyl)-4-azidobenzyl(4-nitrophenyl) carbonate (X6)

4-Nitro-3-(piperazin-1-ylmethyl)benzoic acid

4-Nitro-3-methylbenzoic acid methyl ester (5.03 g, 25.50 mmol) was dissolved in 170 mL dry Benzene in a 500 mL round bottom flask with a stirring bar. N-Bromosuccinimide (5.27 g, 29.33 mmol) and Benzoyl peroxide (0.62 g, 2.55 mmol) were added and the solution was heated to reflux. After 12 h UPLC-UV/vis indicated only 10% conversion to the brominated starting material. Again, N-Bromosuccinimide (3.66 g, 20.56 mmol) and Benzoyl peroxide (0.62 g, 2.55 mmol) were added. After 36 h UPLC-UV/vis indicated a conversion of 80%. The mixture was concentrated in vacuo and 85 mL Chloroform was added. It was slowly filtrated to a mixture of Piperazine (8.87 g, 102.00 mmol) and K$_2$CO$_3$ (4.63 g, 33.15 mmol) in 85 mL Chloroform in a 500 mL round bottom flask with a stirring bar. After 2 h UPLC-UV/vis indicated complete conversion to the desired product. With a rotational evaporator the solvent was removed. To the residue was added 250 mL Ethyl acetate and the mixture was filtrated to a separation funnel. The organic phase was washed three times with 100 mL saturated NaHCO$_3$ and three times with 100 mL Brine. After drying the organic phase over MgSO$_4$ and evaporation 7.3 g (not completely dry) of the desired product was obtained as a yellow oil. UPLC-MS: tR=1.602 min (10-90% MeCN in 3 min), UPLC-purity (278 nm)=68.3%, ESI-MS: (calculated MH+: 280.12 g/mol, found: 280.11 m/z).

(4-nitro-3-(piperazin-1-ylmethyl)phenyl)methanol

4-Nitro-3-(piperazin-1-ylmethyl)benzoic acid (1.10 g, assumed 3.00 mmol) was dissolved in 8 mL THF in a 250 mL round bottom flask and stirred at RT with a magnetic stirring bar. LiCl (0.77 g, 18.00 mmol), NaBH$_4$ (0.69 g, 18.00 mmol) and 16 mL Ethanol were added successively. After 12 h UPLC-UV/vis indicated complete conversion of the starting material. The reaction mixture was concentrated in vacuo and the residue was suspended in 60 mL Ethyl acetate. While stirring the mixture rapidly 25 mL 1 M NH$_4$Cl was added dropwise. After 2 h 25 mL 1 M NaOH was added slowly and the mixture was transferred to a separation funnel. The layers were separated, and the aqueous phase was extracted twice with 50 mL Ethyl acetate and twice with 50 mL Chloroform. The combined organic layers were dried over MgSO$_4$ and after evaporation of the organic solvent the desired product was obtained as a yellow solid (0.59 g, 2.35 mmol, 88%). UPLC-MS: tR=1.27 min (10-90% MeCN in 3 min), UPLC-purity (278 nm)=50.4%, ESI-MS: (calculated MH+: 252.29 g/mol, found: 252.17 m/z).

2-bis-(tert-Butoxycarbonyl)-(aminooxy)-1-(4-(5-(hydroxymethyl)-2-nitrobenzyl)piperazin-1-yl)ethan-1-one In a 100 mL round bottom flask Bis-Boc-protected Aminooxy acetic acid (0.78 g, 2.63 mmol) and N-Hydroxysuccinimide (0.31 g, 2.63 mmol) were dissolved in 25 mL Acetonitrile and stirred with a magnetic stirring bar. Dicyclohexylcarbodiimide (0.55 g, 2.63 mmol) was added and the mixture was stirred for 1.5 h at RT. After filtration to a dropping funnel it was slowly added to a solution of 4-Nitro-3-(piperazin-1-ylmethyl)benzyl alcohol (0.59 g, 2.35 mmol) in 25 mL Chloroform in a 250 mL round bottom flask. After 1 h UPLC-UV/vis indicated complete conversion of the starting material. The solvent was removed with a rotational evaporator and the residue was suspended in 100 mL Ethyl acetate and transferred to a separation funnel. The organic phase was washed three times with 50 mL water, three times with 50 mL saturated NaHCO3-solution and three times with 50 mL Brine and was dried over $MgSO_4$. The desired product was obtained after evaporation of the organic solvent as a yellow solid (1.8 g, not completely dry). UPLC-MS: tR=2.24 min (10-90% MeCN in 3 min), UPLC-purity (278 nm)=19.8%, ESI-MS: (calculated MH+: 525.14 g/mol, found: 525.25 m/z)

1-(4-(2-amino-5-(hydroxymethylpenzyl)piperazin-1-yl)-2-bis-(tert-Butoxycarbonyl)-faminooxy)ethan-1-one In a round bottom flask 2-bis-(tert-Butoxycarbonyl)-(aminooxy)-1-(4-(5-(hydroxymethyl)-2-nitrobenzyl)piperazin-1-yl)ethan-1-one was dissolved in 16 mL water/ethanol (1:4). After this iron powder (0.23 g, 4 mmol) and ammonium chloride (0.25 g, 4 mmol) were added to the solution. The reaction mixture was stirred over night at room temperature. After confirming full consumption of the start material via UPLC-MS the reaction mixture was filtered over celite to remove excess iron. The solvent was concentrated as far as possible in vacuo. After adding 50 mL of $CHCl_3$ the organic phase was washed with 3×50 mL sat. $NaHCO_3$ solution, 3×50 mL Brine, dried over $MgSO_4$ and the organic solvent removed under reduced pressure at a rotational evaporator. The final product (0.19 g, 0.4 mmol) was obtained as a brown oil. UPLC-MS: $t_R$=2.05 min (10-90% MeCN in 3 min), UPLC-purity (278 nm)=24.7%, ESI-MS: (calculated $MH^+$: 495.28, $MNa^+$: 517.26 g/mol, found: 517.29 m/z).

2-bis-(tert-Butoxycarbonyl)-(aminooxy)-1-(4-(2-azido-5-(hydroxymethylpenzyl)piperazin-1-yl)ethan-1-one In a round bottom flask 1-(4-(2-amino-5-(hydroxymethyl)benzyl)piperazin-1-yl)-2-bis-(tert-Butoxycarbonyl)-(aminooxy)ethan-1-one (0.19 g, 0.4 mmol) was dissolved in dry Acetonitrile. The solution was cooled via ice bath while under stirring tert-butyl nitrile (236 µL, 2 mmol), and then trimethylsilyl azide (351 µL, 1.6 mmol) were slowly added. The solution was further stirred with ice cooling for 2 h in a sealed flask. After UPLC-MS showed incomplete conversion tert-butyl nitrile (572 µL, 4 mmol), and then trimethylsilyl azide (702 µL, 3.2 mmol) were slowly added again. The reaction mixture was stirred further for 2 h. The solvent was then removed under reduced pressure at a rotational evaporator. After dissolving the crude product in 50 mL ethyl acetate the organic phase was washed with 3×50 mL $NaHCO_3$, 3×50 mL Brine solution and dried with Magnesium sulfate. The desired product (0.14 g, 0.20 mmol) was gained after evaporating the organic solvent. UPLC-MS: $t_R$=2.34 min (10-90% MeCN in 3 min), UPLC-purity (278 nm)=20.4%, ESI-MS: (calculated $MH^+$: 521.27, found: 521.30 m/z).

3-((4-(2-bis-(tert-Butoxycarbonyl)-(aminooxy) acetyl)piperazin-1-yl)methyl)-4-azidobenzyl (4-nitrophenyl) carbonate (X6)

2-bis-(tert-Butoxycarbonyl)-(aminooxy)-1-(4-(2-azido-5-(hydroxymethyl)benzyl)piperazin-1-yl) ethan-1-one (149 mg, 0.2 mmol) was dissolved in a round bottom flask using 0.2 mL of dry DCM. Pyridin (19.2 µL, 0.24 mmol) was added and the solution was cooled using an ice bath. To this mixture a solution of p-nitrophenylchloroformiate (32.9 mg, 0.16 mmol) in 0.2 mL of dry DCM was slowly added and the reaction mixture was stirred overnight at room temperature. The organic solvent was removed in vacuo and the desired product was obtained as a dark brown oil (0.21 g, not completely dry) UPLC-MS: $t_R$=10.72 min (0-60% MeCN in 11 min), UPLC-purity (278 nm)=8.39%, ESI-MS: (calculated $MH^+$: 686.28, $MNa^+$: 708.26 g/mol, found: 686.38 m/z).

Synthetic Steps for the Synthesis of 3-(4-(2-bis-(tert-Butoxycarbonyl)-(aminooxy)acetyl)piperazin-1-yl)-4-azidobenzyl(4-nitrophenyl) carbonate (X9)

1-(4-(2-amino-5-(hydroxymethyl)phenyl)piperazin-1-yl)-2-bis-(tert-Butoxycarbonyl)-(aminooxy)ethan-1-one 2-bis-(tert-Butoxycarbonyl)-(aminooxy)-1-(4-(5-(hydroxymethyl)-2-nitrophenyl)piperazin-1-yl)ethan-1-one (1.00 g, 1.96 mmol) was dissolved in 78 mL of Methanol in a round bottom flask. To this solution Magnesium powder (1.28 g, 19.6 mmol) was added. Under stirring then ammonium formiate (1.23 g, 19.6 mmol) was added as a solid. The solution was further stirred for 20 min at room temperature while formation of gases was observed. The solution was filtered off immediately to remove Magnesium and the solvent was removed under reduced pressure at a rotational evaporator. The crude product was freeze dried using a solvent mixture of 1:1 water/Acetonitrile. The crude product (2.20 g) was used without any further purification. UPLC-MS: $t_R$=2.21 min (10-90% MeCN in 3 min), UPLC-purity (278 nm)=53.2%, ESI-MS: (calculated $MH^+$: 481.27 g/mol, $MNa^+$: 503.25 g/mol, found: 477.30 m/z).

2-bis-(tert-Butoxycarbonyl)-(aminooxy)-1-(4-(2-azido-5-(hydroxymethyl)phenyl)piperazin-1-yl) ethan-1-one In a round bottom flask 1-(4-(2-amino-5-(hydroxymethyl) phenyl)piperazin-1-yl)-2-bis-(tert-Butoxycarbonyl)-aminooxy)ethan-1-one (1.00 g, 2.08 mmol) was dissolved in dry Acetonitrile. The solution was cooled via ice bath while under stirring tert-butyl nitrile (1.37 mL, 10.4 mmol), and then trimethylsilyl azide (1.16 mL, 8.32 mmol) were slowly added. The solution was further stirred with ice cooling for 2 h in a sealed flask. After UPLC-MS showed incomplete conversion Tert-butyl nitrile (1.37 mL, 10.4 mmol) and then trimethylsilyl azide (1.16 mL, 8.32 mmol) were slowly added again. The reaction mixture was stirred further overnight. The solvent was then removed under reduced pressure at a rotational evaporator. After dissolving the crude product in 50 mL ethyl acetate the organic phase was washed with 3×50 mL $NaHCO_3$, 3×50 mL Brine solution and dried with Magnesium sulfate. The desired product (0.2 g, 0.39 mmol) was gained after evaporating the organic solvent and purification via flash column (3:2 EtOAC/Cyclohexane). $R_f$=0.5 (EtOAc/Cyclohexane 4:1), UPLC-MS: $t_R$=2.92 min (10-

90% MeCN in 3 min), UPLC-purity (278 nm)=84.2%, ESI-MS: (calculated MH$^+$: 507.26 g/mol, MNa$^+$: 529.24 g/mol, found: 529.30 m/z).

3-(4-(2-bis-(tert-Butoxycarbonyl)-(aminooxy)acetyl) piperazin-1-yl)-4-azidobenzyl(4-nitrophenyl) carbonate (X9)

2-bis-(tert-Butoxycarbonyl)-(aminooxy)-1-(4-(2-azido-5-(hydroxymethyl)phenyl)piperazin-1-yl)ethan-1-one (76 mg, 0.15 mmol) was dissolved in a round bottom flask using 1 mL of dry DCM. Pyridin (12.2 µL, 0.15 mmol) was added and the solution was cooled using an ice bath. To this solution p-nitrophenylchloroformiate (20.3 mg, 0.15 mmol) was slowly added as a solid. After 10 min the ice bath was removed and the reaction mixture was stirred overnight at room temperature. The organic solvent was removed in vacuo and the crude product was re-dissolved in 30 mL EtOAc. The organic phase was then washed with 3× sat. NaHCO$_3$ solution, 3× Brine, dried over MgSO$_4$ and the organic solvent again removed in vacuo. The crude product was finally purified via flash column using a EtOAc/Cyclohexane (1:1) solvent mixture. The desired compound was obtained as a pale yellow oil (30 mg, 0.05 mmol). R$_f$=0.54 (EtOAC/Cyclohexane 1:1), UPLC-MS: t$_R$=3.53 min (10-90% MeCN in 3 min), UPLC-purity (278 nm)=93.6%, ESI-MS: (calculated MH$^+$: 671.66, MNa$^+$: 694.24 g/mol, found: 694.40 m/z).

$^1$H-NMR (400 MHz, CDCl$_3$, 25° C.): δ[ppm]=8.28 (d, J=9.0 Hz, 2H), 7.38 (d, J=9.0 Hz, 2H), 7.22-7.06 (m, 3H), 5.22 (s, 2H), 4.62 (s, 2H), 3.94 (t, J=3.93, 2H), 3.81 (t, J=3.81, 2H), 3.12 (t, J=3.12, 2H), 3.07 (t, J=3.07, 2H), 1.54 (s, 18H).

Chemical Synthesis of Amine Switch with Other Reductive Safety Lock (Type 2) Linker Molecules X12, X13 and X43

Synthesis of (5-(2-(2-bis-(tert-Butoxycarbonykaminooxy)acetamido)-6-(tert-butyldisulfanyl) pyridin-3-yl)methyl (4-nitrophenyl) carbonate (X12)

Synthesis of methyl 6-meracapto-5-nitropyridine-3-carboxylate

To a cooled solution of methyl 6-chloro-5-nitropyridine-3-carboxylate (1.6 gm, 7.037 mmol) in methanol (25 ml) 70% sodium hydrosulfide hydrate (1.115, 14.127 mmol) was added in small portions. The mixture stands with stirring for 30 min-1 h. Subsequently, the solid material was filtered. The remaining solution was reduced to 5 ml using rotatory evaporator. The remaining solution was acidified to pH 2 by slow addition of 1M HCl at 0° C. The resulting yellow solid material was collected by filtration and the material is used for further steps with out purification. UPLC-MS: t$_R$=1.80 min (10-90% MeCN in 3 min), UPLC-purity (278 nm)=95.0%, ESI-MS: (calculated MH$^+$: 215.01 g/mol, found: 215.20 m/z.

Synthesis of methyl 6-meracapto-5-aminopyridine-3-carboxylate

Methyl 6-meracapto-5-nitropyridine-3-carboxylate (1.00 gm, 4.537 mmol) and 1.85 gm (32.48 mmol) of iron powder were placed in the reaction flask containing 50 mL of 75% Methanol and 25% water. Calcium chloride (0.41 gm, 3.63 mmol) was then added and the mixture was refluxed on oil bath till the starting material completely converts to the product. At the end of the reflux period, the mixture was filtered celite to remove excess iron. The filtrate was concentrated to near dryness and subsequently water (25 ml) was added, and compound was extracted using ethyl acetate (3×25 ml). The solvent was removed under reduced pressure and the obtained crude residue was pure enough to proceed further (3.49 mmol, 77%). UPLC-MS: t$_R$=1.26 min (10-90% MeCN in 3 min), UPLC-purity (278 nm)=93%, ESI-MS: (calculated MH$^+$: 185.04 g/mol, found: 185.14 m/z).

Synthesis of (5-amino-6-meracaptopyridin-3-yl)methanol

Methyl 6-meracapto-5-aminopyridine-3-carboxylate (0.7 gm, 3.68 mmol) was dissolved in dry THF (20 mL) and the solution was cooled to 0° C. Lithium aluminum hydride (1.42 gm, 36.89 mmol) was added portion wise to the reaction mixture under N$_2$ atmosphere during 10 min. The resulting solution was stirred for 24 h at room temperature. After completion of the reaction as indicated by UPLC, the excess of LiAlH$_4$ was quenched by adding simultaneously 1.4 ml of water, 1.4 ml 10% NaOH, 4.2 ml of water at 0° C. Al salts were filtered off and the solid materials washed with water and MeOH (1:1, 100 ml). The solvent was evaporated, and the compound was extracted from solid cake using isopropanol (3×50 ml). Isopropanol was removed under reduced pressure to obtain desired product (1.92 mmol, 52%) in pure form. UPLC-MS: t$_R$=1.01 min (10-90% MeCN in 3 min), UPLC-purity (278 nm)=96%, ESI-MS: (calculated MH$^+$: 157.04 g/mol, found: 157.11 m/z)

Synthesis of (2-(2-bis-(tert-Butoxycarbonyl)(aminooxy))-N-(2-(tert-butyldisulfanyl)-5-(hydroxymethyl)pyridin-3-yl) acetamide)

To a Schlenk flask charged with 6-mercapto-5-amino pyridine-3-carboxylic acid (1.3 gm, 8.03 mmol) was added CH$_2$Cl$_2$ (20 mL), 2-Methyl-2-propanethiol (0.91 ml, 8.03 mmol) and TBHP (1.13 gm, 8.83 mmol, 70% solution in water) under N$_2$ atmosphere. After 30 seconds, NIS (0.19 gm, 0.18 mmol) was added in one batch. Then the Schlenk flask was allowed to react for 1 h at 25° C. After the completion of the reaction, it was quenched by water (20.0 mL) and extracted with ethyl acetate (3×30 mL). The organic layers were combined and evaporated under vacuum and the compound was used in next steps without further purification. UPLC-MS: t$_R$=1.68 min (10-90% MeCN in 3 min), UPLC-purity (278 nm)=93%, ESI-MS: (calculated MH$^+$: 245.08 g/mol, found: 245.18 m/z).

Synthesis of (5-(2-(2-bis-(tert-Butoxycarbonyl)(aminooxy)acetamido))-6-(tert-butyldisulfanyl) pyridin-3-yl)methyl (4-nitrophenyl) carbonate (X12)

(5-amino-6-(tert-butyldisulfanyl)pyridin-3-yl)methanol (83.5 mg, 0.156 mmol mmol) was provided in CH$_2$Cl$_2$ (2 mL) and dry, pyridine (0.161 mL, 0.19 mmol) was added. Thereafter, 4-nitrophenylchloroformiate (31.9 mg, 0.154 mmol) was added. Indicated by LCMS and TLC reaction had complete after 12 h. Dichloromethane was removed in vacuo yielding a pale yellow/orange crude oil and the residue was re-dissolved in 10 mL ethyl acetate and washed water and brine 1:1 (each 5 mL). Finally EtOAc was removed under reduced pressure to obtain desired product (0.08 mmol, 75%). UPLC-MS: tR=12.59 min (10-60%

MeCN in 11.50 min, 60-90% 11.51-13 min), UPLC-purity (=nm)=70%, ESI-MS: (calculated MNa+: 705.19 g/mol, found: 705.41 m/z).

Synthetic Steps for the Synthesis of 3-(4-(2-bis-(tert-Butoxycarbonyl)-((aminooxy)acetyl)piperazin-1-yl)-4-nitrobenzyl (4-nitrophenyl) carbonate (X13)

methyl 3-fluoro-4-nitrobenzoate

3-Fluoro-4-nitrobenzoic acid (5.00 g, 27.01 mmol) was dissolved in 100 mL Methanol in a 250 mL round bottom flask with a stirring bar and 3 mL (54.02 mmol) $H_2SO_4$ was added. After 42 h stirring at 50° C. UPLC-UV/vis indicated complete conversion to the methyl ester. With a rotational evaporator the reaction mixture was concentrated to 10 mL. After addition of 100 mL Ethyl acetate and 100 mL $H_2O$ the mixture was stirred and subsequently $K_2CO_3$ (7.00 g) was added portion wise. The mixture was transferred to a separation funnel, the layers were separated and the aqueous phase was extracted three times with 100 mL Ethyl acetate. The combined organic layers were dried over $MgSO_4$ and after evaporation 4.81 g (24.15 mmol, 89%) of the desired product was gained as an orange solid. UPLC-MS: $t_R$=2.53 min (10-90% MeCN in 3 min), UPLC-purity (210 nm)=99.4%, ESI-MS: (calculated $MH^+$: 200.14 g/mol, found: —).

methyl 4-nitro-3-(piperazin-1-yl)benzoate

Piperazine (4.07 g, 47.20 mmol) and $K_2CO_3$ (4.24 g, 30.68 mmol) were suspended in 50 mL Chloroform in a 250 mL round bottom flask with a stirring bar. methyl 3-fluoro-4-nitrobenzoate (4.7 g, 23.60 mmol), dissolved in 50 mL Chloroform, was added slowly via dropping funnel at RT over 1 h and the mixture was stirred rapidly. After 66 h UPLC-UV/vis indicated that only 10% of the starting material was conversed. Piperazin (4.07 g, 47.20 mmol) was added and after 2 h UPLC-UV/vis indicated a complete conversion. After 15 minutes 100 mL Chloroform and 150 mL saturated $NaHCO_3$-solution were added, and the mixture was transferred to a separation funnel. The layers were separated, and the organic phase was washed twice with 100 mL saturated $NaHCO_3$-solution and once with 100 mL Brine. After drying over $MgSO_4$ the desired product was obtained after evaporating the organic solvent on rotational evaporator as a red solid (7.87 g, not completely dry). UPLC-MS: $t_R$=1.72 min (10-90% MeCN in 3 min), UPLC-purity (210 nm)=87.2%, ESI-MS: (calculated $MH^+$: 266.27 g/mol, found: 266.23 m/z).

(4-nitro-3-(piperazin-1-yl)phenyl)methanol

Methyl 4-nitro-3-(piperazin-1-yl)benzoate (5.85 g, not completely dry, assumed 20.00 mmol) was dissolved in 40 mL THF in a 500 mL round bottom flask and stirred with a magnetic stirring bar. LiCl (5.09 g, 120.00 mmol), $NaBH_4$ (4.54 g, 120.00 mmol) and 80 mL Ethanol were added successively. After 15 h UPLC-UV/vis indicated a complete conversion. The reaction mixture was concentrated in vacuo, 20 mL Chloroform was added, and the mixture was stirred rapidly while 30 mL of a 2 M $NH_4Cl$ solution was added dropwise. After 1 h 120 mL 1 M NaOH and 80 mL Chloroform were added slowly, and the mixture was transferred to a separation funnel. The layers were separated, and the aqueous phase was extracted three times with 100 mL Chloroform. The combined organic layers were dried over $MgSO_4$ and after evaporation of the organic solvent the desired product was obtained as an orange solid (3.97 g, 16.73 mmol, 84%). UPLC-MS: $t_R$=1.27 min (10-90% MeCN in 3 min), UPLC-purity (210 nm)=70.0%, ESI-MS: (calculated $MH^+$: 238.26 g/mol, found: 238.24 m/z).

2-bis-(tert-Butoxycarbonyl)-(aminooxy)-1-(4-(5-(hydroxymethyl)-2-nitrophenyl)piperazin-1-yl)ethan-1-one Bis-(tert-Butoxycarbonyl)-(aminooxy)acetic acid ((Boc)$_2$AOAcOH, 2.96 g, 9.96 mmol, 1.2 eq.) and N-hydroxysuccinimide (NHS, 1.15 g, 9.96 mmol, 1.2 eq.) was dissolved in 10 mL Acetonitril. To this solution was added dicyclohexylcarbodiimide (DCC, 2.07 g, 9.96 mmol, 1.2 eq.) as a solid, after dissolution of DCC a white precipitate formed. The reaction mixture was stirred for 1 h at room temperature where the (Boc)$_2$AOAc-NHS ester was quantitatively formed according to UPLC-MS. Thereafter the mixture was filtered into a round bottom flask where (4-nitro-3-(piperazin-1-yl)phenyl)methanol (1.98 g, 8.30 mmol) was provided in 83 mL of Chloroform. The mixture was stirred at room temperature for 1 h after which the completion of the reaction was confirmed by TLC and UPLC-MS. Additional formed precipitate was filtered off and the organic phase was washed 3× water, 3× sat. $NaHCO_3$ and 3× brine solution. The organic phase was dried with $MgSO_4$ and hence, the organic solvent was removed in vacuo and the title compound was obtained as a yellow oil (4.35 g, 8.52 mmol, quantitative, not completely dry). UPLC-MS: $t_R$=3.00 min (10-90% MeCN in 3 min), UPLC-purity (278 nm)=48.2%, ESI-MS: (calculated $MH^+$: 511.24, $MNa^+$: 534.23 g/mol, found: —).

3-(4-(2-bis-(tert-Butoxycarbonyl)-((aminooxy)acetyl)piperazin-1-yl)-4-nitrobenzyl(4nitrophenyl) carbonate (X13)

2-bis-(tert-Butoxycarbonyl-aminooxy)-1-(4-(5-(hydroxymethyl)-2-nitrophenyl)piperazin-1-yl)ethan-1-one (2.06 g, 4 mmol) was provided in a 8 mL round bottom flask with a stirring bar. To the solution dry pyridine was added. Thereafter, 4-nitrophenylchloroformiate (0.86 g, 4.2 mmol) was added slowly as a solid at room temperature. The reaction is exothermic and may cause DCM to bubble. After 2 h stirring at room-temperature UPLC-MS and TLC indicated complete conversion to the carbonate. The solvent was removed under reduced pressure at a rotational evaporator. The product was purified via column chromatography (cyclohexane/ethylacetate 1:1) and gave a yellow solid (410 mg, 0.61 mmol). UPLC-MS: $t_R$=3.44 min (10-90% MeCN in 3 min), UPLC-purity (278 nm)=92.4%, ESI-MS: (calculated $MH^+$: 676.25 g/mol, $MNa^+$: 698.23 g/mol, found: 698.51 m/z).

$^1$H-NMR (400 MHz, CDCl$_3$, 25° C.): δ[ppm]=8.29 (d, J=9.2 Hz, 2H), 7.84 (d, J=8.3 Hz, 1H), 7.39 (d, J=9.2 Hz, 2H), 7.19 (s, 1H), 7.16 (d, J=9.7 Hz, 1H), 5.29 (s, 2H), 4.61 (s, 2H), 3.89 (t, J=3.90, 2H), 3.78 (t, J=3.78, 2H), 3.15 (t, J=3.15, 2H), 3.10 (t, J=3.10, 2H), 1.54 (s, 18H).

Synthetic Steps for the Synthesis of 3-((4-(2-(aminooxy)acetyl)piperazin-1-yl)methyl)-4-nitrobenzyl (4-nitrophenyl) carbonate (X43)

2-bis-(tert-Butoxycarbonyl)-(aminooxy)-1-(4-(5-(hydroxymethyl)-2-nitrophenyl)piperazin-1-yl)ethan-1-one (1.27 g, not completely dry, assumed 1.86 mmol) was dissolved in 5 mL Chloroform in a 50 mL round bottom flask with a magnetic stirring bar and cooled to 0° C. with an ice bath. Dry pyridine (0.23 mL, 0.23 g, 2.88 mmol) and p-Nitrophenylchloroformate (0.59 g, 2.88 mmol) were added successively. After x h UPLC-UV/vis indicated complete conversion of the starting material. With a rotational evaporator the solvent was removed, and the residue was dissolved in 5 mL Ethyl acetate/Cyclohexane (1:1). After purification via flash column chromatography with Ethyl acetate/Cyclohxane (1:1) the desired product was obtained (0.02 g, 0.03 mmol). UPLC-MS: $t_R$=2.96 min (10-90% MeCN in 3 min), UPLC-purity (278 nm)=55.6%, ESI-MS: (calculated MNa$^+$: 712.24 g/mol, found: 712.41 m/z).

Chemical Synthesis of Amine Switch with Nucleophilic Release (Type 3) Linker Molecules X22 and X42

Synthesis of 2-(2-azido-5-(4-(2-((2-bis-(tert-Butoxycarbonyl)amino)oxy)acetyl)piperazin-1-yl)phenyl) acetic acid (X22)

Synthesis of methyl 2-(5-fluoro-2-nitrophenyl)acetate

5-Fluoro-2-nitrophenylacetic acid (3.00 gm, 14.92 mmol) was taken in 100 ml round bottom flask with a stirring bar. The compound was dissolved in 40 ml of MeOH and 1.62 ml (29.84 mmol) of $H_2SO_4$ was added slowly at the room temperature. The resulting reaction mixture was refluxed for 6 h. The progress of the reaction was monitored by UPLC-MS and TLC. After completion of the reaction, Methanol was removed under reduced pressure at a rotational evaporator. To the resulting crude, 20 ml water was added, and the solution was neutralized by using saturated $K_2CO_3$ solution (50 ml). The precipitated solid was filtered and washed with water and dried under reduced pressure to obtain (129.86 mmol, 98%) desired product as a white color solid. UPLC-MS: $t_R$=2.41 min (10-90% MeCN in 3 min), UPLC-purity (278 nm)=97%, ESI-MS: (calculated MH$^+$: 214.05 g/mol, found: . . . ).

Synthesis of tert-butyl 4-(3-(2-methoxy-2-oxoethyl)-4-nitrophenyl)piperazine-1-carboxylate Methyl 2-(5-fluoro-2-nitrophenyl)acetate (0.70 gm, 3.25 mmol) was dissolved in Dry DMF. To this solution, 1-Boc-piperazine (0.83 gm, 4.39 mmol) and $Na_2CO_3$ (0.71 gm, 6.5 mmol) was added at room temperature and the resulting reaction mixture was heated up to 80° C. for overnight. The reaction progress was monitored by UPLC-MS and TLC. After completion of reaction, the solution was filtered to remove the solid byproducts and the DMF was removed under reduced pressure using a rotational evaporator. Ice cold water (25 ml) was added to the crude material and resulting solid was filtered and washed with water (50 ml) and dried under reduced pressure to obtain expected product (1.01 gm, 2.66 mmol, 82%) in yellow color solid UPLC-MS: $t_R$=3.01 min (10-90% MeCN in 3 min), UPLC-purity (278 nm)=96.0%, ESI-MS: (calculated MH$^+$: 380.18 g/mol, found: 324.10(M2H$^+$-tbu).

Synthesis of tert-butyl 4-(4-amino-3-(2-methoxy-2-oxoethyl)phenyl)piperazine-1-carboxylate To a solution of the tert-butyl 4-(3-(2-methoxy-2-oxoethyl)-4-nitrophenyl)piperazine-1-carboxylate (1.00 gm, 2.58 mmol) in dioxane/$H_2O$ (25 mL, 3:1) was added $NH_4Cl$ (1.23 gm, 1.01 gm, 18.50 mmol) and Zn dust (1.23 gm, 18.50 mmol) at rt. The reaction mixture was stirred for 3 h at the same temperature, after that it was filtered through a celite bed. The resulting solution was evaporated, and crude material was partitioned between $H_2O$ (100 mL) and EtOAc (300 mL). The organic layer was separated, dried ($MgSO_4$) concentrated to get desired product in Yellow color solid (1.75 mmol, 68%). UPLC-MS: $t_R$=2.12 min (10-90% MeCN in 3 min), UPLC-purity (278 nm)=94.0%, ESI-MS: (calculated MH$^+$: 350.21 g/mol, found: 350.19 m/z).

Synthesis of tert-butyl 4-(4-azido-3-(2-methoxy-2-oxoethyl)phenyl)piperazine-1-carboxylate The tert-butyl 4-(4-amino-3-(2-methoxy-2-oxoethyl)phenyl)piperazine-1-carboxylate (0.35 gm 0.99 mmol) dissolved in dry acetonitrile (25 mL) and cooled to 0° C. 90% tert-Butyl nitrite (0.837 gm, 7.94 mmol) was added dropwise to the reaction mixture and then $TMSN_3$ (0.722 g, 5.95 mmol) was added over 10 minutes. The resulting red colored mixture was stirred for 3 h. The progress of the reaction was monitored by UPLC-MS. After completion of reaction, excess of $TMSN_3$, t-BuONO and the solvent were removed under reduced pressure the obtained red residue was dissolved in 50 mL ethyl acetate and washed with (2×50 mL) water. The ethylacetae layer was dried over $MgSO_4$ and removed under reduced pressure to get orange solid which was taken forward without further purification (0.33 gm, 0.88 mmol). UPLC-MS: $t_R$=3.01 min (10-90% MeCN in 3 min), UPLC-purity (278 nm)=95.0%, ESI-MS: (calculated MH$^+$: 376.20 g/mol, found: 376.28 m/z).

Synthesis of 2-(2-azido-5-(4-(tert-butoxycarbonyl) piperazin-1-yl)phenyl)acetic acid A solution of the tert-butyl 4-(4-azido-3-(2-methoxy-2-oxoethyl)phenyl)piperazine-1-carboxylate (0.314 gm, 0.83 mmol), LiOH (0.102 gm, 4.14 mmol), MeOH (5 mL), and $H_2O$ (0.2 mL) was stirred at rt for 3 h. After complete conversion of the starting materials to the product (monitored by UPLC-MS), the reaction mixture was evaporated and to the resulting crude material, saturated $NH_4Cl$ added till the solution PH reaches to 6. The resulting solution was extracted with EtOAc (2×25 mL), dried over $MgSO_4$ and concentrated to provide the product as a Yellow solid (0.65 mmol, 78%). UPLC-MS: $t_R$=2.55 min (10-90% MeCN in 3 min), UPLC-purity (278 nm)=95.0%, ESI-MS: (calculated MH$^+$: 362.18 g/mol, found: 306.04 m/z).

Synthesis of 4-(4-azido-3-(carboxymethyl)phenyl) piperazin-1-ium 2,2,2-trifluoroacetate Pure trifluoracetic acid (0.6 ml, 6.14 mmol) was added dropwise to the round bottom flask containing 2-(2-azido-5-(4-(tert-butoxycarbonyl)piperazin-1-yl)phenyl)acetic acid (0.22 gm, 0.61 mmol) and the resulting solution was stirred at rt for 1 hour. After completion of reaction (monitored by UPLC-MS), cold ether (25 mL) was added and the resulting solid was filtered and washed with cold ether. The resulting light brown color solid (0.30 gm, 85%) was dried and proceeded to further steps without purification. UPLC-MS: $t_R$=2.80 min (10-90% MeCN in 3 min), UPLC-purity (278 nm)=87.0%, ESI-MS: (calculated MH$^+$: 262.13 g/mol, found: 262.11 m/z) wrong mass.

Synthesis of 2-(2-azido-5-(4-(2-((((2-bis-(tert-Butoxycarbonyl)amino)oxy)acetyl)piperazin-1-yl)phenyl) acetic acid (X22)

Bis-(tert-Butoxycarbonyl)-(aminooxy)acetic acid ((Boc)$_2$AOAcOH, 88.4 mg, 0.30 mmol) and N-hydroxysuccinimide (NHS, 34.6 g, 0.30 mmol) was dissolved in 2 mL dry Acetonitrile. To this solution was added dicyclohexylcarbodiimide (DCC, 62.0 mg, 0.30 mmol) as a solid, after dissolution of DCC a white precipitate formed. The reaction mixture was stirred for 1 h at room temperature where the (Boc)$_2$AOAc-NHS ester was quantitatively formed according to UPLC-MS. Thereafter the mixture was filtered with a filter paper to remove the DCC-urea directly into a reaction flask that contains 4-(4-azido-3-(carboxymethyl)phenyl)piperazin-1-ium 2,2,2-trifluoroacetate (100 mg, 0.20 mmol) in dry DMF (2 ml) and DIEPA (155 μL, 0.89 mmol). The mixture was further stirred at room temperature for 1-2 h. After completion of the reaction, Solvent was evaporated under reduced pressure and reaction mixture was neutralized by adding NH$_4$Cl (25 ml). The compound was extracted with EtOAc (2×25 mL), dried over MgSO$_4$ and concentrated to provide the product as a dark brown color solid (0.19 mmol, 97%). UPLC-MS: $t_R$=2.80 min (10-90% MeCN in 3 min), UPLC-purity (278 nm)=87.0%, ESI-MS: (calculated MNa$^+$: 557.23 g/mol, found: 557.28 m/z).

$^1$H NMR (400 MHz,) δ7.06 (d, J=8.7 Hz, 1H), 6.90 (d, J=8.8 Hz, 1H), 6.83 (s, 1H), 4.60 (s, 2H), 3.90-3.84 (m, 2H), 3.77-3.72 (m, 2H), 3.59 (s, 2H), 3.24-3.11 (m, 4H), 1.54 (s, 18H).

Synthesis of 2-(5-(4-(2-((2-bis-)tert-Butoxycarbonyl)amino)oxy)acetyl)piperazin-1-yl)-2-nitrophenyl) acetic acid (X42)

Synthesis of 2-(5-(4-(tert-butoxycarbonyl)piperazin-1-yl)-2-nitrophenyl)acetic acid To the solution tert-butyl 4-(3-(2-methoxy-2-oxoethyl)-4-nitrophenyl)piperazine-1-carboxylate (0.50 gm, 1.30 mmol) in MeOH:H$_2$O (21.2 mL, 16:1), LiOH was added and stirred at rt for overnight. After complete conversion of the starting materials to the product (monitored by UPLC-MS), the reaction mixture was evaporated and to the resulting crude material saturated NH$_4$Cl (25 mL) added till the solution PH reaches to 6. The compound was extracted with EtOAc (4×25 mL), dried over MgSO$_4$ and concentrated under reduced pressure to provide the desired product as a Yellow solid (0.78 mmol, 59%). UPLC-MS: $t_R$=2.36 min (10-90% MeCN in 3 min), UPLC-purity (278 nm)=97.0%, ESI-MS: (calculated MH$^+$: 380.18 g/mol, found: 310.04 m/z (2W-tbu m/z)).

Synthesis of 4-(3-(carboxymethyl)-4-nitrophenyl) piperazin-1-ium 2,2,2-trifluoroacetate Pure trifluoracetic acid (0.73 ml, 7.59 mmol) was added dropwise at the room temperature to the round bottom flask containing 2-(5-(4-(tert-butoxycarbonyl)piperazin-1-yl)-2-nitrophenyl)acetic acid (0.28 gm, 0.76 mmol) and the resulting solution was stirred for 1 hour. After completion of reaction (monitored by UPLC-MS), cold ether (25 mL) was added and the resulting solid was filtered and washed with cold ether. The resulting Yellow color solid (88%) was dried and proceeded to further steps without purification. UPLC-MS: $t_R$=1.35 min (10-90% MeCN in 3 min), UPLC-purity (278 nm)=88.9%, ESI-MS: (calculated MH$^+$: 266.11 g/mol, found: 266.11 m/z).

Synthesis of 2-(5-(4-(2-((2-bis-)tert-Butoxycarbonyl)amino)oxy)acetyl)piperazin-1-yl)-2-nitrophenyl) acetic acid (X42)

Bis-(tert-Butoxycarbonyl)-(aminooxy)acetic acid ((Boc)$_2$AOAcOH, 88.4 mg, 0.30 mmol) and N-hydroxysuccinimide (NHS, 34.6 g, 0.30 mmol) was dissolved in 2 mL dry Acetonitrile. To this solution was added dicyclohexylcarbodiimide (DCC, 62.0 mg, 0.30 mmol) as a solid, after dissolution of DCC a white precipitate formed. The reaction mixture was stirred for 1 h at room temperature where the (Boc)$_2$AOAc-NHS ester was quantitatively formed according to UPLC-MS. Thereafter the mixture was filtered with a filter paper to remove the DCC-urea directly into a reaction flask that contained 4-(3-(carboxymethyl)-4-nitrophenyl) piperazin-1-ium 2,2,2-trifluoroacetate (100 mg, 0.20 mmol) in dry DMF (2 ml) in and DIEPA (155 μL, 0.89 mmol). The mixture was stirred at room temperature for 1-2 h after which the completion of the reaction was confirmed by UPLC-MS. After completion of the reaction, Solvent was evaporated under reduced pressure and reaction mixture was neutralized by adding NH$_4$Cl (25 ml). The resulting solution was extracted with EtOAc (2×25 mL) and concentrated to provide the product as a dark brown color solid (0.19 mmol, 97%). UPLC-MS: $t_R$=2.74 min (10-90% MeCN in 3 min), UPLC-purity (278 nm)=87.0%, ESI-MS: (calculated MNa$^+$: 561.22 g/mol, found: 561.28 m/z).

---

We claim:

1. A compound of formula 1, X-T$_b$-V$_a$—U—Y—Z (1), wherein

X is a moiety of formula 2

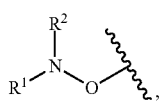

(2)

wherein each R$^1$ and R$^2$ is independently from each other H or B, wherein at least R$^1$ or R$^2$ is B, B is an acid labile amine protecting group, T is a linear or branched spacer comprising 1 to 5 of the moieties selected from: —C$_{1-12}$-alkyl-, (—C$_2$H$_4$O—)$_{1-12}$, —C(=O)—, —C(=O)—JR$^9$—, -JR$^9$—C(=O)—, -JR$^9$—, phenyl, 5- or 6-membered heteroaryl, J is CH or N, and wherein R$^9$ is selected from the group consisting of H, C$_{1-4}$-alkyl, —C$_{1-6}$-alkyl-NH$_2$, —C$_{1-6}$-alkyl-NHB, —C$_{1-6}$-alkyl-NB$_2$, —R$^{15}$, —C$_{1-6}$-alkyl-R$^{15}$, and —C$_{1-6}$-alkyl-NH—R$^{15}$, wherein B is an independently selected acid labile amine protecting group, R$^{15}$ is a blocking agent that is able to react with an aldehyde moiety selected from the group consisting of cysteinyl, threoninyl, 2-mercaptoethanol, cysteamine, ethandithiole, hydroxylamine, O-methylhydroxylamine, N-methylhydroxylamine, dithiothreitol, and hydrazine, wherein:

amine and/or thiol moieties of the blocking agent may be protected by an acid labile amine protecting group B, and/or an acid labile thiol protecting group, b is 0 or 1, V is an electron-withdrawing moiety selected from the group consisting of —NR$^{11}$—C(=O)—, —C(=O)—NR$^{11}$—, —S(=O)—, —NR$^{12}$—(CH$_2$)$_p$—, -piperazinyl-(CH$_2$)$_p$—, -pyridinyl-, and pyrimidinyl, wherein R$^{11}$ is selected from the group consisting of H and C$_{1-4}$-alkyl, R$^{12}$ is selected from the group consisting of H and C$_{1-4}$-alkyl, p is 0, 1 or 2, a is 1, wherein the sum of a and b is 1 or 2, U is a phenyl or a five- or six-membered heteroaryl moiety, that is bound to at least one of the moieties V, W$_q$ and E$_n$ and that is unsubstituted or substituted by C$_{1-6}$-alkyl, wherein V is defined as described above, W is selected from the group consisting of —N$_3$, —NO$_2$, —S(=O)—R$^8$, —S—S—R$^8$, —O—CH$_2$—N$_3$, —O—C(=O)—O—CH$_2$—N$_3$, —N=N-phenyl, —N=N—R$^8$,

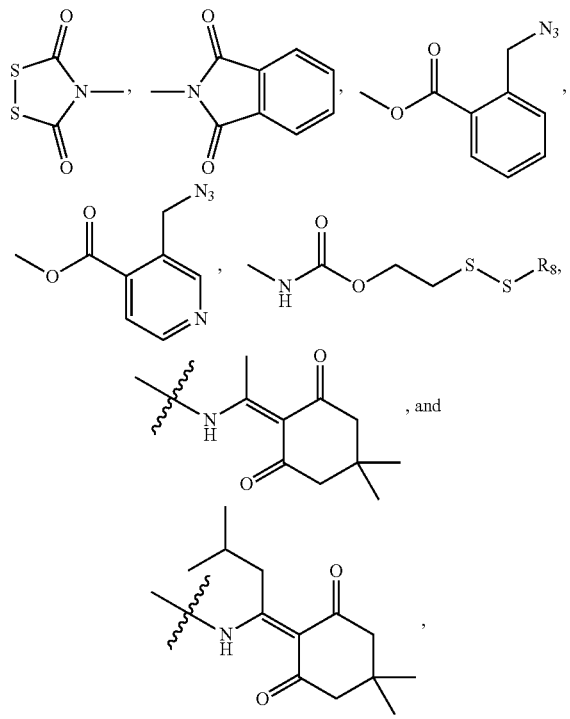

wherein
R⁸ is pyridyl, pyrimidinyl, pyrazinyl, pyridazyl, —C₁-C₆-alkyl or —(CH₂)$_p$—NMe₂, p is 1, 2, 3 or 4,
E is an electron withdrawing group under acidic conditions,
n is an integer between 0 and 4, and q is an integer between 1 and 4, wherein the sum of n and q is equal or lower than 4, and wherein
when U is a phenyl moiety and Y is —(CH₂)$_m$—O—C(=O)—, the sum of Hammett constants of V, W, E under acidic conditions is larger than 0.45, and wherein
W is in ortho or para position in relation to Y,
Y is —(CH₂)$_m$—C(=O)— or —(CH₂)$_m$—O—C(=O)—, m is 1, 2 or 3, and
Z is an electron-withdrawing leaving group.

2. The compound of claim 1, wherein E is selected from the group consisting of piperidinyl, piperazinyl, pyridyl, pyrimidinyl, pyrazinyl, pyridazyl, —N(C₂H₄)₂NH₂, —N(C₂H₄)₂N—B, —N=N-phenyl, —N=N—R⁸, —(CH₂)$_r$—NH—C₁₋₆-alkyl, —(CH₂)$_r$—N(C₁₋₆-alkyl)₂—, —F, —Cl, —Br, —I, —CN, —NO₂, —N₃, —CF₃, —SO₃H, —CO₂H, —C(=O) NH₂, —SO₂Me, —SOMe, —SO₂Et, —SOEt,
R⁸ is pyridyl, pyrimidinyl, pyrazinyl, pyridazyl, —C₁-C₆-alkyl or —(CH₂)$_p$—NMe₂, and
B is an acid labile amine protecting group, and
r is 0, 1, 2, 3 or 4.

3. The compound according to claim 1, wherein,
B is selected from the group consisting of: Boc (—C(=O) OtBu), Eei (=CMeOEt, 1-ethoxyethylidene) trityl (—C(Ph)₃), —C(=O)CPh₃, Mmt (—C(Ph)₂C₆H₄OMe), DMT (—C(Ph)(C₆H₄OMe)₂), Cbz(—C(=O)OCH₂Ph), benzylideneamine (=CPh), phtalimides (=(CO)₂C₆H₄), p-toluenesulfonamides (—SO₂C₆H₄Me), benzylamine (—CH₂Ph), acetamides (—COMe), trifluoroacetamide (—COCF₃), Dde (1-(4,4-dimethyl-2,6-dioxocyclohex-1-ylidene)-3-ethyl) and 1-(4,4-dimethyl-2,6-dioxocyclohex-1-ylidene)-3-methylbutyl (ivDde), and the acetal- or ketal protecting groups are selected from:

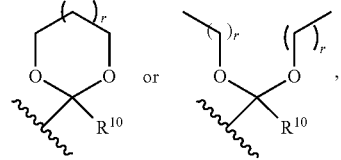

wherein r is 0 to 12, and
R¹⁰ is —C₁-C₁₂-alkyl-.

4. The compound according to claim 1, wherein b is 1, and T is selected from the group consisting of:
—C₁-C₁₂-alkyl-, —R⁵—C(=O)—, —R⁵—C(=O)—NR⁹—, —R⁵—NR⁹—C(=O)—R⁶—, —R⁵—C(=O)—NR⁹—R⁶—, —R⁵—C(=O)—NR⁹—R⁵'—NR⁹'(=O)—R⁶—, and R⁵—C(=O)—NR⁹— wherein
R⁵, R⁵' and R⁶ are independently from each other selected from the group consisting of C₁-C₁₂-alkyl and (—C₂H₄O—)₁₋₁₂, and wherein,
R⁹ and R⁹' are independently from each other selected from the group consisting of H, C₁₋₄-alkyl, —C₁₋₆-alkyl-NH₂, —C₁₋₆-alkyl-NHB, —C₁₋₆-alkyl-NB₂, —R¹⁵, —C₁₋₆-alkyl-R¹⁵, and —C₁₋₆-alkyl-NH—R¹⁵.

5. The compound according to claim 1, wherein U is a five- or six-membered heteroaryl moiety comprising 1 or 2 heteroatoms.

6. The compound according to claim 1, wherein U is selected from a group consisting of a moiety of formula 5, 6, 7 and 8,

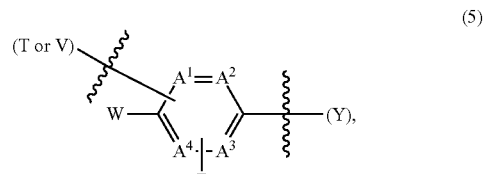

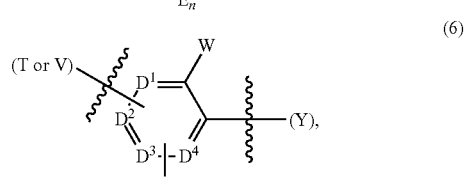

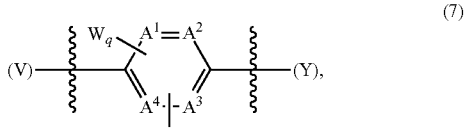

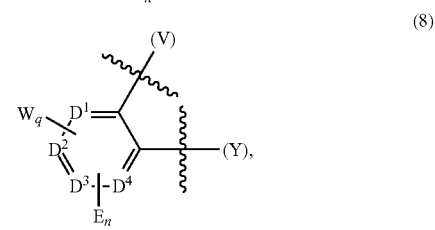

wherein
when U is a moiety of formula 5 and 6, U is bound to T or V,
when U is a moiety of formula 7 and 8, U is bound to V, $A^1, A^2, A^3, A^4$ and $D^1, D^2, D^3, D^4$ are independently from each other selected from the group consisting of C, N, S and O, wherein 2 to 4 of $A^1, A^2, A^3$ and $A^4$ or of $D^1, D^2, D^3$ and $D^4$ are C, n is an integer between 0 and 3, when U is a moiety of formula 5 or 6, an integer between 0 and 4, when U is a moiety of formula 7 or 8, q is an integer between 0 and 4, and wherein the sum of n and q is equal to or lower than 4.

7. The compound according to claim 6, wherein U is selected from a group consisting of a moiety of formula 9, 10, 11 and 12, (9)

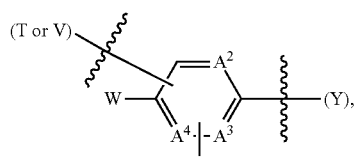

(10)

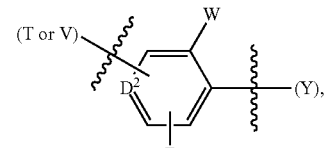

(11)

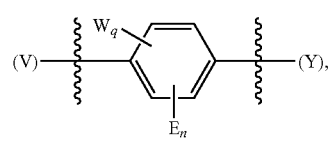

(12)

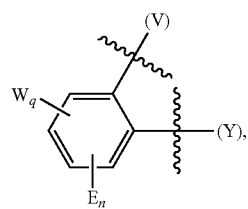

wherein

U is bound to T or V when U is a moiety of formula 9 or 10,

U is bound to V when U is a moiety of formula 11 or 12, $A^2, A^3$ and $A^4$ are C, or two of $A^2, A^3$ and $A^4$ are C and the other two of $A^2, A^3$ and $A^4$ are N, and $D^2$ is C or N.

8. The compound according to any claim 1, wherein U is selected from a group consisting of a moiety of formula 13, 14, 15, 16, 17, 18, 19, 20 and 21, (13)

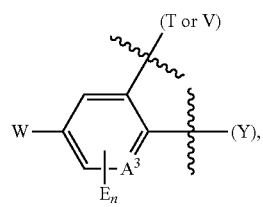

(14)

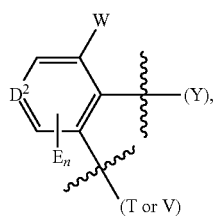

(15)

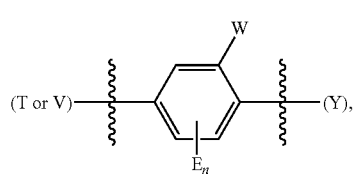

(16)

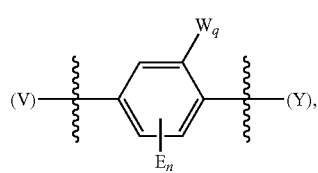

(17)

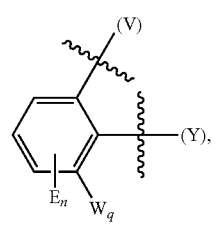

(18)

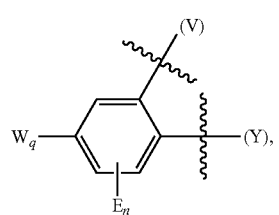

(19)

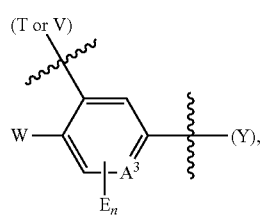

(20)

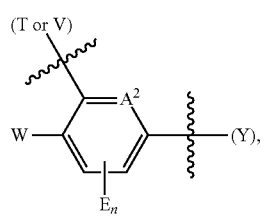

-continued (21)

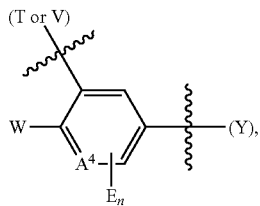

wherein
U is bound to T or V when U is a moiety of formula 13, 14 or 15,
U is bound to V when U is a moiety of formula 16, 17 or 18,
$A^2$, $A^3$ and $A^4$ is C or N, and
$D^2$ is C or N.

9. The compound according to claim 1 wherein Z is selected from the group consisting of: —F, —Cl, —Br, —I, —$N_3$, —OH, —O(C=O)$CH_2$(C=O)OH, —$SR^{14}$, —$OCF_3$, —$OCH_2CF_3$, —$OSO_2CF_3$, —$SO_2C_6H_4CH_3$, —$SO_2CF_3$, —$SO_2CH_3$,

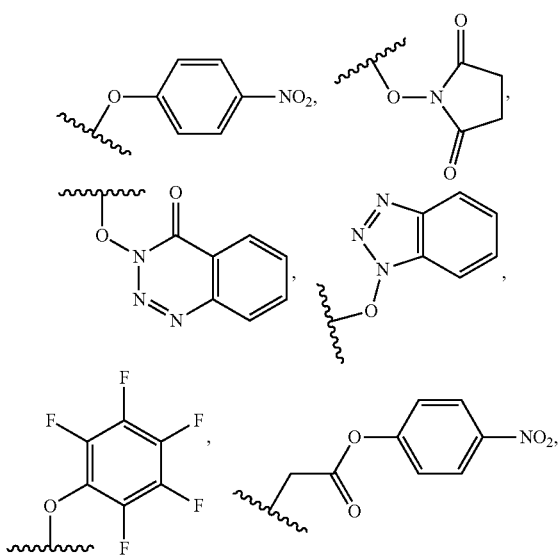

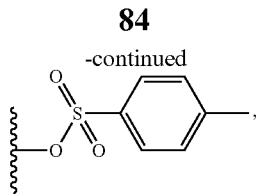

wherein $R^{14}$ is an $C_1$-$C_6$-alkyl-, an arylic- or benzylic substituent.

10. The compound according to claim 1 wherein V is an electron-withdrawing moiety selected from the group consisting of: —$NR^{11}$—C(=O)—, —C(=O)—$NR^{11}$—, —$NR^{12}$—$(CH_2)_p$—, and -piperazinyl-$(CH_2)_p$.

11. The compound according to claim 1 wherein b is 1, and T is —$C_1$-$C_{12}$-alkyl-, $C_{1-3}$-alkyl, —$R^5$—C(=O)—, —$R^5$—C(=O)—$NR^9$—$R^6$—, —$R^5$—C(=O)—$NR^9$—, —C(=O)—$NR^9$—$R^6$—, —$R^5$—$NR^9$—C(=O)—$R^6$—, —$R^5$—$NR^9$—$R^{5'}$—$NR^{9'}$—C(=O)—$R^6$—, —$R^5$—C(=O)—$NR^9$—$R^{5'}$—$NR^{9'}$—C(=O)—$R^6$—, —$R^5$—$NR^9$, —$R^5$—$NR^9$—$R^6$, —$R^5$—$NR^9$—$R^{5'}$—$NR^{9'}$—$R^6$, —$R^5$C(=O)—$NR^9$—$R^{5'}$—$NR^{9'}$—$R^6$—, —$R^5$—C(=O)—O—$R^6$—, —C(=O)—O—$R^6$, —$R^5$-phenyl-$R^6$, —$R^5$-phenyl-, -phenyl-$R^6$—, -phenyl-, —$R^5$-pyrroyl, —$R^5$-pyrazoyl, —$R^5$-imidazoyl, $R^5$-piperazinyl-, —$R^5$-pyridinyl, —$R^5$-pyrimidinyl, —$R^5$-pyrazinyl, —$R^5$-pyridazinyl, —$R^5$-pyrroyl-$R^6$—, —$R^5$-pyrazoyl-$R^6$—, —$R^5$-imidazoyl-$R^6$—, —$R^5$-piperazinyl-$R^6$—, —$R^5$-pyridinyl-$R^6$—, —$R^5$-pyrimidinyl-$R^6$—, —$R^5$-pyrazinyl-$R^6$, —$R^5$-pyridazinyl-$R^6$—, pyrroyl-$R^6$—, pyrazoyl-$R^6$—, imidazoyl-$R^6$-piparazinyl-$R^6$—, pyridinyl-$R^6$—, pyrimidinyl-$R^6$—, pyrazinyl-$R^6$—, pyridazinyl-$R^6$—, pyrroyl, pyrazoyl, imidazoyl, piperazinyl, pyridinyl, pyrimidinyl, pyrazinyl and pyridazinyl, wherein
$R^5$, $R^{5'}$ and $R^6$ are independently from each other selected from the group consisting of $C_1$-$C_{12}$-alkyl and (—$C_2H_4O$—)$_{1-12}$, and wherein,
$R^9$ and $R^{9'}$ are independently from each other selected from the group consisting of H, $C_{1-4}$-alkyl, —$C_{1-6}$-alkyl-$NH_2$, —$C_{1-6}$-alkyl-NHB, —$C_{1-6}$-alkyl-$NB_2$, —$R^{15}$, —$C_{1-6}$-alkyl-$R^{15}$, and —$C_{1-6}$-alkyl-NH—$R^{15}$.

12. The compound according to claim 4 wherein b is 1, T is selected from the group consisting of $C_{1-3}$-alkyl, —$R^5$—C(=O)—$NR^9$—, and —$R^5$—$NR^9$—C(=O)—$R^6$—.

13. The compound according to claim 8 wherein U is a moiety of formula 15 or 19.

14. The compound according to claim 1 wherein V is -pyridinyl- or -pyrimidinyl-.

* * * * *

SEQUENCE LISTING

```
Sequence total quantity: 6
SEQ ID NO: 1            moltype = AA  length = 15
FEATURE                 Location/Qualifiers
REGION                  1..15
                        note = fragment 2-16 of the Histone H3 protein
source                  1..15
                        mol_type = protein
                        organism = synthetic construct
SEQUENCE: 1
ARTKQTARKS TGGKA                                                     15

SEQ ID NO: 2            moltype = AA  length = 13
FEATURE                 Location/Qualifiers
REGION                  1..13
                        note = test peptide
source                  1..13
                        mol_type = protein
```

```
                        organism = synthetic construct
SEQUENCE: 2
AKADEVSLHK WYG                                                                  13

SEQ ID NO: 3           moltype = AA  length = 15
FEATURE                Location/Qualifiers
REGION                 1..15
                       note = fragment 81-95 of the human cytomegalovirus lower
                        matrix phosphoprotein (CMV)
source                 1..15
                       mol_type = protein
                       organism = synthetic construct
SEQUENCE: 3
YFTGSEVENV SVNVH                                                                15

SEQ ID NO: 4           moltype = AA  length = 11
FEATURE                Location/Qualifiers
REGION                 1..11
                       note = fragment 510-520 of humane Lemur Tyrosine Kinase 3
                        (LMTK3)
source                 1..11
                       mol_type = protein
                       organism = synthetic construct
SEQUENCE: 4
PSNPFYEALS T                                                                    11

SEQ ID NO: 5           moltype = AA  length = 20
FEATURE                Location/Qualifiers
REGION                 1..20
                       note = fragment 1-20 of humane amyloid beta
source                 1..20
                       mol_type = protein
                       organism = synthetic construct
SEQUENCE: 5
DAEFRHDSGY EVHHQKLVFF                                                           20

SEQ ID NO: 6           moltype = AA  length = 13
FEATURE                Location/Qualifiers
REGION                 1..13
                       note = test peptide
source                 1..13
                       mol_type = protein
                       organism = synthetic construct
SEQUENCE: 6
CKADEVSMHK WYG                                                                  13
```